US007413877B2

(12) United States Patent
Collier et al.

(10) Patent No.: US 7,413,877 B2

(45) **Date of Patent: *Aug. 19, 2008**

(54) BACTERIAL EXPRESSION OF BOWMAN-BIRK PROTEASE INHIBITORS AND VARIANTS THEREOF

(75) Inventors: Katherine Collier, Los Altos, CA (US); Grant Ganshaw, Tracy, CA (US); Hans De Nobel, Almere (NL); Scott D. Power, San Bruno, CA (US); Anita Van Kimmenade, San Bruno, CA (US); Marc Kolkman, Oegstgeest (NL); Jeffrey Miller, Santa Cruz, CA (US); Brian Schmidt, Halfmoon Bay, CA (US); Gudrun Vogtentanz, Santa Clara, CA (US); David Estell, San Mateo, CA (US)

(73) Assignee: Genencor International, Inc., Palo Alto, CA (US)

(*) Notice: Subject to any disclaimer, the term of this patent is extended or adjusted under 35 U.S.C. 154(b) by 185 days.

This patent is subject to a terminal disclaimer.

(21) Appl. No.: 10/984,514

(22) Filed: Nov. 8, 2004

(65) Prior Publication Data

US 2005/0202535 A1 Sep. 15, 2005

Related U.S. Application Data

(60) Provisional application No. 60/531,207, filed on Dec. 19, 2003, provisional application No. 60/531,189, filed on Dec. 19, 2003, provisional application No. 60/530,954, filed on Dec. 19, 2003, provisional application No. 60/520,403, filed on Nov. 13, 2003, provisional application No. 60/518,154, filed on Nov. 6, 2003.

(51) Int. Cl.
*C12P 29/00* (2006.01)
*C07H 21/04* (2006.01)
*C12N 1/21* (2006.01)

(52) U.S. Cl. ............. 435/71.1; 435/252.3; 435/252.31; 536/23.1

(58) Field of Classification Search ....................... None
See application file for complete search history.

(56) References Cited

U.S. PATENT DOCUMENTS

| | | | | |
|---|---|---|---|---|
| 5,411,873 | A | 5/1995 | Adams et al. | 435/69.1 |
| 5,429,950 | A | 7/1995 | Power et al. | 435/252.31 |
| 5,679,543 | A | 10/1997 | Lawlis | 435/69.1 |
| 6,063,611 | A | 5/2000 | Van Solingen | 435/209 |
| 6,537,968 | B1 | 3/2003 | Lezdey et al. | 514/12 |
| 6,872,563 | B1 * | 3/2005 | Beckwith et al. | 435/252.3 |

FOREIGN PATENT DOCUMENTS

| | | | |
|---|---|---|---|
| WO | WO 88/02025 | * | 8/1987 |
| WO | WO 00/05406 | | 2/2000 |

OTHER PUBLICATIONS

Flecker "Chemical synthesis, molecular cloning and expression of gene coding for a Bowman-Birk-type proteinase inhibitor," Eur. J. Biochem., 1987, 166, 151-6.*

Billings et al., "A Growth-regulated Protease Activity that is Inhibited by the Anticarcinogenic Bowman-Birk Protease Inhibitor," *Proc. Natl. Acad. Sci. USA*, 89:3120-3124 (1992).

Birk, "The Bowman-Birk Inhibitor. Trypsin- and Chymotrypsin-inhibitor from Soybeans," *Int. J. Peptide Protein Res.*, 25:113-131 (1985).

Bode et al., "Natural Protein Proteinase Inhibitors and Their Interaction with Proteinases," *Eur. J. Biochem.*, 204:433-451 (1992).

Chen et al., "Reactive Sites of an Anticarcinogenic Bowman-Birk Proteinase Inhibitor are Similar to Other Trypsin Inhibitors," *The Journal of Biological Chemistry*, 267(3):1990-1994 (1992).

Christmann et al., "The Cystine Knot of a Squash-type Protease Inhibitor as a Structural Scaffold for *Escherichia coli* Cell Surface Display of Conformationally Constrained Peptides," *Protein Engineering*, 12(9):797-806 (1999).

Ferrari et al., "Transcription of *Bacillus subtilis* Subtilisin and Expression of Subtilisin in Sporulation Mutants," *Journal of Bacteriology*, 170(1):289-295 (1988).

Flecker et al., "Chemical Synthesis, Molecular Cloning and Expression of Gene Coding for a Bowman-Birk-type Proteinase Inhibitor," *Eur. J. Biochem.*, 166:151-156 (1987).

Hahn et al., "Regulatory Inputs for the Synthesis of ComK, the Competence Transcription Factor of *Bacillus subtilis," Molecular Microbiology*, 21(4):763-775 (1996).

Henner et al., "Location of the Targets of the *hpr-97, sacU32*(Hy), and *sacQ36*(Hy) Mutations in Upstream Regions of the Subtilisin Promoter," *J. Bact.*, 170(1):296-300 (1988).

Hengen "Purification of His-Tag Fusion Proteins from *Escherichia coli," TIBS*, 20:285-286 (1995).

Kajino et al., "A Protein Disulfide Isomerase Gene Fusion Expression System that Increases the Extracellular Productivity of *Bacillus brevis," Applied and Environmental Microbiology*, 66(2):638:642 (2000).

Kemperman et al., "Identification and Characterization of Two Novel Clostridial Bacteriocins, Circularin A and Closticin 574," *Applied and Environmental Microbiology*, 69(3):1589-1597 (2003).

Kennedy "The Bowman-Birk Inhibitor from Soybeans as an Anticarcinogenic Agent," *Am. J. Clin. Nutr.*, 68:1406S-12S (1998).

Landon, *Methods in Enzymology*, Cleavage at Aspartyl-Prolyl Bonds, Academic Press, Inc., pp. 145-149 (1977).

Lidell et al., "An Autocatalytic Cleavage in the C Terminus of the Human MUC2 Mucin Occurs at the Low pH of the Late Secretory Pathway," *The Journal of Biological Chemistry*, 278(16):13944-13951 (2003).

(Continued)

*Primary Examiner*—Cecilia Tsang
*Assistant Examiner*—Christina Marchetti Brad

(57) ABSTRACT

The present invention provides compositions and methods related to the expression of Bowman-Birk protease inhibitors and variants thereof in bacterial species. The present invention further provides fusion nucleic acids, vectors, fusion polypeptides, and processes for obtaining the Bowman-Birk protease inhibitors.

16 Claims, 14 Drawing Sheets

OTHER PUBLICATIONS

Lin et al., "The 0.25-nm X-ray Structure of the Bowman-Birk-type Inhibitor from Mung Bean in Ternary Complex with Porcine Trypsin," *Eur. J. Biochem.*, 212:549-555 (1993).
Liu, *Soybeans, Chemistry, Technology and Utilization*, pp. 32-35, Aspen Publishers, Inc., Gaithersburg, Maryland (1999).
Meima et al., "The *bdbDC* Operon of *Bacillus subtilis* Encodes Thiol-disulfide Oxidoreductases Required for Competence Developement," *The Journal of Biological Chemistry*, 277(9):6994-7001 (2002).
Neidhardt et al., "Culture Medium for Enterobacteria," *Journal of Bacteriology*, 119(3):736-747 (1974).
Odani et al., "Studies on Soybean Tryspin Inhibitors. IV. Complete Amino Acid Sequence and the Anti-proteinase Sites of Bowman-Birk Soybean Proteinase Inhibitor," *J. Biochem.*, 71:839-848 (1972).
Paine et al., "An Alternative Approach to Depigmentation by Soybean Extracts via Inhibition of the PAR-2 Pathway," *J. Invest. Dermatol.*, 116-587-595 (2001).
Perego, "Integrational Vectors for Genetic Manipulation in *Bacillus subtilis," Bacillus subtilis* and Other Gram-Positive Bacteria: Biochemistry, Physiology, and Molecular Genetics, Sonenshein, Hoch and Losick (eds.) *American Society for Microbiology*, Washington D.C., pp. 615-624 (1993).
Sahu et al., "Inhibition of Human Complement by a C3-Binding Peptide Isolated from a Phage-Displayed Random Peptide Library," *The Journal of Immunology*, 157:884-891 (1996).
Seeboth et al., "In-vitro Cleavage of a Fusion Protein Bound to Cellulose Using the Soluble yscFs ($Kex_2$) Variant," *Appl. Microbiol. Biotechnol.*, 37:621-625 (1992).
Ségalas et al., "A Particularly Labile Asp-Pro Bond in the Green Mamba Muscarinic Toxin MTX2. Effect of Protein Conformation on the Rate of Cleavage," *FEBS Letters*, 371:171-175 (1995).
Shaw et al., "A Novel Combination of Two Classic Catalytic Schemes," *J. Mol. Biol.*, 320:303-309 (2002).
Song et al, "Kunitz-type Soybean Trypsin Inhibitor Revisited: Refined Structure of its Complex with Porcine Trypsin Reveals an Insight into the Interaction Between a Homologous Inhibitor from *Erythrina caffra* and Tissue-type Plasminogen Activator," *J. Mol. Biol.*, 275:347-363 (1998).
Van Tilbeurgh et al., "Fluorogenic and Chromogenic Glycosidases as Substrates and Ligands of Carbohydrases," *Methods in Enzymology*, Academic Press, Inc., pp. 45-59 (1988).
Voss et al., "Crystal Structure of the Bifunctional Soybean Bowman-Birk Inhibitor at 0.28-nm Resolution," *Eur. J. Biochem.*, 242:122-131 (1996).
Werner et al., "Three-Dimensional Structure of Soybean Trypsin/Chymotrypsin Bowman-Birk Inhibitor in Solution," *Biochemistry*, 31:999-1010 (1992).
Wolfson et al., "Modularity of Protein Function : Chimeric Interleukin 1βs Containing Specific Protease Inhibitor Loops Retain Function of Both Molecules," *Biochemistry*, 32:5327-5331 (1993).

* cited by examiner

FIGURE 1.

```
          aprE promoter region
     ~~~~~~~~~~~~~~~~~~~~~~~~~~~~~~~~~~~~~~~~~~~~~~~~~~~~~~
     EcoRI
     ~~~~~
   1 AATTCTCCAT TTTCTTCTGC TATCAAAATA ACAGACTCGT GATTTTCCAA

                    aprE promoter region
     ~~~~~~~~~~~~~~~~~~~~~~~~~~~~~~~~~~~~~~~~~~~~~~~~~~~~~~
  51 ACGAGCTTTC AAAAAAGCCT CTGCCCCTTG CAAATCGGAT GCCTGTCTAT

                    aprE promoter region
     ~~~~~~~~~~~~~~~~~~~~~~~~~~~~~~~~~~~~~~~~~~~~~~~~~~~~~~
                                            EagI
                                           ~~~~~~~
                                            NotI
                                          ~~~~~~~~~
 101 AAAATTCCCG ATATTGGTTA AACAGCGGCG CAATGGCGGC CGCATCTGAT

                    aprE promoter region
     ~~~~~~~~~~~~~~~~~~~~~~~~~~~~~~~~~~~~~~~~~~~~~~~~~~~~~~
 151 GTCTTTGCTT GGCGAATGTT CATCTTATTT CTTCCTCCCT CTCAATAATT

                    aprE promoter region
     ~~~~~~~~~~~~~~~~~~~~~~~~~~~~~~~~~~~~~~~~~~~~~~~~~~~~~~
 201 TTTTCATTCT ATCCCTTTTC TGTAAAGTTT ATTTTTCAGA ATACTTTTAT

                    aprE promoter region
     ~~~~~~~~~~~~~~~~~~~~~~~~~~~~~~~~~~~~~~~~~~~~~~~~~~~~~~
 251 CATCATGCTT TGAAAAAATA TCACGATAAT ATCCATTGTT CTCACGGAAG

                    aprE promoter region
     ~~~~~~~~~~~~~~~~~~~~~~~~~~~~~~~~~~~~~~~~~~~~~~~~~~~~~~
 301 CACACGCAGG TCATTTGAAC GAATTTTTTC GACAGGAATT TGCCGGGACT

                    aprE promoter region
     ~~~~~~~~~~~~~~~~~~~~~~~~~~~~~~~~~~~~~~~~~~~~~~~~~~~~~~
 351 CAGGAGCATT TAACCTAAAA AAGCATGACA TTTCAGCATA ATGAACATTT

                    aprE promoter region
     ~~~~~~~~~~~~~~~~~~~~~~~~~~~~~~~~~~~~~~~~~~~~~~~~~~~~~~
 401 ACTCATGTCT ATTTTCGTTC TTTTCTGTAT GAAAATAGTT ATTTCGAGTC

                    aprE promoter region
     ~~~~~~~~~~~~~~~~~~~~~~~~~~~~~~~~~~~~~~~~~~~~~~~~~~~~~~
 451 TCTACGGAAA TAGCGAGAGA TGATATACCT AAATAGAGAT AAAATCATCT

                    aprE promoter region
     ~~~~~~~~~~~~~~~~~~~~~~~~~~~~~~~~~~~~~~~~~~~~~~~~~~~~~~
 501 CAAAAAAATG GGTCTACTAA AATATTATTC CATCTATTAC AATAAATTCA

                    aprE promoter region
     ~~~~~~~~~~~~~~~~~~~~~~~~~~~~~~~~~~~~~~~~~~~~~~~~~~~~~~
 551 CAGAATAGTC TTTTAAGTAA GTCTACTCTG AATTTTTTTA AAAGGAGAGG

                        AprE signal peptide
            ~~~~~~~~~~~~~~~~~~~~~~~~~~~~~~~~~~~~~~~~~~~~~~~
     aprE promoter region
     ~~~~~~~
             M  R  S  K  K  L  W  I  S  L  L  F  A  L  T
 601 GTAAAGAGTG AGAAGCAAAA AATTGTGGAT CAGCTTGTTG TTTGCGTTAA
```

FIGURE 1. (cont.)

```
                AprE signal peptide
     ~~~~~~~~~~~~~~~~~~~~~~~~~~~~~~~~~~~~~~~~~~~~~~~~
                                                BCE103
                                                ~~~~~~
     · L  I  F   T  M  A   F  S  N  M   S  A  Q   A  D  D
 651 CGTTAATCTT TACGATGGCG TTCAGCAACA TGTCTGCGCA GGCTGATGAT

                           BCE103
     ~~~~~~~~~~~~~~~~~~~~~~~~~~~~~~~~~~~~~~~~~~~~~~~~~~~~~
      Y  S  V  V   E  E  H   G  Q  L   S  I  S  N   G  E  L ·
 701 TATTCAGTTG TAGAGGAACA TGGGCAACTA AGTATTAGTA ACGGTGAATT

                           BCE103
     ~~~~~~~~~~~~~~~~~~~~~~~~~~~~~~~~~~~~~~~~~~~~~~~~~~~~~
                                                 NcoI
                                                 ~~~~~
     ·V  N  E   R  G  E  Q   V  Q  L   K  G  M   S  S  H  G ·
 751 AGTCAATGAA CGAGGCGAAC AAGTTCAGTT AAAAGGGATG AGTTCCCATG

                           BCE103
     ~~~~~~~~~~~~~~~~~~~~~~~~~~~~~~~~~~~~~~~~~~~~~~~~~~~~~
     NcoI
     ~
     · L  Q  W   Y  G  Q   F  V  N  Y   E  S  M   K  W  L
 801 GTTTGCAATG GTACGGTCAA TTTGTAAACT ATGAAAGCAT GAAATGGCTA

                           BCE103
     ~~~~~~~~~~~~~~~~~~~~~~~~~~~~~~~~~~~~~~~~~~~~~~~~~~~~~
      R  D  D  W   G  I  T   V  F  R   A  A  M  Y   T  S  S ·
 851 AGAGATGATT GGGGAATAAC TGTATTCCGA GCAGCAATGT ATACCTCTTC

                           BCE103
     ~~~~~~~~~~~~~~~~~~~~~~~~~~~~~~~~~~~~~~~~~~~~~~~~~~~~~
     ·G  G  Y   I  D  D  P   S  V  K   E  K  V   K  E  T  V ·
 901 AGGAGGATAT ATTGACGATC CATCAGTAAA GGAAAAAGTA AAAGAGACTG

                           BCE103
     ~~~~~~~~~~~~~~~~~~~~~~~~~~~~~~~~~~~~~~~~~~~~~~~~~~~~~
     · E  A  A   I  D  L   G  I  Y  V   I  I  D   W  H  I
 951 TTGAGGCTGC GATAGACCTT GGCATATATG TGATCATTGA TTGGCATATC

                           BCE103
     ~~~~~~~~~~~~~~~~~~~~~~~~~~~~~~~~~~~~~~~~~~~~~~~~~~~~~
      L  S  D  N   D  P  N   I  Y  K   E  E  A  K   D  F  F ·
1001 CTTTCAGACA ATGACCCGAA TATATATAAA GAAGAAGCGA AGGATTTCTT

                           BCE103
     ~~~~~~~~~~~~~~~~~~~~~~~~~~~~~~~~~~~~~~~~~~~~~~~~~~~~~
     ·D  E  M   S  E  L  Y   G  D  Y   P  N  V   I  Y  E  I ·
1051 TGATGAAATG TCAGAGTTGT ATGGAGACTA TCCGAATGTG ATATACGAAA

                           BCE103
     ~~~~~~~~~~~~~~~~~~~~~~~~~~~~~~~~~~~~~~~~~~~~~~~~~~~~~
     · A  N  E   P  N  G   S  D  V  T   W  D  N   Q  I  K
1101 TTGCAAATGA ACCGAATGGT AGTGATGTTA CGTGGGACAA TCAAATAAAA

                           BCE103
     ~~~~~~~~~~~~~~~~~~~~~~~~~~~~~~~~~~~~~~~~~~~~~~~~~~~~~
      P  Y  A  E   E  V  I   P  V  I   R  D  N  D   P  N  N ·
1151 CCGTATGCAG AAGAAGTGAT TCCGGTTATT CGTGACAATG ACCCTAATAA
```

FIGURE 1. (cont.)

```
                              BCE103
      ~~~~~~~~~~~~~~~~~~~~~~~~~~~~~~~~~~~~~~~~~~~~~~~~~~~~~~
      · I  V  I   V  G  T  G   T  W  S   Q  D  V   H  H  A  A ·
1201 CATTGTTATT GTAGGTACAG GTACATGGAG TCAGGATGTC CATCATGCAG

                              BCE103
      ~~~~~~~~~~~~~~~~~~~~~~~~~~~~~~~~~~~~~~~~~~~~~~~~~~~~~~
      ·  D  N  Q   L  A  D   P  N  V  M   Y  A  F   H  F  Y
1251 CCGATAATCA GCTTGCAGAT CCTAACGTCA TGTATGCATT TCATTTTTAT

                              BCE103
      ~~~~~~~~~~~~~~~~~~~~~~~~~~~~~~~~~~~~~~~~~~~~~~~~~~~~~~
       A  G  T  H   G  Q  N   L  R  D   Q  V  D  Y   A  L  D ·
1301 GCAGGAACAC ATGGACAAAA TTTACGAGAC CAAGTAGATT ATGCATTAGA

                              BCE103
      ~~~~~~~~~~~~~~~~~~~~~~~~~~~~~~~~~~~~~~~~~~~~~~~~~~~~~~
      · Q  G  A   A  I  F  V   S  E  W   G  T  S   A  A  T  G ·
1351 TCAAGGAGCA GCGATATTTG TTAGTGAATG GGGGACAAGT GCAGCTACAG

                              BCE103
      ~~~~~~~~~~~~~~~~~~~~~~~~~~~~~~~~~~~~~~~~~~~~~~~~~~~~~~
      ·  D  G  G   V  F  L   D  E  A  Q   V  W  I   D  F  M
1401 GTGATGGTGG TGTGTTTTTA GATGAAGCAC AAGTGTGGAT TGACTTTATG

                              BCE103
      ~~~~~~~~~~~~~~~~~~~~~~~~~~~~~~~~~~~~~~~~~~~~~~~~~~~~~~
       D  E  R  N   L  S  W   A  N  W   S  L  T  H   K  D  E ·
1451 GATGAAAGAA ATTTAAGCTG GGCCAACTGG TCTCTAACGC ATAAGGATGA

                              BCE103
      ~~~~~~~~~~~~~~~~~~~~~~~~~~~~~~~~~~~~~~~~~~~~~~~~~~~~~~
            PstI
           ~~~~~~~
      · S  S  A   A  L  M  P   G  A  N   P  T  G   G  W  T  E ·
1501 GTCATCTGCA GCGTTAATGC CAGGTGCAAA TCCAACTGGT GGTTGGACAG

                              BCE103
      ~~~~~~~~~~~~~~~~~~~~~~~~~~~~~~~~~~~~~~~~~~~~~~~~~~~~~~
      ·  A  E  L   S  P  S   G  T  F  V   R  E  K   I  R  E
1551 AGGCTGAACT ATCTCCATCT GGTACATTTG TGAGGGAAAA AATAAGAGAA

         BCE103
      ~~~~~~~~~~~~~
                                  1st CBD Linker
                   ~~~~~~~~~~~~~~~~~~~~~~~~~~~~~~~~~~~~~~~~~
       S  A  S  I   P  P  S   D  P  T   P  P  S  D   P  G  E ·
1601 TCAGCATCTA TTCCGCCAAG CGATCCAACA CCGCCATCTG ATCCAGGAGA

                                      BBI
            ~~~~~~~~~~~~~~~~~~~~~~~~~~~~~~~~~~~~~~~~~~~
         fusion site
         ~~~~~~
      1st CBD Linker
      ~~~~~~~~~~~
         BamHI            SacI
         ~~~~~~         ~~~~~~~
      · P  D  P   D  D  E  S   S  K  P   C  C  D   Q  C  A  C ·
1651 ACCGGATCCA GACGATGAGA GCTCTAAACC CTGTTGCGAT CAATGCGCAT
```

FIGURE 1. (cont.)

```
                               BBI
     ~~~~~~~~~~~~~~~~~~~~~~~~~~~~~~~~~~~~~~~~~~~~~~~~~~~~~
     · T  K  S   N  P  P   Q  C  R  C   S  D  M   R  L  N
1701 GTACGAAATC AAATCCTCCA CAGTGTCGGT GTTCCGATAT GCGTCTGAAT

                               BBI
     ~~~~~~~~~~~~~~~~~~~~~~~~~~~~~~~~~~~~~~~~~~~~~~~~~~~~~
                  SphI
                 ~~~~~~
      S  C  H  S   A  C  K   S  C  I   C  A  L  S   Y  P  A ·
1751 AGCTGTCATA GTGCATGCAA AAGCTGTATC TGCGCCCTGA GTTATCCAGC

                               BBI
     ~~~~~~~~~~~~~~~~~~~~~~~~~~~~~~~~~~~~~~~~~~~~~~~~~~~~~
                   SalI
                  ~~~~~~
     · Q  C  F   C  V  D  I   T  D  F   C  Y  E   P  C  K  P ·
1801 TCAATGTTTT TGCGTCGACA TCACGGACTT CTGCTATGAG CCATGTAAAC

                                       6xHIS
                               ~~~~~~~~~~~~~~~~~~~~
              BBI
     ~~~~~~~~~~~~~~~~~~~~~~~~~
     ·  S  E  D   D  K  E   N  H  H   H  H  H  H  Stop  (SEQ ID NO:2)
1851 CAAGCGAGGA CGATAAAGAG AACCATCATC ACCATCACCA TTAAAAGTTA

                  LAT terminator
            ~~~~~~~~~~~~~~~~~~~~~~~~~~~~~~~~~~~~~~~~
                                                 HindIII
                                                 ~~~~~~
1901 ACAGAGGACG GATTTCCTGA AGGAAATCCG TTTTTTTATT TTTAAGCTTG (SEQ ID NO:1)
```

FIGURE 3.

```
    ~~~~~~
                          12BBIck81
           ~~~~~~~~~~~~~~~~~~~~~~~~~~~~~~~~~~~~~~~~~~~~~~~~
    BamHI            SacI
    ~~~~~~          ~~~~~~~
     D  P  D   D  E  S  S   K  P  C   C  D  Q   C  A  C  Y ·
  1 GGATCCAGAC GATGAGAGCT CTAAACCCTG TTGCGATCAA TGCGCATGTT
    CCTAGGTCTG CTACTCTCGA GATTTGGGAC AACGCTAGTT ACGCGTACAA

                      12BBIck81
    ~~~~~~~~~~~~~~~~~~~~~~~~~~~~~~~~~~~~~~~~~~~~~~~~~~~~~~~
                               PstI              EcoRI
                              ~~~~~~~            ~~~~~~
    ·  N  L  Y   G  W  T   C  R  C  S   D  M  R   L  N  S
 51 ATAATTTGTA TGGGTGGACT TGTCGCTGCA GCGATATGCG TCTGAATTCC
    TATTAAACAT ACCCACCTGA ACAGCGACGT CGCTATACGC AGACTTAAGG

                      12BBIck81
    ~~~~~~~~~~~~~~~~~~~~~~~~~~~~~~~~~~~~~~~~~~~~~~~~~~~~~~~
     C  H  S  A   C  K  S   C  A  C   Y  N  L  Y   G  W  T ·
101 TGTCATAGTG CCTGCAAAAG CTGCGCATGT TATAACCTGT ACGGGTGGAC
    ACAGTATCAC GGACGTTTTC GACGCGTACA ATATTGGACA TGCCCACCTG

                      12BBIck81
    ~~~~~~~~~~~~~~~~~~~~~~~~~~~~~~~~~~~~~~~~~~~~~~~~~~~~~~~
                SalI
               ~~~~~~
    · C  F  C   V  D  I  T   D  F  C   Y  E  P   C  K  P  S ·
151 CTGTTTTTGC GTCGACATCA CGGACTTCTG CTATGAGCCA TGTAAACCAA
    GACAAAAACG CAGCTGTAGT GCCTGAAGAC GATACTCGGT ACATTTGGTT

           12BBIck81
    ~~~~~~~~~~~~~~~~~~~~~~~~~
    ·  E  D  D   K  E  N   *  (SEQ ID NO:4)
201 GCGAGGACGA TAAAGAGAAC TAA (SEQ ID NO:3)
    CGCTCCTGCT ATTTCTCTTG ATT
```

FIGURE 7.

```
                          hiPDI
                   ~~~~~~~~~~~~~~~~~~~~~~~~~~~~~~~~~~~~~~~~~~~
     AprE signal cleavage site
     ~~~~~~~~~~~~~
      BssHII   NheI        BsrGI
      ~~~~~~  ~~~~~~~      ~~~~~~
      S  A  Q  A   S  D  V   V  Q  L   K  K  D  T   F  D  D ·
   1 AGCGCGCAGG CTAGCGATGT TGTACAACTG AAAAAAGACA CTTTCGACGA
     TCGCGCGTCC GATCGCTACA ACATGTTGAC TTTTTTCTGT GAAAGCTGCT

                              hiPDI
     ~~~~~~~~~~~~~~~~~~~~~~~~~~~~~~~~~~~~~~~~~~~~~~~~~~~~~~~
     · F  I  K   T  N  D  L   V  L  A   E  F  F   A  P  W  C ·
  51 CTTCATCAAA ACAAATGACC TTGTTCTTGC TGAATTTTTC GCGCCGTGGT
     GAAGTAGTTT TGTTTACTGG AACAAGAACG ACTTAAAAAG CGCGGCACCA

                              hiPDI
     ~~~~~~~~~~~~~~~~~~~~~~~~~~~~~~~~~~~~~~~~~~~~~~~~~~~~~~~
     · G  H  C   K  A  L   A  P  E  Y   E  E  A   A  T  T
 101 GCGGTCACTG CAAAGCTCTT GCTCCTGAGT ACGAGGAAGC TGCAACTACA
     CGCCAGTGAC GTTTCGAGAA CGAGGACTCA TGCTCCTTCG ACGTTGATGT

                              hiPDI
     ~~~~~~~~~~~~~~~~~~~~~~~~~~~~~~~~~~~~~~~~~~~~~~~~~~~~~~~
      L  K  E  K   N  I  K   L  A  K   V  D  C  T   E  E  T ·
 151 CTGAAAGAAA AGAACATCAA ACTTGCTAAA GTAGACTGCA CAGAAGAGAC
     GACTTTCTTT TCTTGTAGTT TGAACGATTT CATCTGACGT GTCTTCTCTG

                              hiPDI
     ~~~~~~~~~~~~~~~~~~~~~~~~~~~~~~~~~~~~~~~~~~~~~~~~~~~~~~~
     · D  L  C   Q  Q  H  G   V  E  G   Y  P  T   L  K  V  F ·
 201 TGATCTTTGC CAACAACATG GTGTTGAGGG CTACCCAACT CTTAAAGTTT
     ACTAGAAACG GTTGTTGTAC CACAACTCCC GATGGGTTGA GAATTTCAAA

                              hiPDI
     ~~~~~~~~~~~~~~~~~~~~~~~~~~~~~~~~~~~~~~~~~~~~~~~~~~~~~~~
     · R  G  L   D  N  V   S  P  Y  K   G  Q  R   K  A  A
 251 TCCGTGGCCT TGACAACGTA TCTCCTTACA AAGGTCAACG TAAAGCTGCT
     AGGCACCGGA ACTGTTGCAT AGAGGAATGT TTCCAGTTGC ATTTCGACGA

                              hiPDI
     ~~~~~~~~~~~~~~~~~~~~~~~~~~~~~~~~~~~~~~~~~~~~~~~~~~~~~~~
      A  I  T  S   Y  M  I   K  Q  S   L  P  A  V   S  E  V ·
 301 GCAATCACTT CATACATGAT CAAACAATCT CTGCCTGCTG TATCTGAAGT
     CGTTAGTGAA GTATGTACTA GTTTGTTAGA GACGGACGAC ATAGACTTCA

                              hiPDI
     ~~~~~~~~~~~~~~~~~~~~~~~~~~~~~~~~~~~~~~~~~~~~~~~~~~~~~~~
     · T  K  D   N  L  E  E   F  K  K   A  D  K   A  V  L  V ·
 351 TACAAAAGAC AACCTTGAAG AATTTAAAAA AGCTGACAAA GCTGTTCTTG
     ATGTTTTCTG TTGGAACTTC TTAAATTTTT TCGACTGTTT CGACAAGAAC

                              hiPDI
     ~~~~~~~~~~~~~~~~~~~~~~~~~~~~~~~~~~~~~~~~~~~~~~~~~~~~~~~
     · A  Y  V   D  A  S   D  K  A  S   S  E  V   F  T  Q
 401 TTGCTTATGT AGATGCTTCT GACAAAGCAT CTAGCGAAGT TTTCACTCAA
     AACGAATACA TCTACGAAGA CTGTTTCGTA GATCGCTTCA AAAGTGAGTT

                              hiPDI
     ~~~~~~~~~~~~~~~~~~~~~~~~~~~~~~~~~~~~~~~~~~~~~~~~~~~~~~~
      V  A  E  K   L  R  D   N  Y  P   F  G  S  S   S  D  A ·
 451 GTTGCTGAAA AACTGCGCGA TAACTACCCA TTCGGCTCTA GCTCTGATGC
     CAACGACTTT TTGACGCGCT ATTGATGGGT AAGCCGAGAT CGAGACTACG
```

FIGURE 7 (cont.)

```
                                 hiPDI
       ~~~~~~~~~~~~~~~~~~~~~~~~~~~~~~~~~~~~~~~~~~~~~~~~~~~~~~~
       ·A  L  A   E  A  E  G   V  K  A   P  A  I   V  L  Y  K·
 501   TGCACTGGCT GAAGCTGAGG GCGTTAAAGC ACCTGCTATT GTTCTTTACA
       ACGTGACCGA CTTCGACTCC CGCAATTTCG TGGACGATAA CAAGAAATGT

                                 hiPDI
       ~~~~~~~~~~~~~~~~~~~~~~~~~~~~~~~~~~~~~~~~~~~~~~~~~~~~~~~
       · D  F  D   E  G  K   A  V  F  S   E  K  F   E  V  E
 551   AAGACTTTGA TGAAGGTAAA GCGGTTTTCT CTGAAAAATT CGAAGTAGAG
       TTCTGAAACT ACTTCCATTT CGCCAAAAGA GACTTTTTAA GCTTCATCTC

                                 hiPDI
       ~~~~~~~~~~~~~~~~~~~~~~~~~~~~~~~~~~~~~~~~~~~~~~~~~~~~~~~
        A  I  E  K   F  A  K   T  G  A   T  P  L  I   G  E  I·
 601   GCAATCGAAA AATTCGCTAA AACAGGTGCT ACTCCACTTA TTGGCGAAAT
       CGTTAGCTTT TTAAGCGATT TTGTCCACGA TGAGGTGAAT AACCGCTTTA

                                 hiPDI
       ~~~~~~~~~~~~~~~~~~~~~~~~~~~~~~~~~~~~~~~~~~~~~~~~~~~~~~~
       ·G  P  E   T  Y  S  D   Y  M  S   A  G  I   P  L  A  Y·
 651   CGGACCTGAA ACTTACTCTG ATTACATGTC AGCTGGCATC CCTCTGGCAT
       GCCTGGACTT TGAATGAGAC TAATGTACAG TCGACCGTAG GGAGACCGTA

                                 hiPDI
       ~~~~~~~~~~~~~~~~~~~~~~~~~~~~~~~~~~~~~~~~~~~~~~~~~~~~~~~
                                  SapI
                                 ~~~~~~~
       · I  F  A   E  T  A   E  E  R  K   E  L  S   D  K  L
 701   ACATTTTCGC TGAAACAGCT GAAGAGCGTA AAGAACTCAG CGACAAACTT
       TGTAAAAGCG ACTTTGTCGA CTTCTCGCAT TTCTTGAGTC GCTGTTTGAA

                                 hiPDI
       ~~~~~~~~~~~~~~~~~~~~~~~~~~~~~~~~~~~~~~~~~~~~~~~~~~~~~~~
        K  P  I  A   E  A  Q   R  G  V   I  N  F  G   T  I  D·
 751   AAACCAATCG CTGAAGCTCA ACGTGGCGTT ATTAACTTTG GTACTATTGA
       TTTGGTTAGC GACTTCGAGT TGCACCGCAA TAATTGAAAC CATGATAACT

                                 hiPDI
       ~~~~~~~~~~~~~~~~~~~~~~~~~~~~~~~~~~~~~~~~~~~~~~~~~~~~~~~
       ·A  K  A   F  G  A  H   A  G  N   L  N  L   K  T  D  K·
 801   CGCTAAAGCA TTTGGTGCTC ACGCTGGAAA CCTGAATCTG AAAACTGACA
       GCGATTTCGT AAACCACGAG TGCGACCTTT GGACTTAGAC TTTTGACTGT

                                 hiPDI
       ~~~~~~~~~~~~~~~~~~~~~~~~~~~~~~~~~~~~~~~~~~~~~~~~~~~~~~~
       · F  P  A   F  A  I   Q  E  V  A   K  N  Q   K  F  P
 851   AATTCCCTGC TTTCGCAATC CAAGAAGTTG CTAAAAACCA AAAATTCCCT
       TTAAGGGACG AAAGCGTTAG GTTCTTCAAC GATTTTTGGT TTTTAAGGGA

                                 hiPDI
       ~~~~~~~~~~~~~~~~~~~~~~~~~~~~~~~~~~~~~~~~~~~~~~~~~~~~~~~
        F  D  Q  E   K  E  I   T  F  E   A  I  K  A   F  V  D·
 901   TTTGATCAAG AAAAAGAAAT TACTTTTGAA GCGATCAAAG CATTCGTTGA
       AAACTAGTTC TTTTTCTTTA ATGAAAACTT CGCTAGTTTC GTAAGCAACT

                                 hiPDI
       ~~~~~~~~~~~~~~~~~~~~~~~~~~~~~~~~~~~~~~~~~~~~~~~~~~~~~~~
       ·D  F  V   A  G  K  I   E  P  S   I  K  S   E  P  I  P·
 951   CGATTTTGTT GCTGGTAAAA TCGAACCAAG CATCAAATCA GAACCAATCC
       GCTAAAACAA CGACCATTTT AGCTTGGTTC GTAGTTTAGT CTTGGTTAGG

                                 hiPDI
       ~~~~~~~~~~~~~~~~~~~~~~~~~~~~~~~~~~~~~~~~~~~~~~~~~~~~~~~
       · E  K  Q   E  G  P   V  T  V  V   V  A  K   N  Y  N
1001   CTGAAAAACA AGAAGGTCCT GTTACTGTAG TTGTAGCTAA AAACTACAAT
       GACTTTTTGT TCTTCCAGGA CAATGACATC AACATCGATT TTTGATGTTA
```

FIGURE 7. (cont.)

```
                                hiPDI
        ~~~~~~~~~~~~~~~~~~~~~~~~~~~~~~~~~~~~~~~~~~~~~~~~~~~~~~~
         E  I  V  L   D  D  T   K  D  V   L  I  E  F   Y  A  P ·
1051    GAAATCGTTC TGGACGATAC TAAAGATGTA TTAATTGAAT TTTACGCTCC
        CTTTAGCAAG ACCTGCTATG ATTTCTACAT AATTAACTTA AAATGCGAGG

                                hiPDI
        ~~~~~~~~~~~~~~~~~~~~~~~~~~~~~~~~~~~~~~~~~~~~~~~~~~~~~~~
        ·W  C  G   H  C  K  A   L  A  P   K  Y  E   E  L  G  A ·
1101    TTGGTGCGGT CACTGCAAAG CTCTTGCTCC TAAATACGAA GAACTTGGTG
        AACCACGCCA GTGACGTTTC GAGAACGAGG ATTTATGCTT CTTGAACCAC

                                hiPDI
        ~~~~~~~~~~~~~~~~~~~~~~~~~~~~~~~~~~~~~~~~~~~~~~~~~~~~~~~
        · L  Y  A   K  S  E   F  K  D  R   V  V  I   A  K  V
1151    CTCTGTATGC AAAAAGCGAG TTCAAAGACC GTGTTGTAAT TGCTAAAGTT
        GAGACATACG TTTTTCGCTC AAGTTTCTGG CACAACATTA ACGATTTCAA

                                hiPDI
        ~~~~~~~~~~~~~~~~~~~~~~~~~~~~~~~~~~~~~~~~~~~~~~~~~~~~~~~
         D  A  T  A   N  D  V   P  D  E   I  Q  G  F   P  T  I ·
1201    GATGCAACAG CTAACGATGT TCCAGATGAA ATTCAAGGAT TCCCTACTAT
        CTACGTTGTC GATTGCTACA AGGTCTACTT TAAGTTCCTA AGGGATGATA

                                hiPDI
        ~~~~~~~~~~~~~~~~~~~~~~~~~~~~~~~~~~~~~~~~~~~~~~~~~~~~~~~
        ·K  L  Y   P  A  G  A   K  G  Q   P  V  T   Y  S  G  S ·
1251    CAAACTATAC CCAGCTGGTG CAAAAGGTCA ACCTGTTACT TACTCTGGTT
        GTTTGATATG GGTCGACCAC GTTTTCCAGT TGGACAATGA ATGAGACCAA

                                hiPDI
        ~~~~~~~~~~~~~~~~~~~~~~~~~~~~~~~~~~~~~~~~~~~~~~~~~~~~~~~
        · R  T  V   E  D  L   I  K  F  I   A  E  N   G  K  Y
1301    CACGCACTGT TGAAGACCTT ATCAAATTCA TTGCTGAAAA CGGTAAATAC
        GTGCGTGACA ACTTCTGGAA TAGTTTAAGT AACGACTTTT GCCATTTATG

                                hiPDI
        ~~~~~~~~~~~~~~~~~~~~~~~~~~~~~~~~~~~~~~~~~~~~~~~~~~~~~~~
                                              SpeI
                                             ~~~~~~
         K  A  A  I   S  E  D   A  E  E   T  S  S  A   T  E  T ·
1351    AAAGCTGCAA TCTCAGAAGA TGCTGAAGAG ACTAGTTCAG CAACTGAAAC
        TTTCGACGTT AGAGTCTTCT ACGACTTCTC TGATCAAGTC GTTGACTTTG

                                hiPDI
        ~~~~~~~~~~~~~~~~~~~~~~~~~~~~~~~~~~~~~~~~~~~~~~~~~~~~~~~
        ·T  T  E   T  A  T  K   S  E  E   A  A  K   E  T  A  T ·
1401    AACTACAGAA ACTGCTACAA AGTCAGAAGA AGCTGCAAAA GAAACTGCAA
        TTGATGTCTT TGACGATGTT TCAGTCTTCT TCGACGTTTT CTTTGACGTT

                              Enteropeptidase cleavage linker
                           ~~~~~~~~~~~~~~~~~~~~~~~~~~~~~~~~
              hiPDI                                          N-term BBI
        ~~~~~~~~~~~~~~~~~~                                   ~~~
        ·  E  H  D   E  L  G   S  G  S  G   D  D  D   D  K  D
1451    CAGAACACGA CGAACTTGGA TCTGGTTCCG GAGATGACGA TGACAAAGAC
        GTCTTGTGCT GCTTGAACCT AGACCAAGGC CTCTACTGCT ACTGTTTCTG

         N-term BBI
        ~~~~~~~~~~~~~
              SacI
             ~~~~~~~
         D  E  S  S
1501    GATGAGAGCT CT   (SEQ ID NO:5)
       CTACTCTCGA GA   (SEQ ID NO:6)
```

FIGURE 8.

```
                aprE promoter
    ~~~~~~~~~~~~~~~~~~~~~~~~~~~~~~~~~~~~~~~~~~~~~~~~~~~~~~~
    EcoRI
    ~~~~~~
  1 GAATTCTCCA TTTTCTTCTG CTATCAAAAT AACAGACTCG TGATTTTCCA
    CTTAAGAGGT AAAAGAAGAC GATAGTTTTA TTGTCTGAGC ACTAAAAGGT

                         aprE promoter
    ~~~~~~~~~~~~~~~~~~~~~~~~~~~~~~~~~~~~~~~~~~~~~~~~~~~~~~~
 51 AACGAGCTTT CAAAAAAGCC TCTGCCCCTT GCAAATCGGA TGCCTGTCTA
    TTGCTCGAAA GTTTTTTCGG AGACGGGGAA CGTTTAGCCT ACGGACAGAT

                         aprE promoter
    ~~~~~~~~~~~~~~~~~~~~~~~~~~~~~~~~~~~~~~~~~~~~~~~~~~~~~~~
                                          NotI
                                        ~~~~~~~~~
101 TAAAATTCCC GATATTGGTT AAACAGCGGC GCAATGGCGG CCGCATCTGA
    ATTTTAAGGG CTATAACCAA TTTGTCGCCG CGTTACCGCC GGCGTAGACT

                         aprE promoter
    ~~~~~~~~~~~~~~~~~~~~~~~~~~~~~~~~~~~~~~~~~~~~~~~~~~~~~~~
151 TGTCTTTGCT TGGCGAATGT TCATCTTATT TCTTCCTCCC TCTCAATAAT
    ACAGAAACGA ACCGCTTACA AGTAGAATAA AGAAGGAGGG AGAGTTATTA

                         aprE promoter
    ~~~~~~~~~~~~~~~~~~~~~~~~~~~~~~~~~~~~~~~~~~~~~~~~~~~~~~~
201 TTTTTCATTC TATCCCTTTT CTGTAAAGTT TATTTTTCAG AATACTTTTA
    AAAAAGTAAG ATAGGGAAAA GACATTTCAA ATAAAAAGTC TTATGAAAAT

                         aprE promoter
    ~~~~~~~~~~~~~~~~~~~~~~~~~~~~~~~~~~~~~~~~~~~~~~~~~~~~~~~
251 TCATCATGCT TTGAAAAAAT ATCACGATAA TATCCATTGT TCTCACGGAA
    AGTAGTACGA AACTTTTTTA TAGTGCTATT ATAGGTAACA AGAGTGCCTT

                         aprE promoter
    ~~~~~~~~~~~~~~~~~~~~~~~~~~~~~~~~~~~~~~~~~~~~~~~~~~~~~~~
301 GCACACGCAG GTCATTTGAA CGAATTTTTT CGACAGGAAT TTGCCGGGAC
    CGTGTGCGTC CAGTAAACTT GCTTAAAAAA GCTGTCCTTA AACGGCCCTG

                         aprE promoter
    ~~~~~~~~~~~~~~~~~~~~~~~~~~~~~~~~~~~~~~~~~~~~~~~~~~~~~~~
351 TCAGGAGCAT TTAACCTAAA AAAGCATGAC ATTTCAGCAT AATGAACATT
    AGTCCTCGTA AATTGGATTT TTTCGTACTG TAAAGTCGTA TTACTTGTAA

                         aprE promoter
    ~~~~~~~~~~~~~~~~~~~~~~~~~~~~~~~~~~~~~~~~~~~~~~~~~~~~~~~
401 TACTCATGTC TATTTTTCGTT CTTTTCTGTA TGAAAATAGT TATTTCGAGT
    ATGAGTACAG ATAAAAGCAA GAAAAGACAT ACTTTTATCA ATAAAGCTCA

                         aprE promoter
    ~~~~~~~~~~~~~~~~~~~~~~~~~~~~~~~~~~~~~~~~~~~~~~~~~~~~~~~
451 CTCTACGGAA ATAGCGAGAG ATGATATACC TAAATAGAGA TAAAATCATC
    GAGATGCCTT TATCGCTCTC TACTATATGG ATTTATCTCT ATTTTAGTAG

                         aprE promoter
    ~~~~~~~~~~~~~~~~~~~~~~~~~~~~~~~~~~~~~~~~~~~~~~~~~~~~~~~
501 TCAAAAAAAT GGGTCTACTA AAATATTATT CCATCTATTA CAATAAATTC
    AGTTTTTTTA CCCAGATGAT TTTATAATAA GGTAGATAAT GTTATTTAAG

                         aprE promoter
    ~~~~~~~~~~~~~~~~~~~~~~~~~~~~~~~~~~~~~~~~~~~~~~~~~~~~~~~
551 ACAGAATAGT CTTTTAAGTA AGTCTACTCT GAATTTTTTT AAAAGGAGAG
    TGTCTTATCA GAAAATTCAT TCAGATGAGA CTTAAAAAAA TTTTCCTCTC

    aprE promoter                      Cutinase signal peptide
    ~~~~~~~~                           ~~~~~~~~~~~~~~~~~~~
              AprE signal peptide
```

FIGURE 8 (cont.)

```
           ~~~~~~~~~~~~~~~~~~~~~~~~~~
            V  R  S  K  K  L  W  I  S  L  L  F  A  L
 601  GGTAAAGAGT GAGAAGCAAA AAATTGTGGA TCAGCTTGTT GTTTGCGTTA
      CCATTTCTCA CTCTTCGTTT TTTAACACCT AGTCGAACAA CAAACGCAAT

                                                   Cutinase
                                                   ~~~~~
              Cutinase signal peptide
      ~~~~~~~~~~~~~~~~~~~~~~~~~~~~~~~~~~~~~~~~~~~~~~~
       T  L  A  A   S  C  L   S  V  C   A  T  V  A   A  A  P ·
 651  ACGCTGGCGG CCTCTTGCCT GTCCGTCTGT GCCACTGTCG CGGCGGCTCC
      TGCGACCGCC GGAGAACGGA CAGGCAGACA CGGTGACAGC GCCGCCGAGG

                        Cutinase
      ~~~~~~~~~~~~~~~~~~~~~~~~~~~~~~~~~~~~~~~~~~~~~~~~~~~~
      · L  P  D   T  P  G  A   P  F  P   A  V  A   N  F  D  R ·
 701  CCTGCCGGAT ACACCGGGAG CGCCATTTCC GGCTGTCGCC AATTTCGACC
      GGACGGCCTA TGTGGCCCTC GCGGTAAAGG CCGACAGCGG TTAAAGCTGG

                        Cutinase
      ~~~~~~~~~~~~~~~~~~~~~~~~~~~~~~~~~~~~~~~~~~~~~~~~~~~~
      ·  S  G  P   Y  T  T   S  S  Q  S   E  G  P   S  C  R
 751  GCAGTGGCCC CTACACCACC AGCAGCCAGA GCGAGGGGCC GAGCTGTCGC
      CGTCACCGGG GATGTGGTGG TCGTCGGTCT CGCTCCCCGG CTCGACAGCG

                        Cutinase
      ~~~~~~~~~~~~~~~~~~~~~~~~~~~~~~~~~~~~~~~~~~~~~~~~~~~~
       I  Y  R  P   R  D  L   G  Q  G   G  V  R  H   P  V  I ·
 801  ATCTATCGGC CCCGCGACCT GGGTCAGGGG GGCGTGCGTC ATCCGGTGAT
      TAGATAGCCG GGGCGCTGGA CCCAGTCCCC CCGCACGCAG TAGGCCACTA

                        Cutinase
      ~~~~~~~~~~~~~~~~~~~~~~~~~~~~~~~~~~~~~~~~~~~~~~~~~~~~
      · L  W  G   N  G  T  G   A  G  P   S  T  Y   A  G  L  L ·
 851  TCTCTGGGGC AATGGCACCG GTGCCGGGCC GTCCACCTAT GCCGGCTTGC
      AGAGACCCCG TTACCGTGGC CACGGCCCGG CAGGTGGATA CGGCCGAACG

                        Cutinase
      ~~~~~~~~~~~~~~~~~~~~~~~~~~~~~~~~~~~~~~~~~~~~~~~~~~~~
      ·  S  H  W   A  S  H   G  F  V  V   A  A  A   E  T  S
 901  TATCGCACTG GCAAGCCAC GGTTTCGTGG TGGCGGCGGC GGAAACCTCC
      ATAGCGTGAC CCGTTCGGTG CCAAAGCACC ACCGCCGCCG CCTTTGGAGG

                        Cutinase
      ~~~~~~~~~~~~~~~~~~~~~~~~~~~~~~~~~~~~~~~~~~~~~~~~~~~~
       N  A  G  T   G  R  E   M  L  A   C  L  D  Y   L  V  R ·
 951  AATGCCGGTA CCGGGCGGGA AATGCTCGCC TGCCTGGACT ATCTGGTACG
      TTACGGCCAT GGCCCGCCCT TTACGAGCGG ACGGACCTGA TAGACCATGC

                        Cutinase
      ~~~~~~~~~~~~~~~~~~~~~~~~~~~~~~~~~~~~~~~~~~~~~~~~~~~~
      · E  N  D   T  P  Y  G   T  Y  S   G  K  L   N  T  G  R ·
1001  TGAGAACGAC ACCCCCTACG GCACCTATTC CGGCAAGCTC AATACCGGGC
      ACTCTTGCTG TGGGGGATGC CGTGGATAAG GCCGTTCGAG TTATGGCCCG

                        Cutinase
      ~~~~~~~~~~~~~~~~~~~~~~~~~~~~~~~~~~~~~~~~~~~~~~~~~~~~
      ·  V  G  T   S  G  H   S  Q  G  G   G  G  S   I  M  A
1051  GAGTCGGCAC TTCTGGGCAT TCCCAGGGTG GTGGCGGCTC GATCATGGCC
      CTCAGCCGTG AAGACCCGTA AGGGTCCCAC CACCGCCGAG CTAGTACCGG

                        Cutinase
      ~~~~~~~~~~~~~~~~~~~~~~~~~~~~~~~~~~~~~~~~~~~~~~~~~~~~
       G  Q  D  T   R  V  R   T  T  A   P  I  Q  P   Y  T  L ·
1101  GGGCAGGATA CGAGGGTGCG TACCACGGCG CCGATCCAGC CCTACACCCT
      CCCGTCCTAT GCTCCCACGC ATGGTGCCGC GGCTAGGTCG GGATGTGGGA

                        Cutinase
```

FIGURE 8 (cont.)

```
          ~~~~~~~~~~~~~~~~~~~~~~~~~~~~~~~~~~~~~~~~~~~~~~~~~~~~~~~
          ·G  L  G   H  D  S  A   S  Q  R   R  Q  Q   G  P  M  F·
1151      CGGCCTGGGG CACGACAGCG CCTCGCAGCG GCGGCAGCAG GGGCCGATGT
          GCCGGACCCC GTGCTGTCGC GGAGCGTCGC CGCCGTCGTC CCCGGCTACA

                                  Cutinase
          ~~~~~~~~~~~~~~~~~~~~~~~~~~~~~~~~~~~~~~~~~~~~~~~~~~~~~~~
          · L  M  S   G  G  G   D  T  I  A   F  P  Y   L  N  A
1201      TCCTGATGTC CGGTGGCGGT GACACCATCG CCTTTCCCTA CCTCAACGCT
          AGGACTACAG GCCACCGCCA CTGTGGTAGC GGAAAGGGAT GGAGTTGCGA

                                  Cutinase
          ~~~~~~~~~~~~~~~~~~~~~~~~~~~~~~~~~~~~~~~~~~~~~~~~~~~~~~~
           Q  P  V  Y   R  R  A   N  V  P   V  F  W  G   E  R  R·
1251      CAGCCGGTCT ACCGGCGTGC CAATGTGCCG GTGTTCTGGG GCGAACGGCG
          GTCGGCCAGA TGGCCGCACG GTTACACGGC CACAAGACCC CGCTTGCCGC

                                  Cutinase
          ~~~~~~~~~~~~~~~~~~~~~~~~~~~~~~~~~~~~~~~~~~~~~~~~~~~~~~~
          ·Y  V  S   H  F  E  P   V  G  S   G  G  A   Y  R  G  P·
1301      TTACGTCAGC CACTTCGAGC CGGTCGGTAG CGGTGGGGCC TATCGCGGCC
          AATGCAGTCG GTGAAGCTCG GCCAGCCATC GCCACCCCGG ATAGCGCCGG

                                  Cutinase
          ~~~~~~~~~~~~~~~~~~~~~~~~~~~~~~~~~~~~~~~~~~~~~~~~~~~~~~~
          · S  T  A   W  F  R   F  Q  L  M   D  D  Q   D  A  R
1351      CGAGCACGGC ATGGTTCCGC TTCCAGCTGA TGGATGACCA AGACGCCCGC
          GCTCGTGCCG TACCAAGGCG AAGGTCGACT ACCTACTGGT TCTGCGGGCG

                                  Cutinase
          ~~~~~~~~~~~~~~~~~~~~~~~~~~~~~~~~~~~~~~~~~~~~~~~~~~~~~~~
                                            Alw44I
                                            ~~~~~~~
           A  T  F  Y   G  A  Q   C  S  L   C  T  S  L   L  W  S·
1401      GCTACCTTCT ACGGCGCGCA GTGCAGTCTG TGCACTTCTC TGCTTTGGTC
          CGATGGAAGA TGCCGCGCGT CACGTCAGAC ACGTGAAGAG ACGAAACCAG

                                        Linker 2
                                ~~~~~~~~~~~~~~~~~~~~~~~~~~~~~
               Cutinase
          ~~~~~~~~~~~~~~~~~~~~
                                                 BamHI
                                                 ~~~~~~~
          ·V  E  R   R  G  L  D   N  N  D   P  I  P  D             (SEQ ID NO:7)
1451      TGTTGAACGC AGAGGTCTTG ACAACAATGA TCCTATTCCG GATCC         (SEQ ID NO:8)
        ACAACTTGCG TCTCCAGAAC TGTTGTTACT AGGATAAGGC CTAGG
```

BACTERIAL EXPRESSION OF BOWMAN-BIRK PROTEASE INHIBITORS AND VARIANTS THEREOF

The present application claims priority under 35 U.S.C. § 119, to co-pending U.S. Provisional Patent Application Ser. No. 60/518,154, filed Nov. 6, 2003, co-pending U.S. Provisional Patent Application Ser. No. 60/520,403, filed Nov. 13, 2003, co-pending U.S. Provisional Patent Application Ser. No. 60/530,954, filed Dec. 19, 2003, co-pending U.S. Provisional Patent Application Ser. No. 60/531,207, filed Dec. 19, 2003, and co-pending U.S. Provisional Patent Application Ser. No. 60/531,189, filed Dec. 19, 2003.

FIELD OF THE INVENTION

The present invention provides compositions and methods related to expression of protease inhibitors and variants thereof in bacterial species. The present invention further provides fusion nucleic acids, vectors, fusion polypeptides, and processes for obtaining the protease inhibitors.

BACKGROUND OF THE INVENTION

Proteases are involved in a wide variety of biological processes. Disruption of the balance between proteases and protease inhibitors is often associated with pathologic tissue destruction. Indeed, various studies have focused on the role of proteases in tissue injury, and it is thought that the balance between proteases and protease inhibitors is a major determinant in maintaining tissue integrity. Serine proteases from inflammatory cells, including neutrophils, are implicated in various inflammatory disorders, such as pulmonary emphysema, arthritis, atopic dermatitis and psoriasis.

Proteases also appear to function in the spread of certain cancers. Normal cells exist in contact with a complex protein network, called the extracellular matrix (ECM). The ECM is a barrier to cell movement and cancer cells must devise ways to break their attachments, degrade, and move through the ECM in order to metastasize. Proteases are enzymes that degrade other proteins and have long been thought to aid in freeing the tumor cells from their original location by chewing up the ECM. Recent studies have suggested that they may promote cell shape changes and motility through the activation of a protein in the tumor cell membrane called Protease-Activated Receptor-2 (PAR2). This leads to a cascade of intracellular reactions that activates the motility apparatus of the cell. Thus, it is hypothesized that one of the first steps in tumor metastasis is a reorganization of the cell shape, such that it forms a distinct protrusion at one edge facing the direction of migration. The cell then migrates through a blood vessel wall and travels to distal locations, eventually reattaching and forming a metastatic tumor. For example, human prostatic epithelial cells constitutively secrete prostate-specific antigen (PSA), a kallikrein-like serine protease, which is a normal component of the seminal plasma. The protease acts to degrade the extracellular matrix and facilitate invasion of cancerous cells.

Synthetic and natural protease inhibitors have been shown to inhibit tumor promotion in vivo and in vitro. Previous investigations have indicated that certain protease inhibitors belonging to a family of structurally-related proteins classified as serine protease inhibitors or SERPINS, are known to inhibit several proteases including trypsin, cathepsin G, thrombin, and tissue kallikrein, as well as neutrophil elastase. The SERPINS are extremely effective at preventing/suppressing carcinogen-induced transformation in vitro and carcinogenesis in animal model systems. Systemic delivery of purified protease inhibitors apparently reduces joint inflammation and cartilage and bone destruction as well.

Topical administration of protease inhibitors finds use in such conditions as atopic dermatitis, a common form of inflammation of the skin, which may be localized to a few patches or involve large portions of the body. The depigmenting activity of protease inhibitors and their capability to prevent ultraviolet-induced pigmentation have been demonstrated both in vitro and in vivo (See e.g., Paine et al., J. Invest. Dermatol., 116:587-595 [2001]). Protease inhibitors have also been reported to facilitate wound healing. For example, secretory leukocyte protease inhibitor was demonstrated to reverse the tissue destruction and speed the wound healing process when topically applied. In addition, serine protease inhibitors can also help to reduce pain in lupus erythematosus patients (See e.g., U.S. Pat. No. 6,537,968).

As noted above, protease inhibitors interfere with the action of proteases. Naturally occurring protease inhibitors can be found in a variety of foods such as cereal grains (oats, barley, and maize), Brussels sprouts, onion, beetroot, wheat, finger millet, and peanuts. One source of interest is the soybean. The average level of protease inhibitors present in soybeans is around 1.4 percent and 0.6 percent for Kunitz and Bowman-Birk respectively, two of the most important protease inhibitors. Notably, these low levels make it impractical to isolate the natural protease inhibitor for clinical applications.

Thus, there is a need for methods and compositions suitable for the large-scale production of protease inhibitors and their variants. In particular, there remains a need for compositions and methods that reduce and/or eliminate risks associated with blood-borne infectious agents when these proteases are produced in mammalian tissue culture cells.

SUMMARY OF THE INVENTION

The present invention provides compositions and methods related to expression of protease inhibitors and variants thereof in bacterial species. The present invention further provides fusion nucleic acids, vectors, fusion polypeptides, and processes for obtaining the protease inhibitors.

Provided herein are nucleic acids, cells and methods for the production of protease inhibitors and variants thereof.

The present invention provides nucleic acids encoding at least one functional protease inhibitor. In one aspect, a nucleic acid comprising regulatory sequences operatively linked to a first, second, third and fourth nucleic acid sequences are provided. In some embodiments, terminator sequences are provided following the fourth nucleic acid sequence.

In alternative embodiments, the first nucleic acid sequence encodes a signal polypeptide functional as a secretory sequence in a first host organism, the second nucleic acid encodes a secreted polypeptide or functional portion thereof normally secreted from the first or a second host organism, the third nucleic acid encodes a cleavable linker and the fourth nucleic acid encodes a protease inhibitor or fragment thereof. In further embodiments, the present invention provides at least one expression cassette comprising nucleic acid sequences encoding at least one protease inhibitor.

In additional embodiments, the present invention provides polynucleotides encoding at least one protease inhibitor variant. In some particularly preferred embodiments, the polynucleotide encodes a Bowman-Birk Inhibitor (BBI) variant, wherein at least one loop of the wild-type BBI has been altered.

The present invention also provides methods of expressing functional protease inhibitors or variants thereof. In some preferred embodiments, host cells suitable for production of functional protease inhibitors and/or variants thereof are provided. In some embodiments, a host cell is (i) transformed with at least one expression cassette comprising a nucleic acid sequence encoding at least one protease inhibitor or variant thereof, and (ii) cultured under appropriate conditions to express at least one protease inhibitor or variants thereof. In some embodiments of the methods, the method further comprises recovering the protease inhibitor or variant thereof.

In alternative embodiments, a host cell is (i) transformed with a first expression cassette comprising at least one nucleic acid sequence encoding a protease inhibitor or variant thereof, (ii) transformed with a second expression cassette comprising a nucleic acid sequence encoding at least one thiol-disulfide oxidoreductase or chaperone, and (iii) cultured under appropriate conditions to express the protease inhibitors or variant thereof. In some embodiments, the protease inhibitors or variants thereof are recovered. In some preferred embodiments, the protease inhibitors or variant thereof are expressed as a fusion protein. In further embodiments, the methods further comprise recovering the protease inhibitor or variant thereof.

In still further embodiments, functional protease inhibitors and variants thereof are provided. In some embodiments, the functional protease inhibitor or variant thereof is expressed as a fusion protein consisting of the signal sequence, a cellulase catalytic domain, a cleavable linker region, and then by the mature protease inhibitor or variant thereof.

In additional embodiments, the expressed proteins are treated with a protease and/or acid/heat treatment to liberate a protease inhibitor or variant thereof from the fusion protein.

In further embodiments, the present invention provides a polypeptide having protease inhibitory activity, selected from the group consisting of a) Bowman-Birk Inhibitor variants;

b) Bowman-Birk Inhibitor; and c) A scaffold comprising at least one variant sequence.

The present invention provides compositions comprising a fusion protein, wherein the fusion protein comprises a protease inhibitor, and a peptide of interest. In some embodiments, the fusion protein comprises an amino acid selected from the group consisting of SEQ ID NOS:2, 4, 6 and 8. In alternative embodiments, the fusion protein is encoded by a nucleotide sequence selected from the group consisting of SEQ ID NOS:1, 3, 5, and 7. In some preferred embodiments, the protease inhibitor is selected from the group consisting of Bowman-Birk inhibitor (BBI), soybean trypsin inhibitor (STI), and eglin C. In some particularly preferred embodiments, the protease inhibitor is BBI, and wherein the BBI comprises at least one loop selected from the group consisting of a trypsin loop and a chymotrypsin loop. In further preferred embodiments, the protease inhibitor is a scaffold for the peptide of interest. In some preferred embodiments, the loop comprises at least one peptide of interest. In some particularly preferred embodiments, the peptide of interest comprises the amino acid sequence set forth in SEQ ID NO:9. In some more preferred embodiments, the fusion protein comprises the amino acid sequence set forth in SEQ ID NO:4.

The present invention also provides methods for producing at least one protease inhibitor in a bacterial cell comprising: a) introducing a DNA construct into a bacterial cell, wherein the DNA construct comprises a heterologous DNA sequence encoding a protease inhibitor derived from a Bowman-Birk Inhibitor (BBI) or variants thereof; b) culturing the bacterial cell under suitable culture conditions to allow expression of the heterologous DNA sequence; and c) producing the protease inhibitor. In some embodiments, the construct further comprises at least one catalytic domain. In some embodiments, catalytic domain is selected from the group consisting of cellulase, cutinase, and disulfide isomerase. In some preferred embodiments, the method further comprises the step of recovering the protease inhibitor. In some particularly preferred embodiments, the method further comprises the step of activating the protease inhibitor. In some most preferred embodiments, the activating is accomplished by exposing the protease inhibitor to at least one reagent selected from the group consisting of compositions that reduce disulfide bonds, compositions that oxidize disulfide bonds, and compositions that alter the redox potential. In some embodiments, the bacterial cell is a member of the genus *Bacillus*. In additional embodiments, protease inhibitor is selected from the group consisting of: i) a protease inhibitor having at least 90% sequence identity with SEQ ID NO: 11; and ii) a protease inhibitor having at least 90% sequence identity with SEQ ID NO:13. In yet further embodiments, the protease inhibitor comprises a variant sequence. In additional embodiments, the protease inhibitor is Bowman-Birk inhibitor and wherein SEQ ID NO:9 is substituted for at least one loop, wherein the loop is selected from the group consisting of the trypsin loop and the chymotrypsin loop. In some embodiments, the method further comprises the step of introducing a second nucleic acid sequence encoding a thiol-disulfide oxidoreductase or chaperone into the bacterial cell. In some preferred embodiments, the protease inhibitor is expressed as a fusion protein. In some preferred embodiments, the fusion protein further comprises a cellulase catalytic domain, a cleavage site, and the protease inhibitor. In some particularly preferred embodiments, the fusion protein is processed by a protease or acid/heat treatment to liberate the protease inhibitor. In still further preferred embodiments, the fusion protein further comprises at least one linker sequence. In some embodiments, the linker sequence is selected from the group consisting of SEQ ID NOS:141-143.

The present invention also provides protease inhibitor compositions comprising the protease inhibitor produced according to any and all of the methods described herein. In some embodiments, the various primers and oligonucleotides described herein find use in the production of the fusion proteins of the present invention. In addition, the present invention provides numerous peptides suitable for use in the present invention.

The present invention also provides methods for inhibiting the proteolytic activity of a target protein comprising contacting the target protein with any of the protease inhibitor compositions described herein, and binding the target protein wherein the proteolytic activity of the target protein is inhibited.

The present invention further provides isolated polynucleotides encoding a protease inhibitor selected from the group consisting of polypeptide sequences set forth in SEQ ID NOS:10 and 12.

The present invention also provides expression vectors comprising a polynucleotide sequence, wherein the polynucleotide sequence is selected from the following: a) a polynucleotide sequence encoding a protease inhibitor having at least 90% sequence identity with SEQ ID NO: 11, wherein at least one of the loop residues have been replaced with a variant sequence; and b) a polynucleotide sequence encoding a protease inhibitor having at least 90% sequence identity with SEQ ID NO: 13, wherein at least one of the loop residues have been replaced with a variant sequence. In some embodiments, the expression vectors further comprise from the 5' terminus to the 3' terminus: a first nucleic acid sequence encoding a signal peptide functional as a secretory sequence in a bacterial cell; a second nucleic acid sequence encoding a secreted polypetide or functional portion thereof; a third nucleic acid sequence encoding a cleavable linker; and the DNA sequence which encodes the protease inhibitor. The present invention also provides host cells transformed with the expression vectors of the present invention. In some preferred embodiments, the host cell is a *Bacillus* species cell.

The present invention also provides compositions comprising at least one scaffold protein and at least one peptide, wherein the scaffold comprises Bowman-Birk inhibitor. In some preferred embodiments, the peptide comprises a peptide that binds to VegF.

Other objects, features and advantages of the present invention are apparent from the following detailed description. It should be understood, however, that the detailed description and specific examples, while indicating preferred embodiments of the invention, are given by way of illustration only, since various changes and modifications within the scope and spirit of the invention will be apparent to those skilled in the art from this detailed description.

BRIEF DESCRIPTION OF THE DRAWINGS

FIG. 1 provides the DNA and amino acid sequences of the aprE-BCE103-BBI-Histag expression cassette (EcoRI-HindIII) cloned into the pJM103 integration vector (SEQ ID NOS:1 and 2).

FIG. 3 provides the DNA and amino acid sequences of 12BBIck81 from the BCE103 fusion site (at the BamHI) to the end of the gene (SEQ ID NOS:3 and 4). The CK37281 peptide sequences (ACYNLYGWTC (SEQ ID NO:9) are inserted into both the trypsin and chymotrypsin inhibitory loops.

FIG. 7 provides the sequence of the synthetic DNA fragment carrying the *H. insolens* PDI (hiPDI) that was inserted into the *B. subtilis* BBI expression vector, as well as the amino acid sequence (SEQ ID NOS:5 and 6)

FIG. 8 provides the DNA and amino acid sequences of the aprE-cutinase expression cassette that was ligated into the EcoRI-BamHI sites of p2JM103-lnk2-2BBIck81 (SEQ ID NOS:7 and 8).

DESCRIPTION OF THE INVENTION

Figure 2:
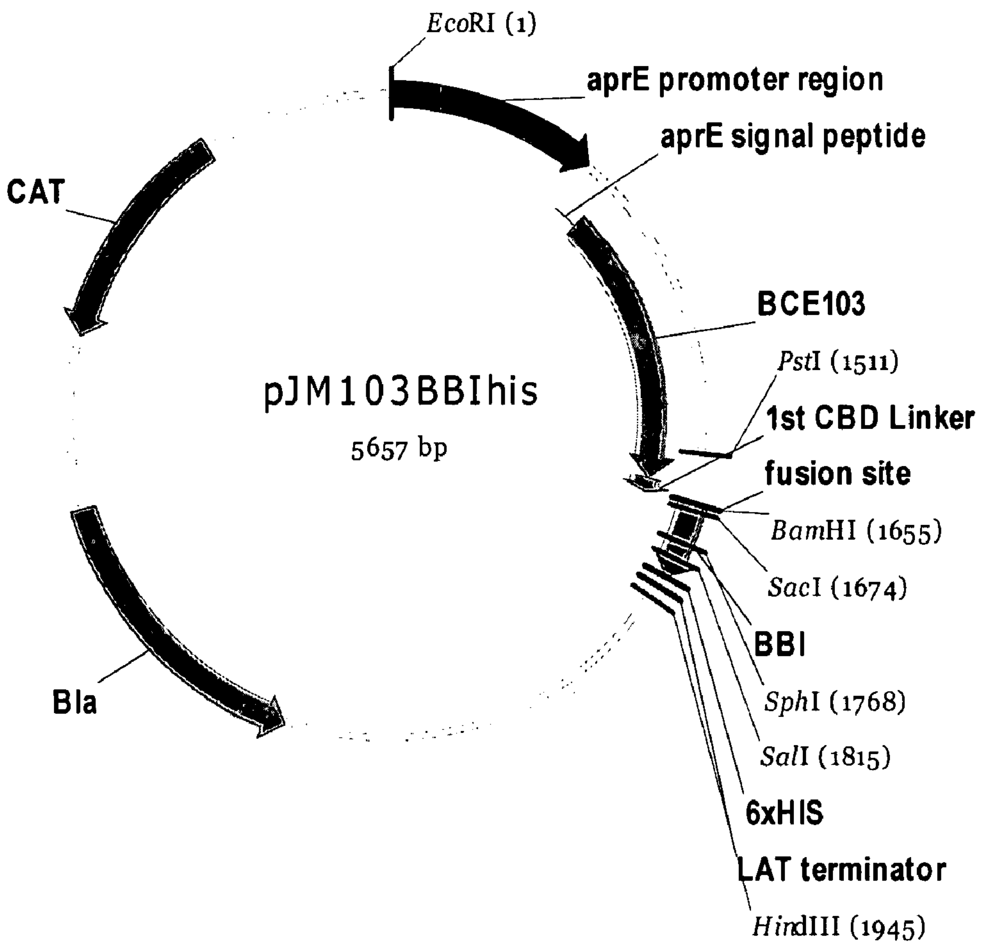
FIG. 2 provides a schematic map of the pJM103BBIhis expression vector.

The present invention provides compositions and methods related to expression of protease inhibitors and variants thereof in bacterial species. The present invention further provides fusion nucleic acids, vectors, fusion polypeptides, and processes for obtaining the protease inhibitors.

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works (See e.g., Sambrook et al., “Molecular Cloning: A Laboratory Manual”, Second Edition (Cold Spring Harbor), [1989]); and Ausubel et al., “Current Protocols in Molecular Biology” [1987]). All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology,* 2d Ed., John Wiley and Sons, NY (1994); and Hale and Marham, *The Harper Collins Dictionary of Biology*, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular “a”, “an” and “the” includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

Definitions

As used herein, the terms “expression cassette” and “expression vector” refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. The term “expression cassette” may be used interchangeably herein with “DNA construct” and its grammatical equivalents.

As used herein, the terms “vector” and “cloning vector” refer to nucleic acid constructs designed to transfer nucleic acid sequences into cells.

As used herein, the term “expression vector” refers to a vector that has the ability to incorporate and express heterologous DNA fragments in a foreign cell. Many prokaryotic and eukaryotic expression vectors are commercially available. Selection of appropriate expression vectors is within the knowledge of those of skill in the art.

As used herein, the term “plasmid” refers to a circular double-stranded (ds) DNA construct used as a cloning vector, and which forms an extrachromosomal self-replicating genetic element in some eukaryotes or prokaryotes, or integrates into the host chromosome.

As used herein, the terms "nucleic acid molecule" and "nucleic acid sequence" include sequences of any form of nucleic acid, including, but not limited to RNA, DNA and cDNA molecules. It will be understood that, as a result of the degeneracy of the genetic code, a multitude of nucleotide sequences encoding a given protein may be produced.

As used herein, a "fusion DNA sequence" comprises from 5' to 3' a first, second, third and fourth DNA sequences.

As used herein, "a first nucleic acid sequence" or "first DNA sequence" encodes a signal peptide functional as a secretory sequence in bacterial species. Particularly preferred signal sequences are those derived from polypeptides secreted by the expression host used to express and secrete the fusion polypeptide. As used herein, first amino acid sequences correspond to secretory sequences which are functional in a bacterial species. Such amino acid sequences are encoded by first DNA sequences as defined.

As used herein, "second DNA sequences" encode "secreted polypeptides" (i.e., "secreted polypeptides of interest") expressed by the chosen bacterial species. As with the first DNA sequences, preferred secreted polypeptides are those which are naturally secreted by the bacterial expression host. However, in some embodiments, the term refers to heterologous protein (i.e., proteins that are not normally secreted by the particular bacterial host). For example, in some preferred embodiments, a cellulase expressed by a *Bacillus* species other than *B. subtilis* is used that the secreted polypeptide of interest and *B. subtilis* is used as the expression host.

As used herein, "functional portion of a secreted polypeptide" and its grammatical equivalents refers to a truncated secreted polypeptide that retains its ability to fold into a normal, albeit truncated, configuration. In some embodiments, it is contemplated that sufficient residues of a domain of the secreted polypeptide must be present to allow it to fold in its normal configuration independently of the desired polypeptide to which it is attached. However, in most cases, the portion of the secreted polypeptide are both correctly folded and result in increased secretion as compared to its absence.

Similarly, in most cases, the truncation of the secreted polypeptide means that the functional portion retains a biological function. In a preferred embodiment, the catalytic domain of a secreted polypeptide is used, although other functional domains may be used, for example, the substrate binding domains. Additionally preferred embodiments utilize the catalytic domain and all or part of the linker region.

As used herein, "third DNA sequences" comprise DNA sequences encoding a cleavable linker polypeptide. It should be understood that the third DNA sequence need only encode that amino acid sequence which is necessary to be recognized by a particular enzyme or chemical agent to bring about cleavage of the fusion polypeptide. Thus, only that portion of the linker which is necessary for recognition and cleavage by the appropriate enzyme is required.

As used herein, "fourth DNA sequences" encode "desired polypeptides." Such desired polypeptides include protease inhibitors either in their mature or pro forms, and variants thereof.

The above-defined four DNA sequences encoding the corresponding four amino acid sequences are combined to form a "fusion DNA sequence." Such fusion DNA sequences are assembled in proper reading frame from the 5' terminus to 3' terminus in the order of first, second, third and fourth DNA sequences. As so assembled, the DNA sequence encodes a "fusion polypeptide," "fusion protein," and "fusion analog" encoding from its amino-terminus a signal peptide functional as a secretory sequence in a bacterial species, a secreted polypeptide or portion thereof normally secreted by a bacterial species, a cleavable linker polypeptide and a desired polypeptide.

As used herein, the terms "desired protein" and "desired polypeptide" refer to a polypeptide or protein in its mature or pro form that is not fused to a secretion enhancing construct. Thus, a "desired protein" and "desired polypeptide" refer to the protein to be expressed and secreted by the host cell in a non-fused form.

As used herein, "fusion polypeptides," "fusion proteins," and "fusion analogs" encode from the amino-terminus a signal peptide functional as a secretory sequence functional in a host cell, a secreted polypeptide or portion thereof normally secreted from a host cell, a cleavable linker polypeptide and a desired polypeptide. In some embodiments, the fusion protein is processed by host cell enzymes (e.g., a protease), to yield the desired protein free from the other protein sequences in the fusion protein. As used herein, the terms "fusion analog," "fusion polypeptide," and "fusion protein" are used interchangeably.

As used herein, a "promoter sequence" refers to a DNA sequence which is recognized by the bacterial host for expression purposes. In preferred embodiments, it is operably linked to a DNA sequence encoding the fusion polypeptide. Such linkage comprises positioning of the promoter with respect to the translation initiation codon of the DNA sequence encoding the fusion DNA sequence. In particularly preferred embodiments, the promoter sequence contains transcription and translation control sequences which mediate the expression of the fusion DNA sequence.

As used herein, "terminator sequence" refers to a DNA sequence which is recognized by the expression host to terminate transcription. It is operably linked to the 3' end of the fusion DNA encoding the fusion polypeptide to be expressed.

As used herein, the term "selectable marker-encoding nucleotide sequence" refers to a nucleotide sequence which is capable of expression in bacterial cells and where expression of the selectable marker confers to cells containing the expressed gene the ability to grow in the presence of a corresponding selective condition.

As used herein, a nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Operably linked DNA sequences are usually contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "expression" refers to the process by which a polypeptide is produced based on the nucleic acid sequence of a gene. The process includes both transcription and translation. Thus, the term "protease inhibitor expression" refers to transcription and translation of the specific protease inhibitors and variants thereof gene to be expressed, the products of which include precursor RNA, mRNA, polypeptide, post-translation processed polypeptide, and derivatives thereof. Similarly, "protease inhibitor expression" refers to the transcription, translation and assembly of protease inhibitors and variants thereof exemplified by the expression cassette shown in FIG. 1. By way of example, assays for protease inhibitor expression include examination of bacterial colonies when exposed to the appropriate conditions, Western blots for protease inhibitor protein, as well as Northern blots analysis and reverse transcriptase polymerase chain reaction (RT-PCR) assays for protease inhibitor mRNA.

As used herein, the terms "isolated" and "purified" as used herein refer to a nucleic acid or polypeptide that is removed from at least one component with which it is naturally associated.

As used herein, the term "substantially free" encompasses preparations of the desired polypeptide having less than about 20% (by dry weight) other proteins (i.e., contaminating protein), less than about 10% other proteins, less than about 5% other proteins, or less than about 1% other proteins.

As used herein, the term "substantially pure" when applied to the proteins or fragments thereof of the present invention means that the proteins are essentially free of other substances to an extent practical and appropriate for their intended use. In particular, the proteins are sufficiently pure and are sufficiently free from other biological constituents of the host cells so as to be useful in, for example, protein sequencing, and/or producing pharmaceutical preparations.

As used herein, the term "target protein" refers to protein (e.g., enzyme, hormone, etc.), whose action would be blocked by the binding of the variant inhibitors provided for herein.

As used herein, the terms "variant sequence" and "variant sequences" refer to the short polypeptide sequence(s) that replace the binding loops of the wild-type protease inhibitor or other scaffold. The variant sequence does not need to be of the same length as the binding loop sequence it is replacing in the scaffold.

As used herein, the term "scaffold" refers to a wild-type protein sequence into which a variant sequence is introduced. In some embodiments, the scaffold has portions (e.g., loops), that are replaced. For example, the BBI sequences provided herein find use as scaffolds for variant sequences.

Protease Inhibitors

Two protein protease inhibitors have been isolated from soybeans, the Kunitz-type trypsin inhibitor (soybean trypsin inhibitor, STI) and the Bowman-Birk protease inhibitor (BBI) (See e.g., Birk, Int. J. Pept. Protein Res., 25:113-131 [1985]; and Kennedy, Am. J. Clin. Neutr., 68:1406S-1412S [1998]). These inhibitors serve as a scaffold for the variant sequences. In addition to alterations in the scaffold comprising the variant sequences, other desired proteins used herein include the addition of six histidine residues at the C-terminus (See, FIGS. 1 and 2).

Soybean Trypsin Inhibitor (STI)

STI inhibits the proteolytic activity of trypsin by the formation of a stable stoichiometric complex (See e.g., Liu, Chemistry and Nutritional Value of Soybean Components, In: *Soybeans, Chemistry Technology and Utilization*, pp. 32-35, Aspen Publishers, Inc., Gaithersburg, Md., [1999]). STI consists of 181 amino acid residues with two disulfide bridges and is roughly spherically shaped (See e.g., Song et al., J. Mol. Biol., 275:347-63 [1998]). The trypsin inhibitory loop lies within the first disulfide bridge. The Kunitz-type soybean trypsin inhibitor (STI) has played a key role in the early study of proteinases, having been used as the main substrate in the biochemical and kinetic work that led to the definition of the standard mechanism of action of proteinase inhibitors.

Bowman-Birk Inhibitor (BBI)

Bowman-Birk inhibitor proteins are a kinetically and structurally well-characterized family of small proteins (60-90 residues) isolated from leguminous seeds, as well as other plants, including various grasses. They typically have a symmetrical structure of two tricyclic domains each containing an independent binding loop, although some have one domain and some have more than two domains. The major ~8 kDa Bowman-Birk inhibitor isolated from soybeans (BBI) has two separate reactive site loops, loop I inhibits proteases having trypsin-like specificity and loop II inhibits proteases with chymotrypsin-like specificity (See e.g., Chen et al., J. Biol. Chem., 267:1990-1994 [1992]; Werner and Wemmer, Biochem., 31:999-1010 [1992]; Lin et al., Eur. J. Biochem., 212:549-555 [1993]; Voss et al., Eur. J. Biochem., 242:122-131 [1996]; and Billings et al., Pro. Natl. Acad. Sci., 89:3120-3124 [1992]). These binding regions each contain a "canonical loop" structure, which is a motif found in a variety of serine proteinase inhibitors (Bode and Huber, Eur. J. Biochem., 204:433-451 [1992]). STI and BBI are found only in the soybean seed, and not in any other part of the plant (See e.g., Birk, Int. J. Pept. Protein Res., 25:113-131 [1985]).

Although numerous isoforms of BBI have been characterized, SEQ ID NO:13 shows the amino acid sequence of the BBI backbone used herein comprising approximately 71 amino acid residues (See Example 1).

In soybeans, BBI is produced as a pro-protein with an N-terminal pro-peptide that is 19 amino acids in length. Thus, in some embodiments, BBI is produced with all or at least a portion of the propeptide. In some embodiments, BBI is truncated, with as many as 10 amino acid residues being removed from either the N- or C-terminal. For example, upon seed desiccation, some BBI molecules have the C-terminal 9 or 10 amino acid residues removed. Thus, proteolysis is generally highly tolerated prior to the initial disulfide and just after the terminal disulfide bond, the consequences of which are usually not detrimental to the binding to target protein. However, it will be appreciated that any one of the isoforms or truncated forms find use in various embodiments of the present invention.

Protease Inhibitor Variants

As indicated above, the STI and BBI protease inhibitors have binding loops that inhibit proteases. The present invention provides protease inhibitor variants with alterations in one or more reactive sites (e.g., Loop I and/or Loop II of BBI). In some preferred embodiments, the loops are replaced with sequences that interact with a target protein.

For example, in some embodiments, the loops are replaced with sequences derived from VEGF binding proteins, inhibitors of the complement pathway such as C2, C3, C4 or C5 inhibitors, Compstatin, cytokines, other proteins of interest, etc. Indeed, it is not intended that the present invention be limited to any particular sequence substituted into either of these loops, as any suitable sequence finds use in the present invention.

In some embodiments, variant sequences are selected by various methods known in the art, including but not limited to phage display and other suitable screening methods. For example, a random peptide gene library is fused with phage PIII gene so the peptide library will be displayed on the surface of the phage. Subsequently, the phage display library is exposed to the target protein and washed with buffer to remove non-specific binding (this process is sometimes referred to as panning). Finally, the binding phage and PCR the DNA sequence for the peptide encoded are isolated.

In most embodiments, one of the loops is replaced with a variant sequence (i.e., peptides; often 3 to 14 amino acids in length, with 5 to 10 amino acids being preferred). Longer sequences find use in the present invention, as long as they provide the binding and/or inhibition desired. In addition, peptides suitable for use as replacements of the binding loop(s) preferably adopt a functional conformation when contained within a constrained loop (i.e., a loop formed by the presence of a disulfide bond between two cysteine residues). In some specific embodiments, the peptides are between 7 and 9 amino acids in length. These replacement sequences also provide protease inhibition or binding to the targeted proteins. In some embodiments, it is advantages to alter a single amino acid.

Fusion Proteins

In preferred embodiments, each protease inhibitor or variant thereof is expressed as a fusion protein by the host bacterial cell. Although cleavage of the fusion polypeptide to release the desired protein will often be useful, it is not necessary. Protease inhibitors and variants thereof expressed and secreted as fusion proteins surprisingly retain their function.

The above-defined DNA sequences encoding the corresponding amino acid sequences are combined to form a "fusion DNA sequence." Such fusion DNA sequences are assembled in proper reading frame from the 5' terminus to 3' terminus in the order of first, second, third and fourth DNA sequences. As so assembled, the DNA sequence encodes a "fusion polypeptide" encoding from its amino-terminus a signal peptide functional as a secretory sequence in a bacterial species, a secreted polypeptide or portion thereof normally secreted from a bacterial species, a cleavable linker peptide and a desired polypeptide (e.g., a protease inhibitor and variants thereof). Various methods are known to those in the art for the production of fusion proteins (See e.g., U.S. Pat. Nos. 5,411,873, 5,429,950, and 5,679,543, all of which are incorporated by reference herein). Thus, it is intended that any suitable method will find use in the present invention.

Expression of Recombinant Protease Inhibitors

To the extent that the present invention depends on the production of fusion proteins, it relies on routine techniques in the field of recombinant genetics. Basic texts disclosing the general methods of use in this invention include Sambrook et al., *Molecular Cloning, A Laboratory Manual* ((2nd ed.) [1989]); Kriegler, *Gene Transfer and Expression: A Laboratory Manual* (1990); and Ausubel et al., (eds.), *Current Protocols in Molecular Biology* (1994).

The present invention provides bacterial host cells which have been transduced, transformed or transfected with an expression vector comprising a protease inhibitor-encoding nucleic acid sequence. The culture conditions, such as temperature, pH and the like, are those previously used for the parental host cell prior to transduction, transformation or transfection are apparent to those skilled in the art.

Basically, a nucleotide sequence encoding a fusion protein is operably linked to a promoter sequence functional in the host cell. This promoter-gene unit is then typically cloned into intermediate vectors before transformation into the host cells for replication and/or expression. These intermediate vectors are typically prokaryotic vectors (e.g., plasmids, or shuttle vectors). However, it is not intended that the present invention be limited to the use of intermediate vectors, as this step is omitted in some preferred embodiments.

In one approach, a bacterial culture is transformed with an expression vector having a promoter or biologically active promoter fragment or one or more (e.g., a series) of enhancers which functions in the host cell, operably linked to a nucleic acid sequence encoding a protease inhibitor, such that the a protease is expressed in the cell. In some preferred embodiments, the DNA sequences encode a protease inhibitor or variant thereof. In another preferred embodiment, the promoter is a regulatable one.

Nucleic Acid Constructs/Expression Vectors.

Natural or synthetic polynucleotide fragments encoding a protease inhibitor (i.e., "PI-encoding nucleic acid sequences") may be incorporated into heterologous nucleic acid constructs or vectors, capable of introduction into, and replication in, a bacterial cell. The vectors and methods disclosed herein are suitable for use in various host cells for the expression of protease inhibitors and variants thereof. Any vector may be used as long as it is replicable and viable in the cells into which it is introduced. Large numbers of suitable vectors and promoters are known to those of skill in the art, and are commercially available. Appropriate cloning and expression vectors are also described in various references known to those in the art (See e.g., Sambrook et al., supra and Ausubel et al., supra, expressly incorporated by reference herein). The appropriate DNA sequence is inserted into a plasmid or vector (collectively referred to herein as "vectors") by any suitable method. In general, the DNA sequence is inserted into an appropriate restriction endonuclease site(s) by standard procedures known to those in the art.

Appropriate vectors are typically equipped with a selectable marker-encoding nucleic acid sequence, insertion sites, and suitable control elements, such as termination sequences. In some embodiments, the vectors comprise regulatory sequences, including, for example, control elements (i.e., promoter and terminator elements or 5' and/or 3' untranslated regions), effective for expression of the coding sequence in host cells (and/or in a vector or host cell environment in which a modified soluble protein coding sequence is not normally expressed), operably linked to the coding sequence. Large numbers of suitable vectors and promoters are known to those of skill in the art, many of which are commercially available and known to those in the art.

Exemplary promoters include both constitutive promoters and inducible promoters. Such promoters are well known to those of skill in the art. Those skilled in the art are also aware that a natural promoter can be modified by replacement, substitution, addition or elimination of one or more nucleotides without changing its function. The practice of the present invention encompasses and is not constrained by such alterations to the promoter. The choice of promoter used in the genetic construct is within the knowledge of one skilled in the art.

The choice of the proper selectable marker will depend on the host cell. Appropriate markers for different bacterial hosts are well known in the art. Typical selectable marker genes encode proteins that (a) confer resistance to antibiotics or other toxins (e.g., ampicillin, methotrexate, tetracycline, neomycin mycophenolic acid, puromycin, zeomycin, or hygromycin; or (b) complement an auxotrophic mutation or a naturally occurring nutritional deficiency in the host strain.

In some embodiments, a selected PI coding sequence is inserted into a suitable vector according to well-known recombinant techniques and used to transform a cell line capable of PI expression. Due to the inherent degeneracy of the genetic code, other nucleic acid sequences which encode substantially the same or a functionally equivalent amino acid sequence may be used to clone and express a specific protease inhibitor, as further detailed above. Therefore it is appreciated that such substitutions in the coding region fall within the sequence variants covered by the present invention. Any and all of these sequence variants can be utilized in the same way as described herein for a parent PI-encoding nucleic acid sequence. Those skilled in the art recognize that differing PIs will be encoded by differing nucleic acid sequences.

In some embodiments, once the desired form of a protease inhibitor nucleic acid sequence, homologue, variant or fragment thereof, is obtained, it is modified by any number of ways. Where the sequence involves non-coding flanking regions, the flanking regions may be subjected to resection, mutagenesis, etc. Thus, transitions, transversions, deletions, and insertions may be performed on the naturally occurring sequence.

In some preferred embodiments, heterologous nucleic acid constructs include the coding sequence for at least one protease inhibitor, or variant(s), fragment(s) or splice variant(s) thereof: (i) in isolation; (ii) in combination with additional coding sequences; such as fusion protein or signal peptide coding sequences, where the PI coding sequence is the dominant coding sequence; (iii) in combination with non-coding sequences, such as control elements, such as promoter and terminator elements or 5' and/or 3' untranslated regions, effective for expression of the coding sequence in a suitable host; and/or (iv) in a vector or host environment in which the PI coding sequence is a heterologous gene.

In some embodiments, heterologous nucleic acid containing the appropriate nucleic acid coding sequence, together with appropriate promoter and control sequences, is employed to introduced into bacterial host cells to permit the cells to express at least one protease inhibitor or variant thereof.

In some embodiments of the present invention, a heterologous nucleic acid construct is employed to transfer a PI-encoding nucleic acid sequence into a cell in vitro. In some preferred embodiments, the host cells stably integrate the nucleic acid sequences of the present invention. Thus, any suitable method for effectively generating stable transformants finds use in the present invention.

In additional embodiments of the present invention, the first and second expression cassettes are present on a single vector, while in other embodiments these cassettes are present on separate vectors.

In some preferred embodiments, in addition to a promoter sequence, the expression cassette also contains a transcription termination region downstream of the structural gene to provide for efficient termination. In some embodiments, the termination region is obtained from the same gene as the promoter sequence, while in other embodiments it is obtained from another gene. The selection of suitable transcription termination signals is well-known to those of skill in the art.

In addition, it is contemplated that any suitable expression vector will find use in the present invention. Indeed, it is contemplated that various conventional vectors used for expression in eukaryotic or prokaryotic cells will be suitable and find use with the present invention. Standard bacterial expression vectors include bacteriophages λ and M13, as well as plasmids such as pBR322 based plasmids, pSKF, pET23D, and fusion expression systems such as MBP, GST, and LacZ. In further embodiments, epitope tags are added to recombinant proteins, in order to provide convenient methods of isolation (e.g., c-myc).

Additional elements typically included in expression vectors are replicons, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable.

Introduction of a Protease Inhibitor-Encoding Nucleic Acid Sequence into Host Cells.

In some preferred embodiments, the methods of the present invention provide host cells that contain a stably integrated sequence of interest (i.e., PI-encoding nucleic acid). However, in alternative embodiments, the methods of the present invention provide for maintenance of a self-replicating extra-chromosomal transformation vector.

The invention further provides cells and cell compositions which have been genetically modified to comprise an exogenously provided PI-encoding nucleic acid sequence. In some embodiments, a parental host cell is genetically modified by an expression vector. In some embodiments, the vector is a plasmid, while in other embodiments the vector is a viral particle, phage, naked DNA, etc. Thus, it is not intended that the form of the vector be limited to any particular type of vector, as various vectors will find use in the present invention.

Various methods may be employed for delivering an expression vector into cells in vitro. Methods of introducing nucleic acids into cells for expression of heterologous nucleic acid sequences are also known to the ordinarily skilled artisan, including, but not limited to electroporation; protoplast fusion with intact cells; transduction; high velocity bombardment with DNA-coated microprojectiles; infection with modified viral (e.g., phage) nucleic acids; chemically-mediated transformation, competence, etc. In addition, in some embodiments, heterologous nucleic acid constructs comprising a PI-encoding nucleic acid sequence are transcribed in vitro, and the resulting RNA introduced into the host cell by any of the suitable methods known in the art.

Following introduction of a heterologous nucleic acid construct comprising the coding sequence for a protease inhibitor, the genetically modified cells are cultured in conventional nutrient media modified as appropriate for activating promoters, selecting transformants, and/or amplifying expression of a PI-encoding nucleic acid sequence. The culture conditions, such as temperature, pH and the like, are those previously used for the host cell selected for expression, and are apparent to those skilled in the art.

The progeny of cells into which such heterologous nucleic acid constructs have been introduced are generally considered to comprise the PI-encoding nucleic acid sequence found in the heterologous nucleic acid construct.

Bacterial Hosts and Expression

Appropriate host cells include any suitable bacterial species. In some embodiments, the bacterial hosts serve both as the expression hosts and the source of the first and second nucleic acids. Using the present inventive methods and host cells, surprising levels of expression have been obtained. The system utilized herein has achieved levels of expression and secretion of greater than 0.5 g/l of protease inhibitor.

After the expression vector is introduced into the host cells, the transfected host cells are cultured under conditions favoring expression of gene encoding the desired protein. Large batches of transformed cells can be cultured as described above. Finally, product is recovered from the culture using techniques known in the art.

Accessory proteins such as thiol-disulfide oxidoreductases or chaperones find use in some embodiments, as they may be beneficial to help fold the secretory protein into its active conformation. Thiol-disulsfide oxidoreductases and protein disulfide isomerases catalyze the formation of the correct disulfide bonds in the protein. Overexpression of the bdbDC operon in *B. subtilis* has been shown to be beneficial for the production of a protein with disulfide bonds (See e.g., Meima et al., J. Biol. Chem., 277:6994-7001, [2002]). Chaperones help the secretory protein to fold by binding to exposed hydrophobic regions in the unfolded states and preventing unfavourable interactions and prolyl-peptidyl cis-trans isomerases assist in formation of the proper conformation of the peptide chain adjacent to proline residues.

In some embodiments of the present invention, the host cells are transformed with an expression vector encoding at least one thiol-disulfide oxidoreductase or chaperone. It is not intended that the present invention be limited to any particular thiol-disulfide oxidoreductase or chaperone, as any suitable thiol-disulfide oxidoreductase or chaperone known to those skilled in the art will find use in the present invention.

In some embodiments of the present invention, the fraction of properly folded secretory protein is increased by the addition of chemicals to the growth medium that reduce/oxidize disulfide bonds, and/or alter the general redox potential, and/or chemicals that alter solvent properties thus affecting protein conformation and aggregation. In particularly preferred embodiments, a reagent that reduces disulfide bonds, such as 2-mercaptoethanol, is preferred to increase the fraction of correctly folded protein. However, in other embodiments and depending on the medium used, other disulfide reducing or oxidizing agents (e.g., DTT, TCEP, reduced and oxidized glutathione, cysteine, cystine, cysteamine, thioglycolate, $S_2O_3^{2-}$, $S_2O_4^{2-}$, $S_2O_5^{2-}$, $SO_3^{2-}$, $S_2O_7^{2-}$, Cu+, ect.), either used alone or in combination, find use in the present invention. It is contemplated that other adjuvants that alter solvent properties, (e.g., urea, DMSO, TWEEN®-80, etc.), either added to the growth medium alone or preferably in combination with disulfide reducing/oxidizing agents, such as βME, will also increase the fraction of correctly folded secretory protein and find use in various embodiments of the present invention. In some preferred embodiments, the βME is used at concentrations ranging from 0.5 to 4 mM, while in other embodiments, the concentrations range from 0.1 mM to 10 mM. Indeed, those of skill in the art know how to select the best growth medium and growth conditions to optimize the effects of the added thiol reducing/oxidizing agents and/or other adjuvants, as well as the concentration of thio reducing/oxidizing agents and/or other adjuvants to use. It is not intended that the present invention be limited to any particular disulfide reducing/oxidizing agent or adjuvant, as any suitable reagents known to those skilled in the art find use in the present invention.

Fermentation Parameters

The present invention relies on fermentation procedures for culturing bacterial species. Fermentation procedures for production of heterologous proteins by bacterial species are well known in the art. Culturing is accomplished in a growth medium comprising an aqueous mineral salts medium, organic growth factors, the carbon and energy source material, molecular oxygen (for aerobic and facultative bacteria), and, of course, a starting inoculum of one or more particular microorganism species to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation medium.

Various culture media find use in the present invention, as known to those of skill in the art. However, standard bacterial culture media find use in the present invention. In some preferred media formulations, the media include, in addition to nitrogen, suitable amounts of phosphorus, magnesium, calcium, potassium, sulfur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

In some embodiments, the fermentation reaction involves an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species to grow in a thriving fashion. In effect, by using an oxygenated hydrocarbon substrate, the oxygen requirement for growth of the microorganism is reduced. Nevertheless, molecular oxygen must be supplied for growth of aerobic and to a lesser extent, facultative organisms.

Although the aeration rate can vary over a considerable range, aeration generally is conducted at a rate which is in the range of about 0.5 to 10, preferably about 0.5 to 7, volumes (at the pressure employed and at 25° C.) of oxygen-containing gas per liquid volume in the fermentor per minute. This amount is based on air of normal oxygen content being supplied to the reactor, and in terms of pure oxygen the respective ranges would be about 0.1 to 1.7, or preferably about 0.1 to 1.3, volumes (at the pressure employed and at 25° C.) of oxygen per liquid volume in the fermentor per minute.

The pressure employed for the microbial conversion process can range widely. Pressures generally are within the range of about 0 to 50 psig, presently preferably about 0 to 30 psig, more preferably at least slightly over atmospheric pressure, as a balance of equipment and operating cost versus oxygen solubility achieved. Greater than atmospheric pressures are advantageous in that such pressures do tend to increase a dissolved oxygen concentration in the aqueous ferment, which in turn can help increase cellular growth rates. At the same time, this is balanced by the fact that high atmospheric pressures do increase equipment and operating costs.

The fermentation temperature can vary somewhat, but for most bacterial species used in the present invention, the temperature generally will be within the range of about 20° C. to 40° C., generally preferably in the range of about 28° C. to 37° C., depending on the strain of microorganism chosen, as known to those skilled in the art.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 2.0 to 8.0. However, pH range optima for certain microorganisms are dependent on the media employed to some extent, as well as the particular microorganism, and thus change somewhat with change in media as known to those skilled in the art.

While the average retention time of the fermentation admixture in the fermentor can vary considerably, depending in part on the fermentation temperature and culture employed, as known in the art.

In some embodiments, the fermentation is preferably conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily removed. It may be a problem, however, in the case of non-water-soluble substrates, and require added product-treatment steps such as suitable washing steps. The time needed to reach this limiting substrate level is not critical and may vary with the particular microorganism and fermentation process being conducted. However, it is well known in the art how to determine the carbon source concentration in the fermentation medium and whether or not the desired level of carbon source has been achieved.

Although in some embodiments, the fermentation is conducted as a batch or continuous operation, fed batch operation is generally preferred for ease of control, production of uniform quantities of products, and most economical uses of all equipment.

If desired, part or all of the carbon and energy source material and/or part of the assimilable nitrogen source such as ammonia can be added to the aqueous mineral medium prior to feeding the aqueous mineral medium into the fermentor. Indeed, each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermentor, cell density measurable by light transmittancy, or the like. The feed rates of the various materials can be varied so as to obtain as rapid a cell growth rate as possible, consistent with efficient utilization of the carbon and energy source, to obtain as high a yield of microorganism cells relative to substrate charge as possible, but more importantly to obtain the highest production of the desired protein per unit volume.

In either a batch, or the preferred fed batch operation, all equipment, reactor, or fermentation means, vessel or container, piping, attendant circulating or cooling devices, and the like, are initially sterilized, usually by employing steam such as at about 121° C. for at least about 15 minutes. The sterilized reactor then is inoculated with a culture of the selected microorganism in the presence of all the required nutrients, including oxygen, and the carbon-containing substrate. The type of fermentor employed is not critical, though in some embodiments, the 15L Biolafitte (Saint-Germain-en-Laye, France) is preferred.

Protein Separations

In preferred embodiments, once the desired protein is expressed, the secreted protein is recovered. The present invention provides methods of separating a desired protein from its fusion analog. It is specifically contemplated that the methods described herein will find use in the separation of proteinase inhibitor and variants from the fusion analog.

The collection and purification of the desired protein from the fermentation broth can also be achieved using procedures known to those of skill in the art. The fermentation broth will generally contain cellular debris, including cells, various suspended solids and other biomass contaminants, as well as the desired protein product, which are preferably removed from the fermentation broth by means known in the art. Suitable processes for such removal include conventional solid-liquid separation techniques (e.g., centrifugation, filtration, dialysis, microfiltration, rotary vacuum filtration, or other known processes), to produce a cell-free filtrate. In some embodiments, it is preferable to further concentrate the fermentation broth or the cell-free filtrate prior to the purification and/or crystallization process using techniques such as ultrafiltration, evaporation and/or precipitation.

Precipitating the proteinaceous components of the supernatant or filtrate may be accomplished by means of a salt (e.g., ammonium sulfate) or low pH (typically less than 3), followed by purification by a variety of chromatographic procedures (e.g., ion exchange chromatography, affinity chromatography, hydrophobic interaction chromatography, hydrophobic charge induction chromatography etc.) or similar art recognized procedures. It is not intended that the present invention be limited to any particular separation method, as it is contemplated that any method will find use in the present invention.

In certain preferred embodiments, when the expressed desired polypeptide is secreted from the bacterial cells, the polypeptide is purified from the growth media. In preferred embodiments, the expression host cells are removed from the media before purification of the polypeptide (e.g. by centrifugation).

When the expressed recombinant desired polypeptide is not secreted from the host cell, the host cell is preferably disrupted and the polypeptide released into an aqueous "extract" which is the first stage of purification. Preferably, the expression host cells are collected from the media before the cell disruption (e.g. by centrifugation). The cell disruption may be performed by using any suitable means known in the art, such as by lysozyme or beta-glucanase digestion or by forcing the cells through high pressure (See e.g., Scobes, *Protein Purification*, Second edition, Springer-Verlag).

In some embodiments, the addition of six histidine residues (i.e., a "His Tag") to the C-terminus is used as an aid in the purification of the desired protein and its fusion analog. Use of the His tags as a purification aid is well known in the art (See e.g., Hengen, TIBS 20:285-286 [1995]). The 6× his-tagged proteins are easily purified using Immobilized Metal ion Affity Chromatography (IMAC), as known to those skilled in the art.

Purity

For some applications, it is of great importance that the protease inhibitors produced using the present invention be very highly pure (e.g., having a purity of more than 99%). This is particularly true whenever the desired protein is to be used as a therapeutic, but is also necessary for other applications. The methods described herein provide a way of producing substantially pure desired proteins. The desired proteins described herein are useful in pharmaceutical and personal care compositions. However, it is contemplated that proteins of varying purity levels will be produced using the methods of the present invention and it is not intended that the proteins produced using the present invention be limited to any particular level of purity.

Activation of BBI During Purification

In some embodiments of the present invention, after growth during the purification process, the activity of the protein is increased by the addition of chemicals that reduce/oxidize disulfide bonds and/or alter the general redox potential, and/or chemicals that alter solvent properties thus affecting protein conformation and aggregation. In some particularly preferred embodiments, addition of a reagent that reduces disulfide bonds, such as 2-mercaptoethanol, is used to increase activity of the protein. However, as those skilled in the art appreciate, depending purity and buffer composition, other disulfide reducing or oxidizing agents (e.g., DTT, TCEP, reduced and oxidized glutathione, cysteine, cystine, cysteamine, thioglycolate, $S_2O_3^{2-}$, $S_2O_4^{2-}$, $S_2O_5^{2-}$, $SO_3^{2-}$, $S_2O_7^{2-}$, Cu+, protein disulfide isomerases, protein thiol-disulfide oxidoreductases, etc.), either used alone or in combination, find use in the present invention. Other adjuvants that alter solvent properties, (e.g. ethanolamine, DMSO, TWEEN®-80, arginine, urea, etc.), either added alone or preferably in combination with disulfide reducing/oxidizing agents, such as βME, during the purification process also find use in the present invention by increasing the activity of the protein. In certain preferred embodiments, partially purified protein is diluted in buffer (in some particularly preferred embodiments, a zwitterionic buffer with TWEEN®-80 at basic pH) and activated with bME and a disulfide oxidizing agent (in alternative preferred embodiments, oxidized glutathione or sodium sulfite).

In addition, it is contemplated that conditions will be screened in order to determine the optimal activation of the protein, if desired. For example, various βME concentrations (0.1-10 mM), oxidizing agent concentrations (0 to 1/20 to 20 times the βME concentration) pH (7.5-9.5), temperatures (15-40° C.), dilutions (1-20 fold), incubation times (12-72 h), aeration (incubations under inert gas to vigorous mixing under oxygen containing gases), buffer types (Tris, CHES, CAPS, Tricine, TAPS, other zwitterionic buffers, etc.), buffer concentrations (0.1-1 M), and the addition of various adjuvants known to alter solvent properties thereby affecting protein conformation and aggregation (e.g., ethanolamine, DMSO, TWEEN®-80, arginine, urea, etc.) are tested in order to determine the optimum conditions for the expression system used. It is not intended that the present invention be limited to any particular disulfide reducing/oxidizing agent, dilution, temperature, pH, buffer type or composition, or adjuvant, as any suitable reagents known to those skilled in the art find use in the present invention.

EXPERIMENTAL

The present invention is described in further detail in the following Examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention In the experimental disclosure which follows, the following abbreviations apply PI (proteinase inhibitor), BBI (Bowman-Birk inhibitor), STI (Soybean Trypsin inhibitor); VEGF and VegF (vascular endothelial growth factor); ppm (parts per million); M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); (HCl (hydrochloric acid); aa (amino acid); bp (base pair); kb (kilobase pair); kD (kilodaltons); cDNA (copy or complimentary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto Tryptone, 24 g/l glycerol, 2.31 g/l $KH_2PO_4$, and 12.54 g/l $K_2HPO_4$); $OD_{280}$ (optical density at 280 nm); $OD_{600}$ (optical density at 600 nm); $A_{405}$ (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN® 20); PEG (polyethylene glycol); PCR (polymerase chain reaction); RT-PCR (reverse transcription PCR); SDS (sodium dodecyl sulfate); Tris (tris(hydroxymethyl)aminomethane); HEPES (N-[2-Hydroxyethyl]piperazine-N-[2-ethanesulfonic acid]); HBS (HEPES buffered saline); SDS (sodium dodecylsulfate); bME, BME and βME (beta-mercaptoethanol or 2-mercaptoethanol); Tris-HCl (tris[Hydroxymethyl]aminomethane-hydrochloride); Tricine (N-[tris-(hydroxymethyl)-methyl]-glycine); CHES (2-(N-cyclo-hexylamino) ethane-sulfonic acid); TAPS (3-{[tris-(hydroxymethyl)-methyl]-amino}-propane-sulfonic acid); CAPS (3-(cyclo-hexylamino)-propane-sulfonic acid; DMSO (dimethyl sulfoxide); DTT (1,4-dithio-DL-threitol); Glut and GSH (reduced glutathione); GSSG (oxidized glutathione); TCEP (Tris[2-carboxyethyl] phosphine); Ci (Curies) mCi (milliCuries); μCi (microCuries); TLC (thin layer achromatography); Ts (tosyl); Bn (benzyl); Ph (phenyl); Ms (mesyl); Et (ethyl), Me (methyl); Taq (*Thermus aquaticus* DNA polymerase); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetracetic acid); bla (β-lactamase or ampicillin-resistance gene); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Pisacataway, N.J.); NCBI (National Center for Biotechnology Information); Applied Biosystems (Applied Biosystems, Foster City, Calif.); Clontech (CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc., King of Prussia, Pa.); Difco (Difco Laboratories, Detroit, Mich.); Mediatech (Mediatech, Herndon, Va.; Santa Cruz (Santa Cruz Biotechnology, Inc., Santa Cruz, Calif.); BioVeris (BioVeris Corp., Gaithersburg, Md.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Molecular Devices (Molecular Devices, Corp., Sunnyvale, Calif.); R&D Systems (R&D Systems, Minneapolis, Minn.); Stratagene (Stratagene Cloning Systems, La Jolla, Calif.); Marsh (Marsh Biosciences, Rochester, N.Y.); Bio-Tek (Bio-Tek Instruments, Winooski, VT); (Biacore (Biacore, Inc., Piscataway, N.J.); PeproTech (PeproTech, Rocky Hill, N.J.); SynPep (SynPep, Dublin, Calif.); and Microsoft (Microsoft, Inc., Redmond, Wash.).

Example 1

Production of BCE103-BBI Fusion Proteins in *B. subtilis*

In this Example, experiments conducted to produce BCE103-BBI fusion proteins in *B. subtilis* are described. The DNA sequence of the synthetic gene (Operon Technologies) coding for the pro-BBI protein with a C-terminal hexa-histidine tag used in these experiments is:

```
                                          (SEQ ID NO:10)
AACCTGCGTCTGTCTAAGCTTGGCCTGCTTATGAAATCAGACCATCAGCA

CAGCAATGACGATGAGAGCTCTAAACCCTGTTGCGATCAATGCGCATGTA

CGAAATCAAATCCTCCACAGTGTCGGTGTTCCGATATGCGTCTGAATAGC

TGTCATAGTGCATGCAAAAGCTGTATCTGCGCCCTGAGTTATCCAGCTCA

ATGTTTTTGCGTCGACATCACGGACTTCTGCTATGAGCCATGTAAACCAA

GCGAGGACGATAAAGAGAACCATCATCACCATCACCAT
```

The protein sequence of pro-BBI with a C-terminal hexa-histidine tagged coded for by the above synthetic gene is:

```
                                          (SEQ ID NO:11)
NLRLSKLGLLMKSDHQHSNDDESSKPCCDQCACTKSNPPQCRCSDMRLNS

CHSACKSCICALSYPAQCFCVDITDFCYEPCKPSEDDKENHHHHHH
```

The portion of the DNA sequence of the synthetic gene that codes for the major mature form of BBI is:

```
                                          (SEQ ID NO:12)
GACGATGAGAGCTCTAAACCCTGTTGCGATCAATGCGCATGTACGAAATC

AAATCCTCCACAGTGTCGGTGTTCCGATATGCGTCTGAATAGCTGTCATA

GTGCATGCAAAAGCTGTATCTGCGCCCTGAGTTATCCAGCTCAATGTTTT
```

-continued

```
TGCGTCGACATCACGGACTTCTGCTATGAGCCATGTAAACCAAGCGAGGA

CGATAAAGAGAAC
```

The protein sequence of the major mature form of BBI coded by the above synthetic gene is:

```
                                          (SEQ ID NO:13)
DDESSKPCCDQCACTKSNPPQCRCSDMRLNSCHSACKSCICALSYPAQCF

CVDITDFCYEPCKPSEDDKEN
```

The PCR primers used to amplify the BBI gene for fusion to the BCE103 cellulase expression cassette in the pJ103 vector were:

```
                                          (SEQ ID NO:14)
BBIfusion_FW:      5' CAGCACGGATCCAGACGATGAGAGCTCT

                   AAACCC 3'

                                          (SEQ ID NO:15)
BBIHindIlI_RV:     5' CTGCAGAAGCTTAAAAATAAAAAAACGGA

                   TTTCCTTCAGGAAATCCGTCCTCTGTTAACTT

                   TTAGTTCTCTTTATCGTCCTCGC 3'

                                          (SEQ ID NO:16)
BBIHIS-HindIII_RV: 5' CTGCAGAAGCTTTAAAAATAAAAAAACGGA

                   TTTCCTTCAGGAAATCCGTCCTCTGTTAACTT

                   TTAATGGTGATGGTGATGATGGTTCTC 3'
```

The sequence of the aprE-BCE103-BBI-HisTag expression cassette (EcoRI-HindIII) that was cloned into the pJM103 integration vector is provided in FIG. 1. A schematic plasmid map of the pJM103BBIHis expression vector is provided in FIG. 2.

The alkaline cellulase (BCE103) gene (See, van Soligen, U.S. Pat. No. 6,063,611, hereby incorporated by reference) fused to the *B. subtilis* aprE promoter and signal sequence, was cloned from pUCAPR103 (Shaw et al., J. Mol. Biol., 320:303-309 [2002]) as an EcoRI-BamHI fragment (i.e., a fragment that carries the coding sequence of the BCE103 catalytic domain and first cellulose binding domain linker only) into pJM103 (Perego, "Integrational vectors for genetic manipulation in *Bacillus subtilis*" In, *Bacillus subtilis* and Other Gram-positive Bacteria: Biochemistry, Physiology, and Molecular Genetics, Sonenshein, Hoch, and Losick (eds), American Society for Microbiology, Washington D.C., pp. 615-624 [1993]). A gene encoding the soybean Bowman-Birk protease inhibitor (BBI) (Swiss-Prot Accession # P01055; See, Odani and Ikenaka, J. Biochem., 71: 839-848 [1972]) with a C-terminal hexa-histidine tag (His-Tag) was synthesized by Operon Technologies (See, DNA sequence above). The BBI gene was amplified by PCR with primers (all primers were synthesized by MWG Biotech, Oligos Etc., or Operon Technologies) that generated a 5' BamHI site in the correct reading frame with the BCE103 gene, and at the 3' end introduced a strong transcriptional terminator (LAT, from the *Bacillus licheniformis* α-amylase gene) after the end of the BBI gene with a 3' HindIII site for cloning into the pJM103 vector.

PCR fragments with or without a C-terminal His-Tag were generated with the primers BBIfusion_FW (SEQ ID NO:14) and BBIHISHindIII_RV (SEQ ID NO:16), or BBIfusion_FW (SEQ ID NO:14) and BBI-HindIII_RV(SEQ ID NO:15), respectively, using the synthetic BBI gene as a template. Unless indicated otherwise, PCR reactions were typically performed on a thermocycler for 30 cycles with High Fidelity Platinum Taq polymerase (Invitrogen) according to the instructions of the supplier (with an annealing temperature of 55° C.). The PCR fragments were cloned as BamHI-HindIII fragments into pJM103 carrying the aprE-BCE 103 expression cassette. The correct gene sequence was verified by DNA sequencing.

Thus, as shown in FIG. 1, the N-terminus of the mature coding region of the BBI gene (with or without the His-Tag) was fused in frame to the C-terminal coding region of the first CBD (cellulose binding domain) linker sequence coded by the BCE103 cellulase gene. Thereby, the two CBD's of BCE103 (Shaw et al., supra) are replaced by BBI in the final expression vectors, pJM103BBI or pJM103BBIhis (See, FIG. 2). The aprE promoter controls the expression of the BCE103-BBI gene fusions (See, Ferrari et al., J. Bact., 170: 289-295 [1988]; and Henner et al., J. Bact., 170: 296-300 [1988]).

Competent *Bacillus subtilis* cells, BG3934comK (degU$^{Hy}$32, oppA, ΔspoIIE3501, ΔaprE, ΔnprE, Δepr, ΔispA, Δbpr, amyE::xylRPxylAcomK-phleo), were transformed with the expression plasmids, pJM103BBI or pJM103BBIhis. The bacteria were made competent by the induction of the comK gene under control of a xylose inducible promoter (Hahn et al., Mol. Microbiol., 21:763-775 [1996]). The transformants were selected on Luria Broth agar (LA) plates containing 5 μg/ml chloramphenicol. To increase the expression by gene amplification, colonies were streaked and grown several times on LA plates with 25 μg/ml chloramphenicol until the growth rate with the antibiotic was similar to growth rate in the absence of chloramphenicol. The BCE103-BBI fusion protein was produced by growth in shake flasks at 37° C. in TSB medium (Tryptone Soya Broth from OXOID, 30 g/L) or in MBD medium, a MOPS based defined medium. MBD medium was made essentially as described (Neidhardt et al., J. Bacteriol., 119: 736-747 [1974]), except NH$_4$Cl$_2$, FeSO$_4$, and CaCl$_2$ were left out of the base medium, 3 mM K$_2$HPO$_4$ was used, and the base medium was supplemented with 60 mM urea, 75 g/L glucose, and 1% soytone. Also, the micronutrients were made up as a 100× stock containing in one liter, 400 mg FeSO$_4$ 7H$_2$O, 100 mg MnSO$_4$.H$_2$O, 100 mg ZnSO$_4$.7H$_2$O, 50 mg CuCl$_2$.2H$_2$O, 100 mg CoCl$_2$.6H$_2$O, 100 mg NaMoO$_4$.2H$_2$O, 100 mg Na$_2$B$_4$O$_7$.10H$_2$O, 10 ml of 1M CaCl$_2$, and 10 ml of 0.5 M sodium citrate.

BCE103-BBI fusion protein could be easily visualized in samples from cell free supernatants (after 24 h of growth in TSB medium or 48 h in MBD medium) as the major protein band on SDS-PAGE gels (10% NuPAGE in MES buffer, run as described by the manufacturer, Invitrogen) running at ~44 kDa by using standard protein stains (e.g. GelCode Blue Stain Reagent; Pierce). The identity of the BCE103-BBI fusion protein was verified by immunoblots of SDS-PAGE gels using the protocols supplied by the manufacturer (BM Chromogenic Western Blotting Kit; Roche Applied Science using an anti-HisTag antibody or an anti-BCE103 cellulase polyclonal antibody for detection).

To determine the BCE103 activity, cellulase degradation was assessed qualitatively on LA cellulase indicator plates (with 1% carboxymethylcellulose stained with 0.2% Congo Red, or with 0.5% azo-CM-cellulose, Megazyme), or quantitatively by a direct assay in Assay Buffer (100 mM Tris pH 8.6, 0.005% Tween-80) on the culture broth using a the synthetic substrate, 4-nitrophenyl β-D-cellobioside (Sigma), using methods known in the art (See e.g., van Tilbeurgh et al., Meth. Enzymol., 160:45-59 [1988]).

Trypsin inhibitory assays were performed in Assay Buffer to determine the BBI activity. Specifically, a standard curve was generated by making eleven 1:1 serial dilutions (100 μL BBI+100 μL Assay Buffer) of a 2 μg/mL standard BBI solution. The BBI standard was purified from a 1 mg/ml Trypsin-Chymotrypsin Inhibitor (Sigma Cat. #T-9777) solution in 20 mM MES pH 6.0 using a hydrophobic interaction column (POROS HP2, Phenyl column, Applied Biosystems). The column was equilibrated with 20 mM MES pH 6.0, loaded with 5 mg of the inhibitor, washed with the equilibration buffer, and then the BBI was eluted with water. Unknown BBI samples to be tested in the inhibitory assay were diluted as necessary, so that two or more data points would fall within the standard curve (usually 1:10, 1:100, 1:200, 1:1000, 1:2000 sample dilutions were tested and then the dilutions fine tuned if necessary). Each diluted BBI standard or sample, 20 μL, was added to 80 μL of 50 ng/ml bovine pancreatic trypsin (Worthington) (made by diluting a stock 1 mg/mL trypsin solution into Assay Buffer). For convenience, the standards and samples were arrayed in 96 well microtiter plates. The reactions were mixed and incubated 15 min at 25° C. After the incubation, 100 μL of the 0.5 mg/ml trypsin substrate (diluted in Assay Buffer from a 100 mg/ml solution in DMSO), Suc-AAPR-pNA (succinyl-Ala-Ala-Pro-Arg-para-nitroanilide, Bachem), was added, mixed and the OD ($A_{405}$) was monitored for 15 min, with 1 time point recorded every 12 sec using a Spectra Max 250 (Molecular Devices). The data points were used to determine the Vmax for each reaction. The standard curve was generated by plotting Vmax versus BBI concentration and was fitted to a four-parameter curve. All data fitting was done using software supplied by the manufacturer (Molecular Devices). The BBI concentration of the unknown samples was calculated from the standard curve. Alternatively, the BBI activity was measured using the same protocol but by determining bovine pancreatic chymotrypsin (Worthington) inhibition (chymotrypsin was used at the same concentration as trypsin and chymotrypsin activity was measured by adding 100 μL of a 0.4 mg/ml chymotrypsin substrate, succinyl-Ala-Ala-Pro-Phe-para-nitroanilide, Bachem).

Titers from shake flask runs (500 ml MBD medium in 2.8 L Fernbach 6 baffled flasks, 37° C., 225 rpm, harvested 60 h after of growth) typically ranged from 0.4-0.9 mg/ml BCE activity and 40-150 μg/ml BBI trypsin inhibitory activity. However, it is contemplated that titers likely could be improved further by optimizing the bacterial strain, culture medium and growth conditions (aeration, temperature, time of harvest, etc.).

In addition to the BCE103 fusion to wild-type BBI, fusion proteins to BBI variants and fusion proteins with various linkers between BCE103 and BBI were produced using the methods outlined above, as described in the following Examples. In addition, fusion proteins were also produced when the BBI was fused to the 2$^{nd}$ CBD linker (BCE-cbdD-BBI; See, Example 4) making it possible to use the 1$^{st}$ CBD to aid in the purification process.

Example 2

Production of Peptides Substituted into the BBI Reactive Site Loops as BCE103-BBI Fusion Proteins In this Example, experiments conducted to produce peptides substituted into the BBI reactive site loops as BCE103-BBI fusion proteins are described. The primers, as well as other sequences used in the various steps of these experiments are provided below. The sequence of 12BBIck81 from the BCE103 fusion site (at the BamHII) to the end of the gene is provided in FIG. 3. The CK37281 peptide sequences (ACYNLYGWTC (SEQ ID NO:9) are inserted into both the trypsin and chymotrypsin inhibitory loops.

The primers used to introduce an EcoRI site in the BBI gene using QuikChange® site-directed mutagenesis (Stratagene) were:

```
BowBeco-F
5'-GATATGCGTCTGAATTCCTGTCATAGTGCAT (SEQ ID NO:17)

BowBeco-R
5'-ATGCACTATGACAGGAATTCAGACGCATATC (SEQ ID NO:18)
```

The sequences of the DNA oligonucleotides that were annealed and cloned in the BBI gene (SacI-EcoRI) to replace the trypsin inhibitory loop with the VegF binding peptide CK37281 were:

```
1BBck81+                          (SEQ ID NO:19)
5'-CTAAACCCTGTTGCGATCAATGCGCATGTTATAATTTGTATGGGTGG

ACTTGTCGCTGCAGCGATATGCGTCTG

1BBck81-                          (SEQ ID NO:20)
5'-AATTCAGACGCATATCGCTGCAGCGACAAGTCCACCCATACAAATTA

TAACATGCGCATTGATCGCAACAGGGTTTAGAGCT
```

The sequences of the DNA oligonucleotides that were annealed and cloned in the BBI gene (EcoRI-SalI) to replace the chymotrypsin inhibitory loop with the VegF binding peptide CK37281 were:

```
2BBck81+                          (SEQ ID NO:21)
5'-AATTCCTGTCATAGTGCCTGCAAAAGGTGCGCATGTTATAACCTGTA

CGGGTGGACCTGTTTTTGCG

2BBck81-                          (SEQ ID NO:22)
5'-TCGACGCAAAAACAGGTCCACCCGTACAGGTTATAACATGCGCAGCT

TTTGCAGGCACTATGACAGG
```

The DNA sequences of the oligonucleotide pairs used to make cassettes to introduce peptides into the trypsin (SacI and EcoRI restriction sites) or chymotypsin (EcoRI and SalI restriction sites) reactive site loops of the synthetic BBI gene are provided below. These peptide coding sequences were then moved into the p2JM103BBI expression vector as SacI-SalI fragments.

```
Comstatin (1st loop)
                                  (SEQ ID NO:23)
CTAAACCCTGTGCGATCAATGCGCATGTGTTGTTCAGGACTGGGGTCAC

CACCGTTGTCGCTGCAGCGATATGCGTCTG
and
                                  (SEQ ID NO:24)
AATTTCAGACGCATATCGCTGCAGCGACAACGGTGGTGACCCCAGTCCT

GAACAACACATGCGATTGATCGCAACAGGGTTTAGAGCT

Comstatin (2nd loop)
                                  (SEQ ID NO:25)
CAAAAGCTGTATCTGCGTTGTTCAGGACTGGGGTCACCACCGTTG

TTTTTGCG
and
                                  (SEQ ID NO:26)
TCGACGCAAAAACAACGGTGGTGACCCCAGTCCTGAACAACGCAGATAC

AGCTTTTGCATG

C2c (1st loop)
                                  (SEQ ID NO:27)
CTAAACCCTGTTGCGATCAATGCAGCTGTGGTCGTAAAATCCCGATCCA
```

-continued

```
GTGTCGCTGCAGCGATATGCGTCTG
and
                                  (SEQ ID NO:28)
AATTCAGACGCATATCGCTGCAGCGACACTGGATCGGGATTTT

ACGACCACAGCTGCATTGATCGCAACAGGGTTTAGAGCT

C3c (1st loop)
                                  (SEQ ID NO:29)
CTAAACCCTGTTGCGATCAATGCGGTTGTGCTCGTTCTAACCTGGACGAA

TGTCGCTGCAGCGATATGCGTCTG
and
                                  (SEQ ID NO:30)
AATTCAGACGCATATCGCTGCAGCGACATTCGTCCAGGTTAGAACGAGC

ACAACCGCATTGATCGCAACAGGGTTTAGAGCT

C4c (1st loop)
                                  (SEQ ID NO:31)
CTAAACCCTGTTGCGATCAATGCGGTTGTCAGCGTGCTCTGCCGATCCTG

TGTCGCTGCAGCGATATGCGTCTG
and
                                  (SEQ ID NO:32)
AATTCAGACGCATATCGCTGCAGCGACACAGGATCGGCAGAGCACGCTGA

CAACCGCATTGATCGCAACAGGGTAGAGCT

C5c (1st loop)
                                  (SEQ ID NO:33)
CTAAACCCTGTTGCGATCAATGCCAGTGTGGTCGTCTGCACATGAAAACC

TGTCGCTGCAGCGATATGCGTCTG
and
                                  (SEQ ID NO:34)
AATTCAGACGCATATCGCTGCAGGGACAGGTTTTCATGTGCAGACGACCA

CACTGGCATTGATCGCAACAGGGTTTAGAGCT

Xa1 (2nd loop)
                                  (SEQ ID NO:35)
AATTCCTGTCATAGTGCCTGCAAAAGCTGTATCTGCGCCCGTAGTTTGCC

AGCTCAATGTTTTTGCG
and
                                  (SEQ ID NO:36)
TCGACGCAAAAACATTGAGCTGGCAAACTACGGGCGCAGATACAGCTTTT

GCAGGCACTATGACAGG

hSCC1 (1st loop)
                                  (SEQ ID NO:37)
CTAAACCCTGTTGCGATCAATGCAACTGTACGTACTCAACCCCTCCACAG

TGTCGCTGCAGCGATATGCGTCTG
and
                                  (SEQ ID NO:38)
AATTCAGACGCATATCGCTGCAGCGACACTGTGGAGGGGTTGAGTACGTA

CAGTTGCATTGATCGCAACAGGGTTTAGAGCT
```

The DNA sequences of oligonucleotide primer pairs used to introduce peptide sequences into the trypsin or chymotrypsin reactive site loops using a QuikChange® II XL site-directed mutagenesis kit (Stratagene) are provided below. The reactions were performed as outlined by the manufacturer and described in this Example. Twenty cycles were performed with extensions of 6 minutes at 68° C., denaturations of 50 s at 95° C., and annealings at 55° C. for 50 s. After the cycles, a final extension was performed at 68° C. for 20 minutes.

1A (2nd loop)
CTGTATCTGCAAACGCTCAAAATCTCGTGGCTGTTTTTGCGTCGACATCAC (SEQ ID NO:39)
and

CGCAAAAACAGCCACGAGATTTTGAGCGTTTGCAGATACAGCTTTTGCATG (SEQ ID NO:40)

2B (2nd loop)
CTGTATCTGCTGGTATAATCAAATGACAACATGTTTTTGCGTCGACATCAC (SEQ ID NO:41)
and

CGCAAAAACATGTTGTCATTTGATTATACCAGCAGATACAGCTTTTGCATG (SEQ ID NO:42)

4A (2nd loop)
CTGTATCTGCCATCAACTTGGCCCGAATTCATGTTTTTGCGTCGACATCAC (SEQ ID NO:43)
and

CGCAAAAACATGAATTCGGGCCAAGTTGATGGCAGATACAGCTTTTGGATG (SEQ ID NO:44)

5A (2nd loop)
CTGTATCTGCCATCCGTGGGCACCGTATTCTTGTTTTTGCGTCGACATCAC (SEQ ID NO:45)
and

CGCAAAAACAAGAATACGGTGCCCACGGATGGCAGATACAGCTTTTGCATG (SEQ ID NO:46)

6-1A (2nd loop)
CTGTATCTGCAATCTTCATTATCTTCAACAGTGTTTTTGCGTCGACATCAC (SEQ ID NO:47)
and

CGCAAAAACAGTGTTGAAGATAATGAAGATTGCAGATACAGCTTTTGCATG (SEQ ID NO:48)

7A (2nd loop)
CTGTATCTGCACACCGTCTCTTTATCGCCCGTGTTTTTGCGTCGACATCAC (SEQ ID NO:49)
and

CGCAAAAACACGGGCGATAAAGAGACGGTGTGCAGATACAGCTTTTGCATG (SEQ ID NO:50)

8B (2nd loop)
CTGTATCTGCCTTACAGATCAATCTAAACCGTGTTTTTGCGTCGACATCAC (SEQ ID NO:51)
and

CGCAAAAACACGGTTTAGATTGATCTGTAAGGCAGATACAGCTTTTGCATG (SEQ ID NO:52)

9A (2nd loop)
CTGTATCTGCGTTACAACATCAATGGGCATGTGTTTTTGCGTCGACATCAC (SEQ ID NO:53)
and

CGCAAAAACACATGCCCATTGATGTTGTAACGCAGATACAGCTTTTGCATG (SEQ ID NO:54)

10B (2nd loop)
CTGTATCTGCCGCGCATCACCGTATGATTGGTGTTTTTGCGTCGACATCAC (SEQ ID NO:55)
and

CGCAAAAACACCAATCATACGGTGATGCGCGGCAGATACAGCTTTTGCATG (SEQ ID NO:56)

11-1A (2nd loop)
CTGTATCTGCTCAACACAAAAAATTCCGCAATGTTTTTGCGTCGACATCAC (SEQ ID NO:57)
and

CGCAAAAACATTGCGGAATTTTTTGTGTTGAGCAGATACAGCTTTTGCATG (SEQ ID NO:58)

12B (2nd loop)
CTGTATCTGCACACAATTTCGCTCTGCAACATGTTTTTGCGTCGACATCAC (SEQ ID NO:59)
and

CGCAAAAACATGTTGCAGAGCGAAATTGTGTGCAGATACAGCTTTTGCATG (SEQ ID NO:60)

13A (2nd loop)
CTGTATCTGCCCGGATCATGTTCCGCATCTTTGTTTTTGCGTCGACATCAC (SEQ ID NO:61)
and

CGCAAAAACAAAGATGCGGAACATGATCCGGGCAGATACAGCTTTTGCATG (SEQ ID NO:62)

15-1A (2nd loop)
CTGTATCTGCTCAGGCTTTCCGCTTTCTACATGTTTTTGCGTCGACATCAC (SEQ ID NO:63)
and

CGCAAAAACATGTAGAAAGCGGAAAGCCTGAGCAGATACAGCTTTTGCATG (SEQ ID NO:64)

1A6 (1st loop)
TCAATGCGCATGTGAAGAGATCTGGACTATGCTTTGCCGGTGTCCGATATGCGTC (SEQ ID NO:65)

-continued and

CGGAACACCGGCAAAGCATAGTCCAGATCTCTTCACATGCGCATTGATCGCAACAGG (SEQ ID NO:66)

1A6 ($2^{nd}$ loop)
CAAAAGCTGTGCTTGTGAAGAGATCTGGACTATGCTTTGCTTTTGCGTCGACATCACGG (SEQ ID NO:67)
and

ACGCAAAAGCAAAGCATAGTCCAGATCTCTTCACAAGCACAGCTTTTGCATGCACTATG (SEQ ID NO:68)

1C2 ($1^{st}$ loop)
TCAATGCGCATGTTGGGCCCTTTTACTGTCAAAACATGCCGGTGTTCCGATATGCGTC (SEQ ID NO:69)
and

CGGAACACCGGCATGTTTTGACAGTAAGGGCCCAACATGCGCATTGATCGCAACAGG (SEQ ID NO:70)

1C2 ($2^{nd}$ loop)
CAAAAGCTGTGCTTGTTGGGCCCTTACTGTCAAAACATGCTTTTGCGTCGACATCACGG (SEQ ID NO:71)
and

ACGCAAAAGCATGTTTTGACAGTAAGGGCCCAACAAGCACAGCTTTTGCATGCACTATG (SEQ ID NO:72)

2E2 ($1^{st}$ loop)
TCAATGCGCATGTCTTACAGTACTGTGGACTACATGCCGGTGTTCCGATATGCGTC (SEQ ID NO:73)
and

CGGAACACCGGCATGTAGTCCACAGTACTGTAAGACATGCGCATTGATCGCAACAGG (SEQ ID NO:74)

2E2 ($2^{nd}$ loop)
CAAAAGCTGTGCTTGTCTTACAGTACTGTGGACTACATGCTTTTGCGTCGACATCACGG (SEQ ID NO:75)
and

ACGCAAAAGCATGTAGTCCACAGTACTGTAAGACAAGCACAGCTTTTGCATGCACTATG (SEQ ID NO:76)

2E5 ($1^{st}$ loop)
TCAATGCGCATGTACTCTTTGGAACAGATCTCCTTGCCGGTGTTCCGATATGCGTC (SEQ ID NO:77)
and

CGGAACACCGGCAAGGAGATCTGTTCCAAAGAGTACATGCGCATTGATCGCAACAGG (SEQ ID NO:78)

2E5 ($2^{nd}$ loop)
CAAAAGCTGTGCTTGTACTGTTTGGAATCGATCTCCTTGCTTTTGCGTCGACATGACGG (SEQ ID NO:79)
and

ACGCAAAAGCAAGGAGATCGATTCCAAAGAGTACAAGCACAGCTTTTGCATGGACTATG (SEQ ID NO:80)

FGFns ($1^{st}$ loop)
TCAATGCGCATGTACAAACATCGATTCTACTCCTTGCCGGTGTTCCGATATGCGTC (SEQ ID NO:81)
and

CGGAACACCGGCAAGGAGTAGAATCGATGTTTGTACATGCGCATTGATCGCAACAGG (SEQ ID NO:82)

FGFns ($2^{nd}$ loop)
CAAAAGCTGTGCTTGCACAAACATCGATTCTACTCCTTGTTTTTGCGTCGACATCACGG (SEQ ID NO:83)
and

ACGCAAAAACAAGGAGTAGAATCGATGTTTGTGCAAGCACAGCTTTTGCATGCACTATG (SEQ ID NO:84)

FGFkr ($1^{st}$ loop)
TCAATGCGCATGTACAAAAATCGATCGTACTCCTTGCCGGTGTTCCGATATGCGTC (SEQ ID NO:85)
and

CGGAACACCGGCAAGGAGTACGATCGATTTTTGTACATGCGCATTGATCGCAACAGG (SEQ ID NO:86)

FGFkr ($2^{nd}$ loop)
CAAAAGCTGTGCTTGCACAAAAATCGATCGTACTCCTTGTTTTTGCGTCGACATCACGG (SEQ ID NO:87)
and

ACGCAAAAACAAGGAGTAGGATCGATTTTTGTGCAAGCACAGCTTTTGCATGCACTATG (SEQ ID NO:88)

FGFhl ($1^{st}$ loop)
TCAATGCGCATGTCACCTGCAGACAACTGAAACATGCCGGTGTTCCGATATGCGTC (SEQ ID NO:89)
and

CGGAACACCGGCATGTTTCAGTTGTCTGCAGGTGACATGCGCATTGATCGCAACAGG (SEQ ID NO:90)

-continued

FGFh1 (2nd loop)
CAAAAGCTGTGCTTGCCACCTGCAGACAACTGAAACATGTTTTTGCGTCGACATCACGG (SEQ ID NO:91)
and

ACGCAAAAACATGTTTCAGTTGTCTGCAGGTGGCAAGCACAGCTTTTGCATGCACTATG (SEQ ID NO:92)

FGFgy (1st loop)
TCAATGCGCATGTGGCTACTTCATCCCATCGATTTGCCGGTGTTCCGATATGCGTC (SEQ ID NO:93)
and

CGGAACACCGGCAAATCGATGGGATGAAGTAGCCACATGCGCATTGATCGCAACAGG (SEQ ID NO:94)

FGFgy (2nd loop)
CAAAAGCTGTGCTTGCGGCTACTTCATCCCATCGATTTGTTTTTGCGTCGACATCACGG (SEQ ID NO:95)
and

ACGCAAAAACAAATCGATGGGATGAAGTAGCCGCAAGCACAGCTTTTGCATGCACTATG (SEQ ID NO:96)

MM005 (1st loop)
TCAATGCGCATGTTTACGTATCCTTGCTAACAAATGCCGGTGTTCCGATATGCGTC (SEQ ID NO:97)
and

CGGAACACCGGCATTTGTTAGCAAGGATACGTAAACATGCGCATTGATCGCAACAGG (SEQ ID NO:98)

MM005 (2nd loop)
CAAAAGCTGTGCTTGCTTACGTATCCTTGCTAACAAATGTTTTTGCGTCGACATCACGG (SEQ ID NO:99)
and

ACGCAAAAACATTTGTTAGCAAGGATACGTAAGCAAGCACAGCTTTTGCATGCACTATG (SEQ ID NO:100)

MM007 (1st loop)
GCGATCAATGCGCCTGCAGAACTCAACCATATCCTTTATGTCGGTGTTCCGATATGCGTC (SEQ ID NO:101)
and

GGAACACCGACATAAAGGATATGGTTGAGTTCTGCAGGCGCATTGATCGCAACAGGGTT (SEQ ID NO:102)

MM007 (2nd loop)
CAAAAGCTGTGCCTGCAGAACACAACCTTACCCACTTTGTTTTTGCGTCGACATCACGG (SEQ ID NO:103)
and

ACGCAAAAACAAAGTGGGTAAGGTTGTGTTTCTGCAGGCACAGCTTTTGCATGCACTATG (SEQ ID NO:104)

MM009 (2nd loop)
CAAAAGCTGTGCCTGCCTGTTAACACCTACTCTTAACTGTTTTTGCGTCGACATCACGG (SEQ ID NO:105)
and

ACGCAAAAACAGTTAAGAGTAGGTGTTAACAGGCAGGCACAGCTTTTGCATGCACTATG (SEQ ID NO:106)

MM010 (1st loop)
TCAATGCGCATGCGCTCTTCCAACTCATTCTAACTGTCGGTGTTCCGATATGCGTCT (SEQ ID NO:107)
and

CGGAACACCGACAGTTAGAATGAGTTGGAAGAGCGCATGCGCATTGATCGCAACAGG (SEQ ID NO:108)

MM010 (2nd loop)
CAAAAGCTGTGCCTGCGCGCTTCCTACACACTCTAACTGTTTTTGCGTCGACATCACGG (SEQ ID NO:109)
and

ACGCAAAAACAGTTAGAGTGTGTAGGAAGCGCGCAGGCACAGCTTTTGCATGCACTATG (SEQ ID NO:110)

MM017 (2nd loop)
CAAAAGCTGTGCCTGCCCTTTAGGCCTTTGCCCACCTTGTTTTTGCGTCGACATCACGG (SEQ ID NO:111)
and

ACGCAAAAACAAGGTGGGCAAAGGCCTAAAGGGCAGGCACAGCTTTTGCATGCACTATG (SEQ ID NO:112)

FGFps1 (2nd loop)
AAGCTGTATCTGCTGGAAGATCGATTCTACACCTTGTTTTTGCGTCGACATCACGG (SEQ ID NO:113)
and

ACGCAAAAACAAGGTGTAGAATCGATGTTCCAGCAGATACAGCTTTTGCATGCACT (SEQ ID NO:114)

FGFps2 (1st loop)
GCGATCAATGCATCTGTACTTGGATTGACAGTACTCCTTGTCGGTGTTCCGATATGCGTC (SEQ ID NO:115)
and

GGAACACCGACAAGGAGTACTGTCAATCCAAGTACAGATGCATTGATCGCAACAGGGTTT (SEQ ID NO:116)

-continued

FGFps2 (2$^{nd}$ loop)
AAGCTGTATCTGCACATGGATCGATAGTACTCCTTGTTTTTGCGTCGACATCACGG (SEQ ID NO:117)
and

ACGCAAAAACAAGGTGTAGAATCGATCCATGTGCAGATACAGCTTTTGCATGCACT (SEQ ID NO:118)

FGFpsB (2$^{nd}$ loop)
AAGCTGTATCTGTACATGGATCGATTGGACACCTTGTTTTTGCGTCGACATCACGG (SEQ ID NO:119)
and

ACGCAAAAACAAGGTGTCCAATCGATCCATGTACAGATACAGCTTTTGCATGCACT (SEQ ID NO:120)

1A8 (2$^{nd}$ loop)
CAAAAGCTGCGCATGTGTTACTACAGATTGGATCGAATGTTTTTGCGTCGACATCACGG (SEQ ID NO:121)
and

ACGCAAAAACATTCGATCCAATCTGTAGTAACACATGCGCAGCTTTTGCATGCACTATG (SEQ ID NO:122)

1A12 (2$^{nd}$ loop)
CAAAAGCTGTGCCTGCCCAACACTTTGGACTCATATGTGTTTTTGCGTCGACATCACGGAC (SEQ ID NO:123)
and

ACGCAAAAACACATATGAGTCCAAAGTGTTGGGCAGGCACAGCTTTTGCATGCACTATGAC (SEQ ID NO:124)

1E11 (2$^{nd}$ loop)
CAAAAGCTGCGCATGTTACTACTCTCAATTCCACCAATGTTTTTGCGTCGACATCACGG (SEQ ID NO:125)
and

ACGCAAAAACATTGGTGGAATTGAGAGTAGTAACATGCGCAGCTTTTGCATGCACTATG (SEQ ID NO:126)

TGFps1 (2$^{nd}$ loop)
CAAAAGCTGTCTTTGTCCGGAAAACGATAACGTTTCTCCTTGTAATTGCGTCGACATCACGGACTTCTG (SEQ ID NO:127)
and TGTCGACGCAATTACAAGGAGAAACGTTATCGTTTTCCGGACAAAGACAGCTTTTGCATGCACTATGAC (SEQ ID NO:128)

The DNA sequences of the oligonucleotide pair used to make the cassette to introduce the MM021 peptide into the chymotrypsin reactive site loops of the p2JM103-lnk2-BBI expression vector are provided below. The cassette was ligated into the SphI and SalI restriction sites in the vector.

MM021 (2$^{nd}$ loop)
(SEQ ID NO:129)
CAAAAGCTGTGCTTGTAAACACAACGTACGTCTTTTATGTTTTTGCG
and (SEQ ID NO:130)
TCGACGCAAAAACATAAAAGACGTACGTTGTGTTTACAAGCACAGC

TTTTGCATG

Libraries made of cysteine constrained peptides are popular reagents (e.g. the commercially available PhD-C7C Phage Display Peptide Library Kit; NEB) for selecting peptides that bind to substrates of interest. BBI has two cysteine constrained reactive site loops that are structurally similar to the peptide loops displayed in various methods used to select peptide binders. So, once a cysteine constrained binding peptide has been selected, BBI is suitable for use as a scaffold to present the peptide in a binding reaction.

The VegF binding peptide CK37281 (See e.g., co-pending U.S. Provisional Patent Application Ser. No. 60/520,403, filed Nov. 13, 2003, incorporated herein by reference) was grafted into BBI by replacing the trypsin, chymotrypsin, or both reactive site loops, with the CK37281 peptide sequence (ACYNLYGWTC)(SEQ ID NO:9) by using DNA oligonucleotide cassettes. To facilitate the construction, an EcoRI site was introduced in the coding region of the BBI gene (custom synthesized by Operon Technologies; See, Example 1) between the trypsin and chymotrypsin reactive site loops by QuikChange® site-directed mutagenesis, using methods described by the manufacturer (Stratagene) using the primers BowBeco-F and BowBeco-R, shown above (0.5 pmol of each primer was used in the QuikChange® reaction; after an initial denaturation step of 97° C. for 3 minutes, 18 PCR cycles of 68° C. for 12 minutes, 95° C. for 30 seconds and 55° C. for one minute, followed by a final extension reaction for 15 minutes at 68° C.).

To replace the trypsin inhibitory peptide loop, two DNA oligonucleotides (IBBCK81+ and IBBCk81−) were annealed and ligated into the SacI and EcoRI restriction sites. Likewise, to replace the chymotrypsin inhibitory peptide loop, EcoRI and SalI sites were used for insertion of a DNA cassette made by annealing the oligonucleotides (2BBck81+ an 2BBck81−). The CK37281 peptide was grafted into both loops by inserting the CK37281 peptide in the chymotrypsin loop (using the oligonucleotides (2BBck81+ an 2BBck81−) after the trypsin loop was first replaced by the CK37281 peptide. BBI with the CK37281 peptide in the trypsin loop (1BBIck81) was moved into the pJM103BBI expression vector as a SacI-SphI fragment. BBI with the CK37281 in the chymotrypsin loop (2BBIck81), or both loops (12BBIck81), was moved into pJM103BBI as SacI-SalI fragments. The correct sequences were verified by DNA sequencing (the sequence of 12BBIck81 gene is shown in FIG. 3). The resulting vectors, pJM103-1BBIck81, pJM103-2BBIck81, or pJM103-12BBIck81, were used to transform *B. subtilis* BG3934comK, and the production of the BCE fusion proteins was determined as in Example 1 above.

The fusion protein running at ~44 kDa was detected by SDS-PAGE to be the major protein present in the cell free broth. Although in some cases, there was significant degradation (up to 50%) of the BBI moiety (especially after >48 h of growth in MBD medium), as observed by the presence of a prominent protein band running at ~34 kDa corresponding to the BCE103 catalytic core. In these cases, the titers of the BCE103 cellulase were similar to that measured with fusions to the wild-type BBI (Example 1), but the activity of the BBI (trypsin inhibition with 2BBIck81, or chymotrypsin inhibition with 1BBIck81) was generally about two fold less.

To reduce the proteolytic degradation of BBI variants during growth (i.e. decrease the amount of BCE103 cellulase core present on SDS-PAGE gels in comparison to the fusion protein), a *Bacillus subtilis* strain with nine protease genes deleted, BG6006 (degU$^{Hy}$32, oppA, ΔspoIIE3501, ΔaprE, ΔnprE, Δepr, ΔispA, Δbpr, Δvpr ΔwprA, Δmpr-ybjF, ΔnprB, amyE::xylRPxylAcomK-ermC), was used as an expression host, and the growth temperature (35° C.) and aeration (200 rpm) were reduced. With these changes, a major fusion protein band (~44 kDa) was observed on SDS-PAGE gels with an insignificant band present at the molecular weight expected for the BCE catalytic core protein (~34 kDa).

In addition to the CK37281 peptide, a number of other cysteine constrained peptides were produced when substituted into the trypsin and/or chymotrypsin reactive site loops of BBI fused to the C-terminus of the BCE103 cellulase. Specific examples included:

(1) Peptides designed or selected as complement antagonists, compstatin introduced into the 1$^{st}$ or 2$^{nd}$ reactive site loops (See, Sahu et al., J. Immunol., 157: 884-891, [1996]), C2c (1$^{st}$ loop), C3c (1$^{st}$ loop), C4c (1$^{st}$ loop) and C5c (1$^{st}$ loop); or peptides selected in a Factor B binding reaction 1B, 2B, 4A, 5A, 6-1A, 7A, 8B, 9A, 10B, 11-1A, 12B, 13A, and 15-1A (all in 2$^{nd}$ loop);

(2) Peptides designed to bind to the proteases Factor Xa or stratum corenum chymotrypsin, XaI (2$^{nd}$ loop) or hSCC1 (1$^{st}$ loop), respectively;

(3) Peptides selected in FGF5 binding reactions 1A6 (1$^{st}$ or 2$^{nd}$ loop), 1C2 (1$^{st}$ or 2nd loop), (1$^{st}$ or 2$^{nd}$ loop), 2E5 (1$^{st}$, 2$^{nd}$ or both loops), FGFns (1$^{st}$ or 2$^{nd}$ loop), FGFkr (1$^{st}$ or 2$^{nd}$ loop), FGFhl (1$^{st}$ or 2$^{nd}$ loop), FGFgy (1$^{st}$ or 2$^{nd}$ loop), MM005 (1$^{st}$ or 2$^{nd}$ loop), MM007 (1$^{st}$, 2$^{nd}$ or both loops), MM009 (2$^{nd}$ loop), MM010 (1$^{st}$, 2$^{nd}$ or both loops), MM017 (2$^{nd}$ loop), FGFps1 (2$^{nd}$ loop), FGFps2 (1$^{st}$, 2$^{nd}$ or both loops), and FGFpsB (2$^{nd}$ loop); and (4) Peptides selected in TGFβ-1 binding reactions 1A8 (2$^{nd}$ loop), 1A12 (2$^{nd}$ loop), 1E11 (2$^{nd}$ loop), TGFps1 (2$^{nd}$ loop), and MM021 (2$^{nd}$ loop).

The oligonucleotides used to introduce these peptides into either the trypsin (1$^{st}$ loop) or chymotrypsin (2$^{nd}$ loop) reactive site loops, and methods used to graft these peptides into BBI, are provided above. In all cases, fusion proteins were produced as determined by SDS-PAGE gels. However, with some substituted peptides, the amount of intact fusion protein was increased by reducing the proteolytic degradation as described above for the CK37281 substituted peptide.

Example 3

Activation of BBI by Thiol Reducing/Oxidizing Agents

After growth, the activity of the BBI (by trysin or chymotrypsin inhibition) is typically some 5-20 times lower than what would be expected from the activity of the BCE103 cellulase measured in the cell free supernatants (the two molecules should be present at a 1:1 molar ratio in the fusion protein). An increase in the activity of BBI (measured by either trypsin or chymotrypsin inhibition) in the BCE103-BBI fusion protein can be routinely obtained by adding bME, typically concentrations of 1-4 mM added to the MBD growth medium about 14 h after inoculation. The trypsin or chymotrypsin inhibitory activity of BBI in the fusion protein is also lower than expected when binding peptides (e.g. VegF binding peptide CK37281) replace the chymotrypsin or trypsin reactive site loop, respectively. As with the wild-type BBI, the inhibitory activity can be increased by treatment with bME. Unexpectedly, other thiol reducing agents (e.g., cysteine, reduced glutathione, DL-dithiothreitol and Tris[2-carboxyethyl]phosphine) had small or negligible effects on the activation of BBI during growth in these experiments. Also, additions of antioxidants (e.g., ascorbic acid or DL-α-tocopherol acetate) or other adjuvants to the growth medium (e.g., isoleucine, soybean oil, Tween-80), or growth at 30° C. did not significantly improve the BCE103:BBI activity ratio.

Figure 4:
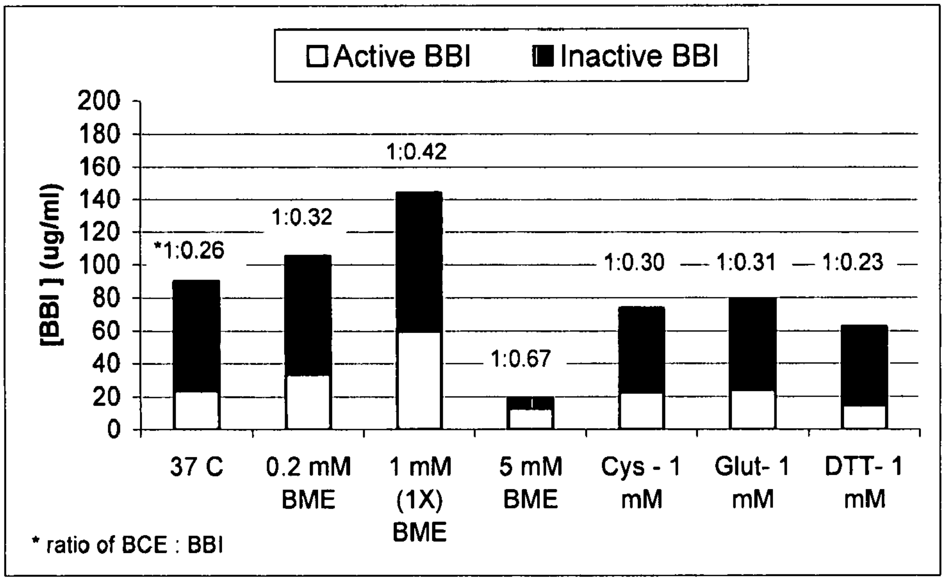
FIG. 4 provides a graph showing titers of active versus inactive 2BBIck81 (by trypsin inhibition) and the ratio of the activities of BCE103 cellulase to 2BBck81 with various thiol reducing agents added during the growth of the culture. In this Figure, BME=2-mercaptoethanol, Cyt=cysteine, Glut=reduced glutathione, DTT=dithiothreitol).

Specifically, to determine the BBI activation during growth, cultures of *B. subtilis* BG6006 transformed with p2JM103-E3-2BBIck81 (See, Example 4, below) were grown in 40 ml MBD medium in 250 ml shake flasks at 37° C. for 13 h. Then, the thiol reducing agents indicated on the graph in FIG. 4 were added and cell sup ematants harvested after 62 h of growth. The reagents 2-mercaptoethanol (BME), cysteine (Cys), reduced glutathione (Glut), and DL-dithiothreitol (DTT) were added to the growth medium to the final concentrations indicated on the graph provided in FIG. 4. Concentrations of 5 mM βME can result in better BCE 103: BBI activity ratios but typically result in an overall decrease in both BCE103 and BBI titers (see FIG. 4), at least partially due to the reduction in bacterial growth caused by the added reagent. Titers of BCE103 and 2BBIck81 were determined using the assays described in Example 1.

BBI activation was also achieved after partial purification of the fusion proteins (e.g. BCE-lnk2-2BBIck81, see Example 4 below) by Q-Sepharose ion exchange chromatography.

The fusion protein was purified from cell free broth obtained from shake flasks or fermentor runs. The broth was filtered, diluted five to ten fold in water and the pH adjusted to pH 7.5-8.0. The diluted sample was loaded onto a column packed with Q-Sepharose resin (GE Healthcare). The column was washed with 50 mM Tris pH 7.5 and then washed again in the same buffer containing 300 mM NaCl. The fusion protein was eluted in the same buffer with 700 mM NaCl.

To activate the BBI, the pooled fusion protein fractions were diluted ten fold in Assay Buffer then treated with 2 mM βME and 0.2 mM oxidized glutathione (GSSG) with constant mixing on a stir plate or rocker platform for about 24 h at room temperature. The BBI could generally be activated to about 70-100% of the expected trypsin inhibitory activity based on the measured concentration of the BCE103 cellulase. Although the activation method outlined above generally yielded the best results, in some cases, in order to maximize the activation of a given sample, screens were performed in 96-well plates to determine the optimal conditions. Initially, the typical conditions screened were the dilution in Assay Buffer (e.g., a 2-50 fold dilution series), βME concentration (e.g., series between 0.5-5 mM) and oxidized glutathione concentration (e.g. 0 mM then a series of 1/20 to 1/2 the βME concentration).

Figure 5:
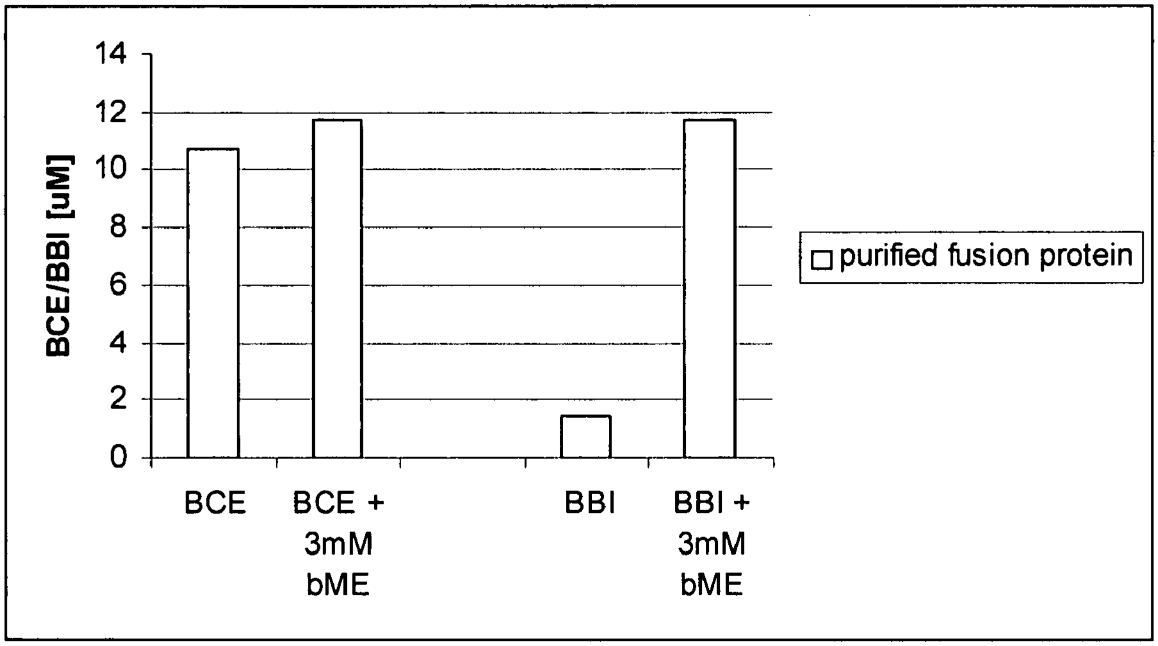
FIG. 5 provides a graph showing activation of BCE-lnk2-2BBIck81 with 2-mercaptoethanol (bME) after partial purification by ion exchange chromatography.

The activation of the fusion protein BCE-Ink2-2BBIck81 is shown in FIG. 5. In this specific example, the fusion protein from a Q-Sepharose purification was diluted 1:10 in Dulbecco's PBS (Mediatech) with 0.005% TWEEN®-80. Beta-mercaptoethanol was added to a final concentration of 3 mM and incubated overnight at room temperature on a rocker. The sample was further incubated at room temperature for about 60 h with vigorous stirring on a magnetic stir plate. The titers of the BCE103 and 2BBIck81 (before and after βME treatment) were determined by cellulase assays and trypsin inhibitory assays, respectively.

In some embodiments, such as for activating BBI or it variants in cell free broth from large volume fermentations, it is desirable to reduce the dilution and βME concentration in the activation reaction. This can be accomplished by using higher concentrations of buffer (500 mM Tris pH 8.6), or changing to zwitterionic buffers such as CHES (also CAPS, Tricine, TAPS, and other suitable zwitterionic buffers). For example, cell free broth (or fusion protein fractions purified by ion exchange chromatography) was diluted 1:1 in 375 mM CHES pH 8.6 with 0.005% TWEEN®-80 then activated with 1 mM βME and 10 mM $Na_2SO_3$ and incubated with stirring at room temperature for about 24 h. BBI or its variants, as BCE103 cellulase fusion proteins, were routinely activated by this method to 70-100% of the expected value (based on BCE103 cellulase activities).

Example 4

Release of Free BBI/Variants by Cleavage of the BCE103-BBI Fusion Proteins

This Example describes experiments developed to release free BBI or its variants by cleavage of the BCE103-BBI fusion proteins.

The sequences of the DNA oligonucleotide pairs that were annealed and ligated into the BamHI and SacI sites of pJM103-BBI to generate potential cleavage sites during culture growth between the BCE103 catalytic domain and BBI are provided below.

```
BCEsubBBI
(a subtilisin-type sensitive peptide sequence)
                                           (SEQ ID NO:131)
GATCCAGGTGGAGCTGCTTTAGTTGACGATGAGAGCT
and

                                           (SEQ ID NO:132)
CTCATCGTCAACTAAAGCAGCTCCACCTG

BCEcbdLBBI
(a portion of the 1st CBD)
                                           (SEQ ID NO:133)
GATCCAGGTGAACCTGACCCAACTCCTCCATCTGATCCTGGAGAATACCC

AGCTTGGGACGATGAGAGCT
and

                                           (SEQ ID NO:134)
CTCATCGTCCCAAGCTGGGTATTCTCCAGGATCAGATGGAGGAGTTGGGT

CAGGTTCACCTG

BCEproBBI
(the entire pro peptide of BBI)
                                           (SEQ ID NO:135)
GATCCGGCGAACCTGCGTCTGTCTAAGCTTGGCCTGCTTATGAAATCAGA

CCATCAGCACAGCAATGACGATGAGAGCT
and

                                           (SEQ ID NO:136)
CTCATCGTCATTGCTGTGCTGATGGTCTGATTTCATAAGCAGGCCAAGCT

TAGACAGACGCAGGTTCGCCG

BCEshortproBBI
(a C-terminal portion of the pro peptide of BBI)
                                           (SEQ ID NO:137)
GATCCAAAATCAGACCATCAGCACAGCAATGACGATGAGAGCT
and

                                           (SEQ ID NO:138)
CTCATCGTCATTGCTGTGCTGATGGTCTGATTTTG
```

The sequences of the DNA oligonucleotide pair that was annealed and ligated into the BamHI and SacI sites of p2JM 103-BBI to fuse BBI to the $2^{nd}$ CBD linker of BCE103 cellulase are provided below.

```
BCEcbdDBBI
                                           (SEQ ID NO:139)
GATCCAGGAGAAGCGGACCCAACGCCCCCAAGTGATCCAGGAGAGTATCC

AGCATGGGATTCAAATCAAATTTACACAAATGAAATTGTGTATCATAACG

GTCAGTTATGGCAAGCGAAATGGTGGACACAAAATCAAGAGCCAGGTGAG

CCATACGGTCCGTGGGAACCACTCAAATCTGACCCAGATTCAGAGGA

TGAGAGCT
and

                                           (SEQ ID NO:140)
CTCATCGTCTGAATCTGGGTCAGATTTGAGTGGTTCCCACGGACCGTATG

GGTCACCTGGCTCTTGATTTTGTGTCCACCATTTCGCTTGCCATAACTGA

CCGTTATGATACACAATTTCATTTGTGTAAATTTGATTTGAATCCCATGC

TGGATACTCTCCTGGATCACTTGGGGGCGTTGGGTCCGGTTCTCCTG
```

The peptide sequences susceptible to acid cleavage between aspartic acid and proline residues are provided below.

| | | |
|---|---|---|
| Linker 1- WGDPHY | (SEQ ID NO:141) | (Lidell et al., J. Biol. Chem. 278:13944-51 [2003]) |
| Linker 2- DNNDPI | (SEQ ID NO:142) | (Segalas et al., FEBS Lett., 371:171-175 [1995]) |
| Linker 3- VVADPN | (SEQ ID NO:143) | (Kemperman et al., Appl. Env. Microbiol., 69: 1589-1597 [2003]) |

Oligonucleotide primers used to introduce a BssHH site into pJM 103BBI by QuikChange® site-directed mutagenesis are provided below.

```
                                           (SEQ ID NO:144)
BCEbss-F 5'-TGGCGTTCAGCAACATGAGCGCGCAGGCTGATGATTA

                                           (SEQ ID NO:145)
BCEbss-R 5'-TAATCATCAGCCTGCGCGCTCATGTTGCTGAACGCCA
```

Sequences of the DNA oligonucleotides that were annealed as a cassette (SalI-HindIII) to introduce HindIII and XhoI sites after the stop codon of BBI, to introduce a PacI site after the LAT, and remove the original HindIII site are provided below.

```
BCEterm+                                   (SEQ ID NO:146)
5'-GACATCACGGACTTCTGCTATGAGCCATGTAAACCAAGCGAGGACGA

TAAAGAGAACTAAAAGCTTAACTCGAGGTTAACAGAGGACGGATTTCCTG

AAGGAAATCCGTTTTTTTATTTTTAATTAAG

BCEterm+                                   (SEQ ID NO:147)
5'-AGCTCTAATTAAAAATAAAAAAACGGATTTCCTTCAGGAAATCCGTC

CTCTGTTAACCTCGAGTTAAGCTTTTAGTTCTCTTTATCGTCCTCGCTTG

GTTTACATGGCTCATAGCAGAAGTCCGTGATG
```

PCR primers used to generate the acid labile linkers provided above (i.e., Linker 1, Linker 2, and Linker 3) inserted between the BCE103 catalytic domain and BBI are provided below.

```
BCE103coreBssHII_FW
5'-CAGCAACATGAGCGCGCAGGCTG          (SEQ ID NO:148)

linkerWGDPHY_RV                     (SEQ ID NO:149)
5'-ATCGTCTGGATCCGGATAGTGGGGGTCTCCCCAAGATGCTGATTCTC
TTATTTTTCCC

linkerDNNDPI_RV                     (SEQ ID NO:150)
5'-ATCGTCTGGATCCGGTATGGGATCATTGTTGTCAGATGCTGATTCTC
TTATTTTTTCCC

linkerVVADPN_RV                     (SEQ ID NO:151)
5'-ATCGTCTGGATCCGGGTTGGGATCTGCAACTACAGATGCTGATTCTC
TTATTTTTCCC
```

PCR primers used to generate the acid labile linkers provided above (i.e., Linker 1, Linker 2, and Linker 3) inserted into the 1$^{st}$ CBD linker.

```
BCE103corePstI_FW
GCATAAGGAT GAGTCATCTG CAGCG         (SEQ ID NO:152)

LplusWGDPHY_RV                      (SEQ ID NO:153)
5'-ATCGTCTGGATCCGGATAGTGGGGGTCTCCCCACGGTTCTCCTGGAT
CAGATGGCGG

LplusDNNDPI_RV                      (SEQ ID NO:154)
5'-ATCGTCTGGATCCGGTATGGGATCATTGTTGTCCGGTTCTCCTGGAT
CAGATGGCGG

LplusVVADPN_RV
                                    (SEQ ID NO:155)
5'-ATCGTCTGGATCCGGGTTGGGATCTGCAACTACCGGTTCTCCTGGAT
CAGATGGCGG
```

Protein sequence of the acid labile linkers inserted between the BCE103 catalytic domain and BBI are provided below. The acid labile linkers are shown in bold type and the sequences from the first CBD domain are underlined.

Linker 1
BCE-WGDPHY-<u>PDP</u>-BBI (SEQ ID NO: 156)

Linker 2
BCE-DNNDPI-<u>PDP</u>-BBI (SEQ ID NO: 157)

Linker 3
BCE-VVADPN-<u>PDP</u>-BBI (SEQ ID NO: 158)

LinkerPlus 1
BCE-<u>IPPSDPTPPSDPGEP</u>-WGDPHY-<u>PDP</u>-BBI (SEQ ID NO: 159)

LinkerPlus 2
BCE-<u>IPPSDPTPPSDPGEP</u>-DNNDPI-<u>PDP</u>-BBI (SEQ ID NO: 160)

LinkerPlus 3
BCE-<u>IPPSDPTPPSDPGEP</u>-VVADPN-<u>PDP</u>-BBI (SEQ ID NO: 161)

The sequences of the DNA oligonucleotide pairs that were annealed and ligated into the BamHI and SacI sites of pJM103-BBI to generate potential cleavage sites between the BCE103 catalytic domain and BBI during the purification process are provided below.

```
BCEentBBI
(Enteropeptidase cleaveage site)
                                    (SEQ ID NO:162)
GATCCAGGTGGAGACGACGATGACAAAGACGATGAGAGCT
and
                                    (SEQ ID NO:163)
CTCATCGTCTTTGTCATCGTCGTCTCCACCTG

BCEgenen1BBI
(Genenase I cleavage site)
                                    (SEQ ID NO:164)
GATCCAGGTGCTGCTCATTACGACGATGAGAGCT
and
                                    (SEQ ID NO:165)
CTCATCGTCGTAATGAGCAGCACCTG
```

The sequences of the DNA oligonucleotide pairs that were annealed and ligated into the BamHI and SacI sites of pJM103-lnk2-1BBIck81 to generate potential cleavage sites between the BCE103 catalytic domain and BBI during the purification process are provided below.

```
BCEfurinBBI (Furin/Blisterase cleavage site)
                                    (SEQ ID NO:166)
GATCCACGTGCTAAAAGAGACGATGAGAGCT
and
                                    (SEQ ID NO:167)
CTCATCGTCTCTTTTAGCACGTG

BCEgenen2BBI (Genenase I cleavage site)
                                    (SEQ ID NO:168)
GATCCAGGCGCTGCACACTACAACGACGATGAGAGCT
and
                                    (SEQ ID NO:169)
CTCATCGTCGTTGTAGTGTGCAGCGCCTG

BCEfleBBI (Mpr cleavage site)
                                    (SEQ ID NO:170)
GATCCATTCCTTGAAGACGATGAGAGCT
and
                                    (SEQ ID NO:171)
CTCATCGTCTTCAAGGAATG
```

Sequences of the oligonucleotide primer pairs used to introduce the E and E3 linkers in Linker 2 by QuikChange site-directed mutagenensis (Stratagene) are provided below.

```
BCE-Elnk-BBI (Mpr cleavage site)
                                    (SEQ ID NO:172)
CCCATACCGGAGCCAGACGATGAGAGCTC
and
                                    (SEQ ID NO:173)
CATCGTCTGGCTCCGGTATGGGATCATTGTTG
```

The protein sequence of the E3 linker between the BCE103 catalytic domain and BBI was DNNDPIPEPDDESFNMPIPEP (SEQ ID NO:174). In this sequence, the E Linker is underlined and the sequence generated by faulty recombination in *E. coli* is shown in bold type. Cleavage by Mpr (or V8 protease) can occur after any of the three glutamic acids present in the E3 Linker. Thus, the structure was BCE-(SEQ ID NO:174)-BBI.

The sequences of the DNA oligonucleotide pairs that were annealed and ligated into the BamHI and SacI sites of p2JM103-lnk2-2BBIck81 to generate potential Genenase I cleavage sites between the BCE103 catalytic domain and BBI are provided below.

```
BCEgenen3BBI
                                    (SEQ ID NO:175)
GATCCAGGCGCTGCACACTACAAATCAGACCATCAGCACAGCAATGACGA

TGAGAGCT
and

                                    (SEQ ID NO:176)
CTCATCGTCATTGCTGTGCTGATGGTCTGATTTGTAGTGTGCAGCGCCTG

BCEgenen4BBI
                                    (SEQ ID NO: 177)
GATCCAGGCGCTGCACACTACGTAGAATTTCAAGACGATGAGAGCT
and

                                    (SEQ ID NO:178)
CTCATCGTCTTGAAATTCTACGTAGTGTGCAGCGCCTG
```

The protein sequence of a Genenase I sensitive cleavage site (also acid and Mpr sensitive) inserted between the BCE103 catalytic domain and BBI was DNNDPIPDP-GAAHYVEFQ (SEQ ID NO:179). The Genenase I site (Gen4 Linker) is in bold type (cleavage occurs between the tyrosine and valine) (NEB) and Linker 2 is underlined. Cleavage by Mpr can also occur after the glutamic acid that follows the valine in the Gen4 linker. The sequence used herein was BCE-SEQ ID NO:179)-BBI Cleavage sites in the BCE103-lnk2-2BBIck81 fusion protein are indicated below. The C-terminal seven amino acids of the BCE103 catalytic domain (underlined), linker 2 sequence (bold type), and 2BBIck81 sequences are shown. The acid/heat labile Asp-Pro bonds are indicated with solid headed arrows and the Mpr sensitive bonds after glutamic acids are indicated with line headed arrows.

(SEQ ID NO:180)

…KIRESASDNNDPIPDPDDESSKPCCDQCACTKSNPPQCRCSDMRL

NSCHSACKSCACYNLYGWTCFCVDITDFCYEPCKPSEDDKEN

In order to isolate free BBI or its variants, the BBI moiety needs to be cleaved from the BCE103-BBI fusion protein. In some embodiments, this is accomplished during growth, by proteases intrinsically produced by *B. subtilis*. In some alternative embodiments, this cleavage occurs after growth, during the purification process (e.g. by acid/heat or proteolytic cleavage). Linkers potentially susceptible to cleavage during growth were designed (See, above, sub, cbdL, pro, shortpro, and cbdD) and cloned into the pJM103BBI or p2JM103BBI expression vectors as BamHI-SacI cassettes. The production of fusion protein versus BCE103 catalytic domain was analyzed on SDS-PAGE gels as described in Example 1.

Little cleavage of the fusion protein was observed for all these linkers except with the pro linker, which was nearly completely cleaved so that very little intact fusion protein was observed on gels, although there was a large band corresponding to the BCE103 catalytic core. Unfortunately, this cleavage during growth resulted in negligible BBI activity measured in cell free supernatants and no BBI band could be identified on SDS-PAGE gels. Although it is not intended that the present invention be limited to any particular mechanism or theory, it is possible that the BBI is particularly sensitive to proteolytic degradation in its inactive form. Thus, cleavage during the purification process after activation is generally preferred.

In some embodiments, the bonds between aspartic acid and proline residues are cleaved by heat treatment at acidic pH as known in the art (See e.g., Landon, Meth. Enzymol., 47:145-149 [1977]). The 1st CBD linker in the BCE103 cellulase has three Asp-Pro dipeptide sequences (See, FIG. 1) with the potential to be cleaved by acid/heat treatment. However, cleavage by acid/heat treatment at these sites was found to be inefficient. Protein sequences that are especially labile to acid/heat have been described in the literature, three of such sequences are WGDPHY (SEQ ID NO:141), DNNDPI (SEQ ID NO:142), and VVADPN (SEQ ID NO:143)(i.e., Linkers 1, 2 and 3).

Before these acid labile linkers were introduced into the BCE103-BBI expression vector, pJM103BBI, a BssHII site was introduced by QuikChange® XL (Stratagene) mutagenesis (using the manufacturer's methods; and described in Example 2 above, except 8 minute extension and 1 minute denaturation steps were used) in the aprE signal sequence coding region using the oligonucleotide primers BCEbss-F and BCEbss-R (provided above). Then, HindIII and XhoI sites were inserted in front of the LAT terminator (after the BBI stop codon) and a PacI site was added after the terminator (the original HindIII site after the LAT terminator was removed) by inserting an oligonucleotide cassette (BCEterm+ and BCEterm−; provided above) into the SalI and the original HindIII sites. This new vector was called "p2JM103BBI."

The acid labile linker fragments were generated by PCR, using forward primer BCE103coreBssHII_FW with each of the reverse primers, linker WGDPHY_R, linker DNNDPI_RV, or linkerVVADPN_RV (the sequences of which are all provided above) and p2JM103BBI as the template (see Example 1 for the PCR protocol). The PCR fragments of 970 bp were digested with BamHI and PstI, the 154 bp fragments encoding the acid linker fragments were isolated from an agarose gel after electrophoresis, and ligated into the p2JM103 vector digested with BamHI and PstI that had also been purified from a gel. The linker sequences in the final expression vectors, p2JM103lnk1-BBI, p2JM103lnk2-BBI and p2JM103lnk3-BBI, were verified by DNA sequencing.

Competent *B. subtilis* strain BG3934comK or BG6006 were transformed with the plasmids, colonies selected on 5 μg/ml chloramphenicol LA plates and amplified to 25 μg/ml chloramphenicol as described in Example 1.

Similarly, the acid labile linkers were inserted into the first CBD linker. Specifically, PCR fragments were generated using the forward primer BCE103corePstI_FW with the reverse primers LplusWGDPHY_RV, LplusDNNDPI_RV, or LplusVVADPN_RV (See above, for the sequences) with p2JM103BBI as a template. The PCR fragments of about 150 bp were digested with BamHI and PstI, purified and ligated to the p2JM103BBI vector digested with BamHI and PstI. The correct sequences were verified by DNA sequencing and the plasmids p2JM103pllnk1-BBI, p2JM103pllnk2-BBI and p2JM103pllnk3-BBI were used to transform *B. subtilis* strains as described above.

After growth in MBD medium, the fusion proteins were purified by ion exchange chromatography essentially as described above (See, Example 2). The fusion protein was cleaved by treatment at 55° C. for 16 h in 10% formic acid. The BCE103 catalytic domain precipitated during the acid treatment and was removed by centrifugation. The free BBI in the supernatant was dried overnight on a SpeedVac. The sample was suspended in 50 mM Tris pH 8 before loading on the SDS-PAGE gel. By analysis of the protein stained SDS-PAGE gels, it was observed that acid cleavage was much more efficient in the fusion proteins where Linker 2 was inserted between the BCE103 catalytic domain and BBI (BCE-DNNDPI-PDP-BBI). This linker was found to be cleaved in a couple of hours at 75° C. in 20 mM glycine pH 2.

In alternative embodiments, the fusion protein was cleaved by treatment with a protease during the purification process. Linkers were designed with cleavage sites for glutamic acid specific proteases (e.g., Mpr or V8 protease), Furin/blisterase, Genenase I, and Enteropeptidase (Enterokinase). These linkers were introduced as oligonucleotide cassettes (See above, for the sequences) between the BCE103 catalytic core and BBI in the expression vector using the BamHI and SacI sites (See, FIG. 1). In the coding region of the original expression vector (pJM103BBI), there is a glutamic acid residue in the 1st CBD domain and at the third residue in BBI (See, FIG. 1), which is contemplated to be susceptible to cleavage by glutamic acid specific proteases such as *B. subtilis* Mpr (BsMpr) or V8 protease. However, neither BsMpr nor V8 protease were found to cleave the BCE-BBI fusion protein very efficiently at these sites. Thus, it was necessary to design other linkers that were susceptible to cleavage by these proteases.

The six acid labile linkers described above were tested for cleavage by BsMpr. These fusion proteins were cleaved by treatment for 16 h with 16 μg of BsMpr at room temperature. After cleavage, the BCE103 catalytic domain was precipitated by the addition of 10% formic acid and removed by centrifugation. The free BBI in the supernatant was dried overnight on a SpeedVac. The sample was suspended in 50 mM Tris pH 8, before loading on the SDS-PAGE. Similar to the acid cleavage, the BCE-DNNDPI-PDP-BBI (Linker 2) fusion protein was much more efficiently cleaved by BsMpr than any of the other linkers. Therefore, BBI and its variants were found to be effectively released from the BCE-DNNDPI-PDP-BBI fusion protein either by acid/heat treatment or proteolytic digestion with a glutamic acid specific protease such as BsMpr. Several other linkers designed for cleaved by Mpr (e.g., E, E3 linker, and fle, provided above) were tested but none of them had any advantages over Linker 2 (the E3 linker was generated by faulty recombination in *E. coli* after transformation with the QuikChange® site-directed mutagensis reaction designed to construct the E linker). As shown above, there are two acid/heat labile cleavage sites in Linker 2 and three sites sensitive to cleavage by Mpr.

Linkers designed for cleavage by Furin or Blisterase (NEB) (BCEfurinBBI), or Enteropeptidase (Enterokinase, NEB) (BCEentBBI) were tested, but none of these sequences were cleaved efficiently by the appropriate protease. Four linkers were also designed (BCEgenen1BBI, BCEgenen2BBI, BCEgenen3BBI, and BCEgenen4BBI) and tested for cleavage by Genenase I (NEB). Efficient cleavage of the fusion protein was observed only with the Gen4 Linker (BCEgenen4BBI). BsMpr was also found to efficiently cleave the Gen4 linker.

After activation of the purified BCE-lnk2-2BBIck81 fusion protein, cleavage by BsMpr does not go to completion as judged by SDS-PAGE gels. However, it was discovered that complete cleavage after activation of BCE-BBI fusion proteins with Linker 2 (or the Gen4 linker) can be accomplished by using the Mpr protease isolated from *Bacillus licheniformis* (BlMpr). While it is not intended that the present invention be limited to any particular mechanism, cleavage after the third amino acid in mature BBI appeared to be more sensitive to BlMpr while cleavage after the sixth amino acid from the C-terminus of BBI is more sensitive to BsMpr cleavage.

In some embodiments, after cleavage, the BBI is purified away from the BCE103 catalytic domain by selective acid precipitation (pH 3 or lower) of the BCE103 catalytic domain as described above, ion exchange chromatography (See, Example 5), or by selective binding of BBI on an anhydrotrypsin-agarose (Sigma) column loaded in 50 mM Tris pH 8.0, washed with 50 mM Tris pH 8.0 with 150 mM NaCl, then eluting bound BBI with 50 mM glycine pH 2.2 with 300 mM NaCl).

Example 5

Binding of BBIck81 to VegF

In this Example, experiments conducted to assess the binding of BBIck81 to VegF are described. The BCE103-lnk2-2BBIck81 fusion protein was produced in *B. subtilis* as described in Example 2. The fusion protein was purified, and the BBI trypsin inhibitory activity was increased by treatment with βME and oxidized glutathione as described in Example 3. The fusion protein was cleaved by BsMpr protease (See, Example 4) and the free 2BBIck81 was purified from the BCE103 catalytic domain by ion exchange chromatography using a Q-Sepharose column.

Briefly, after cleavage, the pH of the cleaved sample was adjusted to 5.5, the sample was then loaded onto the column (equilibrated with 25 mM MES pH 5.5). The free 2BBIck81 was washed through the column using 25 mM sodium acetate pH 5.0 while the BCE103 catalytic core remained bound to the resin. The 2BBIck81 fraction was concentrated by ultrafiltration and analyzed using an electrochemiluminescence (ECL) based binding assay (BioVeris). The Anti-VegF antibody (Santa Cruz) and VegF (PeproTech) were labeled with the electrochemiluminescent dye and biotin, respectively, as described by the manufacturer (BioVeris). All materials were in Dulbecco's PBS (Mediatech) supplemented with 0.1% TWEEN®-80. An initial dilution series of Anti-VegF antibody (125, 250 and 500 ng/ml) and VegF (100, 150, 200 and 250 ng/ml) were tested in the binding assay to determine the concentrations of each that would give a robust ECL signal.

Figure 6:
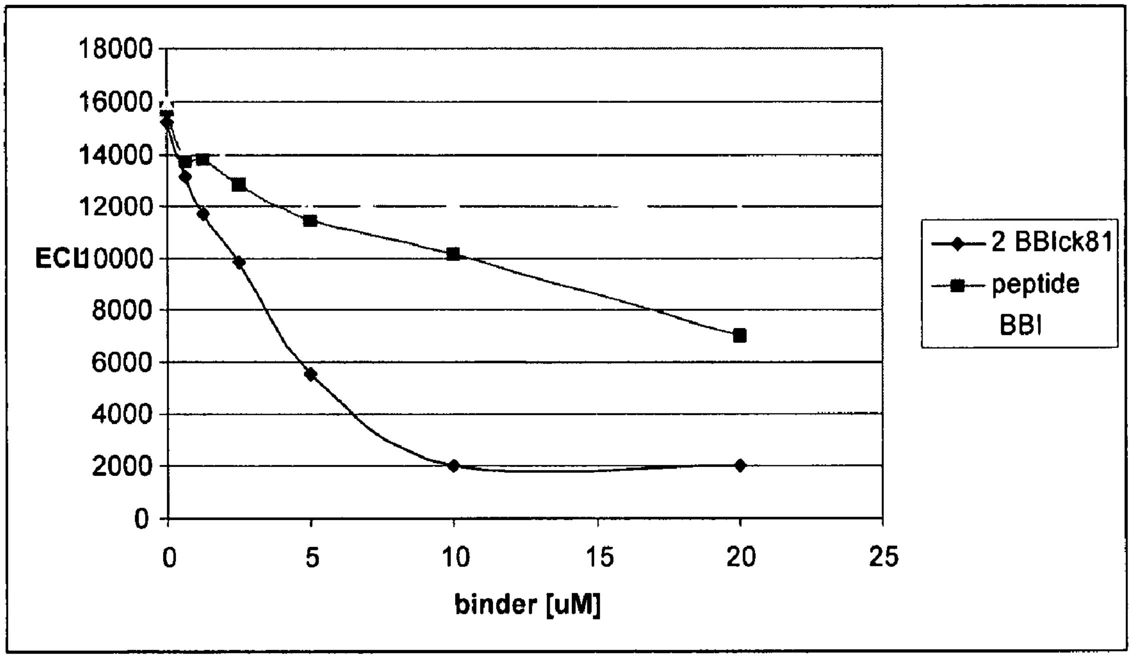
FIG. 6 provides a graph showing results from a competition analysis of 2BBlck81 versus anti-VegF antibody binding to VegF.

For testing 2BBIck81 binding, 50 μL of 500 ng/ml ECL labeled Anti-VegF antibody, 50 μL of 250 ng/ml biotinylated VegF and 100 μL 2BBIck81 (series of 12.5, 15, 31.25, 62.5, 125, 250 or 500 ng/ml) were incubated at room temperature for 2 h with shaking. Then, 50 μL of 0.2 mg/ml streptavidin coated beads were added and the reaction was incubated at room temperature for 30 minutes. The ECL signal was measured using a BioVeris M8/384 Analyzer as described by the manufacturer (BioVeris). As shown in FIG. 6, the ECL signal decreased as increasing concentrations of 2BBIck81 displaced more of the labeled Anti-VegF antibody bound to VegF attached to the magnetic beads.

Thus, the CK37281 peptide when grafted onto the chymotrypsin inhibitory loop of BBI (2BBIck81) competed with the Anti-VegF antibody for binding to VegF at micromolar concentrations. In fact, 2BBIck81 competed for VegF binding better than the synthesized CK37281 peptide itself (See, FIG. 6). The CK37281 peptide inserted into the trypsin inhibitory loop, 1BBIck81, also competed with the Anti-VegF antibody in the BioVeris assay. Thus, BBI was found to be useful as a scaffold to present active binding peptides selected by various screening methods.

Example 6

Use of Alternative Fusion Partners for the Production of 2BBIck81

In this Example, experiments conducted to evaluate alternative fusion partners are described. The DNA sequence of the oligonucleotide primers used to amplify the dsbC gene (*E. coli*) from pET-40b(+) are provided below. These primers generate a BssHII site at the 5' end and a BamHI at the 3' end for cloning into p2JM103-Gen4-2BBIck81.

```
DsbCBBI-F                              (SEQ ID NO:181)
AACATGAGCGCGCAGGCTGATGACGCGGCAATTCAACAAACGTTAG

DsbCBBI-R                              (SEQ ID NO:182)
TCGTCTGGATCCGGTATGGGATCATTGTTGTCACCAGAACCACTAGTTGA

TCCTTTACCGCTGGTCATTTTTTGGTG
```

The DNA sequences of the oligonucleotides that were annealed together to make a cassette (Alw44I-BamHI) for fusing the *P. mendocina* cutinase gene to BBI with Linker 2, are provided below.

```
CutinaseBBI+                           (SEQ ID NO:183)
TGCACTTCTCTGCTTTGGTCTGTTGAACGCAGAGGTCTTGACAACAATGA

TCCTATTCCG

CutinaseBBI                            (SEQ ID NO:184)
GATCCGGAATAGGATCATTGTTGTCAAGACCTCTGCGTTCAACAGACCAA

AGCAGAGAAG
```

Because the BBI moiety has seven disulfide bonds, it is contemplated that higher titers of active BBI will be obtained using fusion proteins other than the BCE103 cellulase catalytic domain. For example, in some embodiments, compositions such as thiol-disulfide oxidoreductases and/or protein disulfide isomerases find use as fusion proteins to help produce correctly folded BBI moieties. In this embodiment, no additional activation step is needed under most circumstances. In additional embodiments, other proteins produced at high titers in *B. subtilis* also find use as fusion partners. For example, the thermostable protein disulfide isomerase from the fungus *Humicola insolens* (hiPDI) has been used as a fusion partner to produce the light chain of immunoglobulin G (2 disulfides) in *Bacillus brevis* (See, Kajino et al., Appl. Env. Microbiol., 66:638-642 [2000]).

To determine whether hiPDI could be a better fusion partner than BCE103 for the production of BBI, this hiPDI gene was synthesized (DNA2.0) and cloned into the expression vector, p2JM103-lnk2-2BBIck81 (See, Example 4) as a BssHII-SacI fragment. In designing the synthetic gene, codons occurring with high frequency in highly expressed *B. subtilis* genes were selected except in cases where restriction sites were introduced or deleted. In the final construction, the N-terminus of the mature hiPDI gene was fused to the AprE signal sequence and the C-terminus was fused to a linker with an Enteropeptidase cleaveage site (Kajino et al., Appl. Env. Microbiol., 66:638-642 [2000]), which in turn was fused to 2BBIck81 (See, FIG. 7). This expression vector, p2JM-PDI-EK-2BBIck81, was used to transform *B. subtilis* BG6006 and the production of the fusion protein was determined in MBD medium (as described in Example 1) with or without 2 mM βME added 14 h after inoculation.

As determined by SDS-PAGE gels, the production of the PDI-2BBIck81 fusion protein was typically somewhat less than the BCE-2BBck81 grown under identical conditions. The BBI titers (trypsin inhibition) measured from the PDI-2BBIck81 cell free supernatants were also typically less than the BCE-2BBIck81 fusion. As with fusions to BCE103, the measured activities of BBI when fused to PDI were higher when grown in 2 mM βME and the BBI activity was increased by the addition of βME to the cell free supernatants after growth when grown in βME free medium (as described in Example 3). Thus, the thiol-disulfide oxidoreductase activity of PDI does not seem to significantly improve the titers of active 2BBIck81 in the fusion protein or obviate the need for activation of the BBI molecule.

In order to increase the reduction potential of the fusion protein, which was contemplated to improve the BBI titers during growth, DsbC from *Escherichia coli* was used as a fusion partner for 2BBIck81. The dsbC gene was amplified by PCR using Herculase Enhanced DNA polymerase as described by the manufacturer (Stratagene) using DsbCBBI-F and DsbCBBI-R as primers (sequences shown above) and pET-40b(+) (Novagen) as a template. The isolated PCR fragment was cloned into the vector p2JM103-Gen4-2BBIck81 (See, Example 4) as a BssHII-BamHI fragment. The correct sequence of the fusion gene was verified by DNA sequencing. In this case, the titers of the DsbC-2BBIck81 fusion protein were significantly lower than the BCE-2BBIck81 fusion protein as judged on SDS-PAGE gels and the titers of the active 2BBIck81 measured by trypsin inhibition were much lower as well.

Other proteins that are produced at high titers in *B. subtilis* find use as fusion partners for the production of BBI. One such protein is the cutinase from *Pseudomonas mendocina*, which has been expressed at high titers utilizing the aprE promoter from *B. subtilis* (See e.g., U.S. Pat. No. 5,429,950, herein incorporated by reference). The aprE-cutinase gene fusion as an EcoRI-Alw44I fragment (from pAK-15) was ligated with an Alw44I-BamHI linker oligonucleotide cassette (See, sequence above) into the p2JM103-lnk2-2BBIck81 (See, Example 4) that had been cut with EcoRI and BamHI. This cutinase-linker2-2BBIck81 expression vector (See, FIG. 8 for the EcoRI-BamHI aprE-cutinase-linker2 sequence) was used to transform *B. subtilis* BG6006 cells and the fusion protein was produced in MBD medium as described previously for the other fusion proteins (See, Example 1). In this case, the cutinase-linker2-2BBIck81 fusion protein was not the major band observed on SDS-PAGE gels and the measured lipase titers (as measured using the methods provided in U.S. Pat. No. 5,429,950) and BBI titers were much less (ca. 20 fold) than found with the BCE-2BBIck81 fusion protein. Also, the BBI titers in the cutinase fusion protein were not improved significantly when 3 mM βME was added to the growth medium. Thus, the highest titers of active 2BBIck81 was consistently obtained by activation of the BCE-2BBIck81 fusion protein. Nonetheless, it is contemplated that various fusion partners will find use in the present invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Having described the preferred embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. A method for producing a VEGF binding peptide in a protease inhibitor scaffold in a bacterial cell comprising, introducing a DNA construct into a bacterial cell, wherein said DNA construct comprises a heterologous DNA sequence encoding a protease inhibitor, said inhibitor being a Bowman-Birk Inhibitor (BBI) comprising SEQ ID NO: 13, wherein the trypsin and/or chymotrpsin loop of SEQ ID NO: 13 is replaced with a VEGF binding peptide consisting of SEQ ID NO: 9;

culturing said bacterial cell under suitable culture conditions to allow expression of the heterologous DNA sequence, and producing said VEGF binding peptide in a protease inhibitor scaffold.

2. The method of claim 1, further comprising recovering said VEGF binding peptide in a protease inhibitor scaffold.

3. The method of claim 2, further comprising the step of activating said VEGF binding peptide in a protease inhibitor scaffold.

4. The method of claim 3, wherein said activating is accomplished by exposing said VEGF binding peptide in a protease inhibitor scaffold to at least one reagent selected from the group consisting of compositions that reduce disulfide bonds, compositions that oxidize disulfide bonds, and compositions that alter the redox potential.

5. The method of claim 1, wherein said bacterial cell is a member of the genus *Bacillus*.

6. The method of claim 1, further comprising introducing into the bacterial cell a second nucleic acid sequence encoding a thiol disulfide oxidoreductase or chaperone.

7. The method of claim 1, wherein said VEGF binding peptide in a protease inhibitor scaffold is expressed as a fusion protein.

8. The method of claim 7, wherein said fusion protein further comprises a cellulase catalytic domain, a cleavage site, and said VEGF binding peptide in a protease inhibitor scaffold.

9. The method of claim 7, wherein said fusion protein is processed by a protease or acid/heat treatment to liberate said VEGF binding peptide in a protease inhibitor scaffold.

10. The method of claim 7, wherein the fusion protein further comprises at least one linker sequence.

11. The method of claim 10, wherein said linker sequence is selected from the group consisting of SEQ ID NOS:141-143.

12. An isolated polynucleotide encoding a Bowman-Birk Inhibitor (BBI) comprising SEQ ID NO: 13, wherein the trypsin and/or chymotrpsin loop of SEQ ID NO: 13 is replaced with SEQ ID NO: 9.

13. An expression vector comprising a polynucleotide sequence, wherein said polynucleotide sequence encodes a Bowman-Birk inhibitor comprising SEQ ID NO: 13, wherein the trypsin and/or chymotrypsin loop of SEQ ID NO: 13 is replaced with SEQ ID NO: 9.

14. A host cell transformed with the vector of claim 13.

15. The host cell of claim 14, wherein said host cell is a *Bacillus* species cell.

16. A method for producing a VEGF binding peptide in a protease inhibitor scaffold in a bacterial cell comprising, introducing a DNA construct into a bacterial cell, wherein said DNA construct comprises a heterologous DNA sequence encoding a protease inhibitor, said inhibitor being a Bowman-Birk Inhibitor (BBI) comprising SEQ ID NO: 13, wherein the trypsin and/or chymotrpsin loop of SEQ ID NO: 13 is replaced with a VEGF binding peptide consisting of SEQ ID NO: 9, and wherein SEQ ID NO: 13 is truncated at the N- and/or C-terminus, with as many as seven N-terminal residues up to the first cysteine (Cys8) and/or as many as nine C-terminal residues up to the last cysteine (Cys62) removed;

culturing said bacterial cell under suitable culture conditions to allow expression of the heterologous DNA sequence, and producing said VEGF binding peptide in a protease inhibitor scaffold.

* * * * *

UNITED STATES PATENT AND TRADEMARK OFFICE

CERTIFICATE OF CORRECTION

PATENT NO. : 7,413,877 B2
APPLICATION NO. : 10/984514
DATED : August 19, 2008
INVENTOR(S) : Collier et al.

It is certified that error appears in the above-identified patent and that said Letters Patent is hereby corrected as shown below:

In Column 111, Claim 1
On line 48, replace "chymotrpsin" with -- chymotrypsin --.

In Column 112, Claim 12
On line 64, replace "chymotrpsin" with -- chymotrypsin --.

In Column 113, Claim 16
On line 13, replace "chymotrpsin" with -- chymotrypsin --.

Signed and Sealed this

Twenty-fifth Day of November, 2008

JON W. DUDAS
*Director of the United States Patent and Trademark Office*

SEQUENCE LISTING

```
<160> NUMBER OF SEQ ID NOS: 184

<210> SEQ ID NO 1
<211> LENGTH: 1950
<212> TYPE: DNA
<213> ORGANISM: Artificial Sequence
<220> FEATURE:
<223> OTHER INFORMATION: sequence encoding fusion peptide of SEQ ID NO:2

<400> SEQUENCE: 1

aattctccat tttcttctgc tatcaaaata acagactcgt gattttccaa acgagctttc      60
aaaaaagcct ctgccccttg caaatcggat gcctgtctat aaaattcccg atattggtta     120
aacagcggcg caatggcggc cgcatctgat gtctttgctt ggcgaatgtt catcttattt     180
cttcctccct ctcaataatt ttttcattct atccctttttc tgtaaagttt atttttcaga    240
atacttttat catcatgctt tgaaaaaata tcacgataat atccattgtt ctcacggaag     300
cacacgcagg tcatttgaac gaatttttttc gacaggaatt tgccgggact caggagcatt    360
taacctaaaa aagcatgaca tttcagcata atgaacattt actcatgtct attttcgttc     420
ttttctgtat gaaaatagtt atttcgagtc tctacggaaa tagcgagaga tgatatacct     480
aaatagagat aaaatcatct caaaaaaatg ggtctactaa aatattattc catctattac     540
aataaattca cagaatagtc ttttaagtaa gtctactctg aattttttta aaaggagagg     600
gtaaagagtg agaagcaaaa aattgtggat cagcttgttg tttgcgttaa cgttaatctt     660
tacgatggcg ttcagcaaca tgtctgcgca ggctgatgat tattcagttg tagaggaaca     720
tgggcaacta agtattagta acggtgaatt agtcaatgaa cgaggcgaac aagttcagtt     780
aaaagggatg agttcccatg gtttgcaatg gtacggtcaa tttgtaaact atgaaagcat     840
gaaatggcta agagatgatt ggggaataac tgtattccga gcagcaatgt atacctcttc     900
aggaggatat attgacgatc catcagtaaa ggaaaaagta aaagagactg ttgaggctgc     960
gatagacctt ggcatatatg tgatcattga ttggcatatc ctttcagaca atgacccgaa    1020
tatatataaa gaagaagcga aggatttctt tgatgaaatg tcagagttgt atggagacta    1080
tccgaatgtg atatacgaaa ttgcaaatga accgaatggt agtgatgtta cgtgggacaa    1140
tcaaataaaa ccgtatgcag aagaagtgat tccggttatt cgtgacaatg accctaataa    1200
cattgttatt gtaggtacag gtacatggag tcaggatgtc catcatgcag ccgataatca    1260
gcttgcagat cctaacgtca tgtatgcatt tcatttttat gcaggaacac atggacaaaa    1320
tttacgagac caagtagatt atgcattaga tcaaggagca gcgatatttg ttagtgaatg    1380
ggggacaagt gcagctacag gtgatggtgg tgtgttttta gatgaagcac aagtgtggat    1440
tgactttatg gatgaaagaa atttaagctg ggccaactgg tctctaacgc ataaggatga    1500
gtcatctgca gcgttaatgc caggtgcaaa tccaactggt ggttggacag aggctgaact    1560
atctccatct ggtacatttg tgagggaaaa aataagagaa tcagcatcta ttccgccaag    1620
cgatccaaca ccgccatctg atccaggaga accggatcca gacgatgaga gctctaaacc    1680
ctgttgcgat caatgcgcat gtacgaaatc aaatcctcca cagtgtcggt gttccgatat    1740
gcgtctgaat agctgtcata gtgcatgcaa aagctgtatc tgcgccctga gttatccagc    1800
tcaatgtttt tgcgtcgaca tcacggactt ctgctatgag ccatgtaaac caagcgagga    1860
cgataaagag aaccatcatc accatcacca ttaaaagtta acagaggacg gatttcctga    1920
aggaaatccg ttttttattt tttaagcttg                                     1950


<210> SEQ ID NO 2
<211> LENGTH: 428
<212> TYPE: PRT
<213> ORGANISM: Artificial Sequence
<220> FEATURE:
<223> OTHER INFORMATION: synthetic fusion peptide

<400> SEQUENCE: 2

Met Arg Ser Lys Lys Leu Trp Ile Ser Leu Leu Phe Ala Leu Thr Leu
1               5                   10                  15
Ile Phe Thr Met Ala Phe Ser Asn Met Ser Ala Gln Ala Asp Asp Tyr
            20                  25                  30
Ser Val Val Glu Glu His Gly Gln Leu Ser Ile Ser Asn Gly Glu Leu
```

-continued

```
        35                  40                  45
    Val Asn Glu Arg Gly Glu Gln Val Gln Leu Lys Gly Met Ser Ser His
        50                  55                  60
    Gly Leu Gln Trp Tyr Gly Gln Phe Val Asn Tyr Glu Ser Met Lys Trp
    65                  70                  75                  80
    Leu Arg Asp Asp Trp Gly Ile Thr Val Phe Arg Ala Ala Met Tyr Thr
                    85                  90                  95
    Ser Ser Gly Gly Tyr Ile Asp Asp Pro Ser Val Lys Glu Lys Val Lys
                100                 105                 110
    Glu Thr Val Glu Ala Ala Ile Asp Leu Gly Ile Tyr Val Ile Ile Asp
            115                 120                 125
    Trp His Ile Leu Ser Asp Asn Asp Pro Asn Ile Tyr Lys Glu Glu Ala
        130                 135                 140
    Lys Asp Phe Phe Asp Glu Met Ser Glu Leu Tyr Gly Asp Tyr Pro Asn
    145                 150                 155                 160
    Val Ile Tyr Glu Ile Ala Asn Glu Pro Asn Gly Ser Asp Val Thr Trp
                    165                 170                 175
    Asp Asn Gln Ile Lys Pro Tyr Ala Glu Glu Val Ile Pro Val Ile Arg
                180                 185                 190
    Asp Asn Asp Pro Asn Asn Ile Val Ile Val Gly Thr Gly Thr Trp Ser
            195                 200                 205
    Gln Asp Val His His Ala Ala Asp Asn Gln Leu Ala Asp Pro Asn Val
        210                 215                 220
    Met Tyr Ala Phe His Phe Tyr Ala Gly Thr His Gly Gln Asn Leu Arg
    225                 230                 235                 240
    Asp Gln Val Asp Tyr Ala Leu Asp Gln Gly Ala Ala Ile Phe Val Ser
                    245                 250                 255
    Glu Trp Gly Thr Ser Ala Ala Thr Gly Asp Gly Gly Val Phe Leu Asp
                260                 265                 270
    Glu Ala Gln Val Trp Ile Asp Phe Met Asp Glu Arg Asn Leu Ser Trp
            275                 280                 285
    Ala Asn Trp Ser Leu Thr His Lys Asp Glu Ser Ser Ala Ala Leu Met
        290                 295                 300
    Pro Gly Ala Asn Pro Thr Gly Gly Trp Thr Glu Ala Glu Leu Ser Pro
    305                 310                 315                 320
    Ser Gly Thr Phe Val Arg Glu Lys Ile Arg Glu Ser Ala Ser Ile Pro
                    325                 330                 335
    Pro Ser Asp Pro Thr Pro Pro Ser Asp Pro Gly Glu Pro Asp Pro Asp
                340                 345                 350
    Asp Glu Ser Ser Lys Pro Cys Cys Asp Gln Cys Ala Cys Thr Lys Ser
            355                 360                 365
    Asn Pro Pro Gln Cys Arg Cys Ser Asp Met Arg Leu Asn Ser Cys His
        370                 375                 380
    Ser Ala Cys Lys Ser Cys Ile Cys Ala Leu Ser Tyr Pro Ala Gln Cys
    385                 390                 395                 400
    Phe Cys Val Asp Ile Thr Asp Phe Cys Tyr Glu Pro Cys Lys Pro Ser
                    405                 410                 415
    Glu Asp Asp Lys Glu Asn His His His His His His
                420                 425
```

<210> SEQ ID NO 3
<211> LENGTH: 223
<212> TYPE: DNA
<213> ORGANISM: Artificial Sequence
<220> FEATURE:
<223> OTHER INFORMATION: sequence encoding fusion peptide of SEQ ID NO:4

<400> SEQUENCE: 3

```
ggatccagac gatgagagct ctaaaccctg ttgcgatcaa tgcgcatgtt ataatttgta      60
tgggtggact tgtcgctgca gcgatatgcg tctgaattcc tgtcatagtg cctgcaaaag     120
ctgcgcatgt tataacctgt acgggtggac ctgtttttgc gtcgacatca cggacttctg     180
ctatgagcca tgtaaaccaa gcgaggacga taaagagaac taa                       223
```

<210> SEQ ID NO 4
<211> LENGTH: 73
<212> TYPE: PRT
<213> ORGANISM: Artificial Sequence
<220> FEATURE:
<223> OTHER INFORMATION: synthetic fusion peptide

<400> SEQUENCE: 4

```
Asp Pro Asp Asp Glu Ser Ser Lys Pro Cys Cys Asp Gln Cys Ala Cys
 1               5                  10                  15
Tyr Asn Leu Tyr Gly Trp Thr Cys Arg Cys Ser Asp Met Arg Leu Asn
            20                  25                  30
```

-continued

```
Ser Cys His Ser Ala Cys Lys Ser Cys Ala Cys Tyr Asn Leu Tyr Gly
        35                  40                  45
Trp Thr Cys Phe Cys Val Asp Ile Thr Asp Phe Cys Tyr Glu Pro Cys
    50                  55                  60
Lys Pro Ser Glu Asp Asp Lys Glu Asn
65                  70
```

<210> SEQ ID NO 5
<211> LENGTH: 1512
<212> TYPE: DNA
<213> ORGANISM: Artificial Sequence
<220> FEATURE:
<223> OTHER INFORMATION: sequence encoding fusion peptide of SEQ ID NO:6

<400> SEQUENCE: 5

```
agcgcgcagg ctagcgatgt tgtacaactg aaaaaagaca ctttcgacga cttcatcaaa      60
acaaatgacc ttgttcttgc tgaatttttc gcgccgtggt gcggtcactg caaagctctt     120
gctcctgagt acgaggaagc tgcaactaca ctgaaagaaa agaacatcaa acttgctaaa     180
gtagactgca cagaagagac tgatctttgc caacaacatg gtgttgaggg ctacccaact     240
cttaaagttt tccgtggcct tgacaacgta tctccttaca aaggtcaacg taaagctgct     300
gcaatcactt catacatgat caaacaatct ctgcctgctg tatctgaagt tacaaaagac     360
aaccttgaag aatttaaaaa agctgacaaa gctgttcttg ttgcttatgt agatgcttct     420
gacaaagcat ctagcgaagt tttcactcaa gttgctgaaa aactgcgcga taactaccca     480
ttcggctcta gctctgatgc tgcactggct gaagctgagg gcgttaaagc acctgctatt     540
gttctttaca aagactttga tgaaggtaaa gcggttttct ctgaaaaatt cgaagtagag     600
gcaatcgaaa aattcgctaa aacaggtgct actccactta ttggcgaaat cggacctgaa     660
acttactctg attacatgtc agctggcatc cctctggcat acattttcgc tgaaacagct     720
gaagagcgta aagaactcag cgacaaactt aaaccaatcg ctgaagctca acgtggcgtt     780
attaactttg gtactattga cgctaaagca tttggtgctc acgctggaaa cctgaatctg     840
aaaactgaca aattccctgc tttcgcaatc caagaagttg ctaaaaacca aaaattccct     900
tttgatcaag aaaaagaaat tacttttgaa gcgatcaaag cattcgttga cgatttttgtt     960
gctggtaaaa tcgaaccaag catcaaatca gaaccaatcc ctgaaaaaca agaaggtcct    1020
gttactgtag ttgtagctaa aaactacaat gaaatcgttc tggacgatac taaagatgta    1080
ttaattgaat tttacgctcc ttggtgcggt cactgcaaag ctcttgctcc taaatacgaa    1140
gaacttggtg ctctgtatgc aaaaagcgag ttcaaagacc gtgttgtaat tgctaaagtt    1200
gatgcaacag ctaacgatgt tccagatgaa attcaaggat tccctactat caaactatac    1260
ccagctggtg caaaaggtca acctgttact tactctggtt cacgcactgt tgaagacctt    1320
atcaaattca ttgctgaaaa cggtaaatac aaagctgcaa tctcagaaga tgctgaagag    1380
actagttcag caactgaaac aactacagaa actgctacaa agtcagaaga agctgcaaaa    1440
gaaactgcaa cagaacacga cgaacttgga tctggttccg gagatgacga tgacaaagac    1500
gatgagagct ct                                                        1512
```

<210> SEQ ID NO 6
<211> LENGTH: 504
<212> TYPE: PRT
<213> ORGANISM: Artificial Sequence
<220> FEATURE:
<223> OTHER INFORMATION: synthetic fusion peptide

<400> SEQUENCE: 6

```
Ser Ala Gln Ala Ser Asp Val Val Gln Leu Lys Lys Asp Thr Phe Asp
 1               5                  10                  15
Asp Phe Ile Lys Thr Asn Asp Leu Val Leu Ala Glu Phe Phe Ala Pro
            20                  25                  30
Trp Cys Gly His Cys Lys Ala Leu Ala Pro Glu Tyr Glu Glu Ala Ala
        35                  40                  45
Thr Thr Leu Lys Glu Lys Asn Ile Lys Leu Ala Lys Val Asp Cys Thr
    50                  55                  60
Glu Glu Thr Asp Leu Cys Gln Gln His Gly Val Glu Gly Tyr Pro Thr
65                  70                  75                  80
Leu Lys Val Phe Arg Gly Leu Asp Asn Val Ser Pro Tyr Lys Gly Gln
                85                  90                  95
Arg Lys Ala Ala Ala Ile Thr Ser Tyr Met Ile Lys Gln Ser Leu Pro
            100                 105                 110
Ala Val Ser Glu Val Thr Lys Asp Asn Leu Glu Glu Phe Lys Lys Ala
        115                 120                 125
Asp Lys Ala Val Leu Val Ala Tyr Val Asp Ala Ser Asp Lys Ala Ser
    130                 135                 140
Ser Glu Val Phe Thr Gln Val Ala Glu Lys Leu Arg Asp Asn Tyr Pro
145                 150                 155                 160
Phe Gly Ser Ser Ser Asp Ala Ala Leu Ala Glu Ala Glu Gly Val Lys
                165                 170                 175
Ala Pro Ala Ile Val Leu Tyr Lys Asp Phe Asp Glu Gly Lys Ala Val
            180                 185                 190
Phe Ser Glu Lys Phe Glu Val Glu Ala Ile Glu Lys Phe Ala Lys Thr
```

-continued

```
        195                 200                 205
Gly Ala Thr Pro Leu Ile Gly Glu Ile Gly Pro Glu Thr Tyr Ser Asp
    210                 215                 220
Tyr Met Ser Ala Gly Ile Pro Leu Ala Tyr Ile Phe Ala Glu Thr Ala
225                 230                 235                 240
Glu Glu Arg Lys Glu Leu Ser Asp Lys Leu Lys Pro Ile Ala Glu Ala
                245                 250                 255
Gln Arg Gly Val Ile Asn Phe Gly Thr Ile Asp Ala Lys Ala Phe Gly
            260                 265                 270
Ala His Ala Gly Asn Leu Asn Leu Lys Thr Asp Lys Phe Pro Ala Phe
        275                 280                 285
Ala Ile Gln Glu Val Ala Lys Asn Gln Lys Phe Pro Phe Asp Gln Glu
    290                 295                 300
Lys Glu Ile Thr Phe Glu Ala Ile Lys Ala Phe Val Asp Asp Phe Val
305                 310                 315                 320
Ala Gly Lys Ile Glu Pro Ser Ile Lys Ser Glu Pro Ile Pro Glu Lys
                325                 330                 335
Gln Glu Gly Pro Val Thr Val Val Val Ala Lys Asn Tyr Asn Glu Ile
            340                 345                 350
Val Leu Asp Asp Thr Lys Asp Val Leu Ile Glu Phe Tyr Ala Pro Trp
        355                 360                 365
Cys Gly His Cys Lys Ala Leu Ala Pro Lys Tyr Glu Glu Leu Gly Ala
    370                 375                 380
Leu Tyr Ala Lys Ser Glu Phe Lys Asp Arg Val Val Ile Ala Lys Val
385                 390                 395                 400
Asp Ala Thr Ala Asn Asp Val Pro Asp Glu Ile Gln Gly Phe Pro Thr
                405                 410                 415
Ile Lys Leu Tyr Pro Ala Gly Ala Lys Gly Gln Pro Val Thr Tyr Ser
            420                 425                 430
Gly Ser Arg Thr Val Glu Asp Leu Ile Lys Phe Ile Ala Glu Asn Gly
        435                 440                 445
Lys Tyr Lys Ala Ala Ile Ser Glu Asp Ala Glu Glu Thr Ser Ser Ala
    450                 455                 460
Thr Glu Thr Thr Thr Glu Thr Ala Thr Lys Ser Glu Glu Ala Ala Lys
465                 470                 475                 480
Glu Thr Ala Thr Glu His Asp Glu Leu Gly Ser Gly Ser Gly Asp Asp
                485                 490                 495
Asp Asp Lys Asp Asp Glu Ser Ser
            500
```

<210> SEQ ID NO 7
<211> LENGTH: 1495
<212> TYPE: DNA
<213> ORGANISM: Artificial Sequence
<220> FEATURE:
<223> OTHER INFORMATION: sequence encoding fusion peptide of SEQ ID NO:8

<400> SEQUENCE: 7

```
gaattctcca ttttcttctg ctatcaaaat aacagactcg tgattttcca aacgagcttt      60
caaaaaagcc tctgcccctt gcaaatcgga tgcctgtcta taaaattccc gatattggtt     120
aaacagcggc gcaatggcgg ccgcatctga tgtctttgct tggcgaatgt tcatcttatt     180
tcttcctccc tctcaataat tttttcattc tatccctttt ctgtaaagtt tatttttcag     240
aatactttta tcatcatgct ttgaaaaaat atcacgataa tatccattgt tctcacggaa     300
gcacacgcag gtcatttgaa cgaatttttt cgacaggaat ttgccgggac tcaggagcat     360
ttaacctaaa aaagcatgac atttcagcat aatgaacatt tactcatgtc tattttcgtt     420
cttttctgta tgaaaatagt tatttcgagt ctctacggaa atagcgagag atgatatacc     480
taaatagaga taaaatcatc tcaaaaaaat gggtctacta aaatattatt ccatctatta     540
caataaattc acagaatagt cttttaagta agtctactct gaattttttt aaaaggagag     600
ggtaaagagt gagaagcaaa aaattgtgga tcagcttgtt gtttgcgtta acgctggcgg     660
cctcttgcct gtccgtctgt gccactgtcg cggcggctcc cctgccggat acaccgggag     720
cgccatttcc ggctgtcgcc aatttcgacc gcagtggccc ctacaccacc agcagccaga     780
gcgaggggcc gagctgtcgc atctatcggc cccgcgacct gggtcagggg ggcgtgcgtc     840
atccggtgat tctctggggc aatggcaccg gtgccgggcc gtccacctat gccggcttgc     900
tatcgcactg ggcaagccac ggtttcgtgg tggcggcggc ggaaacctcc aatgccggta     960
ccgggcggga aatgctcgcc tgcctggact atctggtacg tgagaacgac acccccctacg   1020
gcacctattc cggcaagctc aataccgggc gagtcggcac ttctgggcat tcccagggtg    1080
gtggcggctc gatcatggcc gggcaggata cgagggtgcg taccacggcg ccgatccagc    1140
cctacaccct cggcctgggg cacgacagcg cctcgcagcg gcggcagcag gggccgatgt    1200
tcctgatgtc cggtggcggt gacaccatcg cctttcccta cctcaacgct cagccggtct    1260
accggcgtgc caatgtgccg gtgttctggg gcgaacggcg ttacgtcagc cacttcgagc    1320
cggtcggtag cggtggggcc tatcgcggcc cgagcacggc atggttccgc ttccagctga    1380
tggatgacca agacgcccgc gctaccttct acggcgcgca gtgcagtctg tgcacttctc    1440
tgctttggtc tgttgaacgc agaggtcttg acaacaatga tcctattccg gatcc          1495
```

<210> SEQ ID NO 8
<211> LENGTH: 295

-continued

```
<212> TYPE: PRT
<213> ORGANISM: Artificial Sequence
<220> FEATURE:
<223> OTHER INFORMATION: synthetic fusion peptide

<400> SEQUENCE: 8

Val Arg Ser Lys Lys Leu Trp Ile Ser Leu Leu Phe Ala Leu Thr Leu
 1               5                   10                  15
Ala Ala Ser Cys Leu Ser Val Cys Ala Thr Val Ala Ala Ala Pro Leu
            20                  25                  30
Pro Asp Thr Pro Gly Ala Pro Phe Pro Ala Val Ala Asn Phe Asp Arg
        35                  40                  45
Ser Gly Pro Tyr Thr Thr Ser Ser Gln Ser Glu Gly Pro Ser Cys Arg
    50                  55                  60
Ile Tyr Arg Pro Arg Asp Leu Gly Gln Gly Gly Val Arg His Pro Val
65                  70                  75                  80
Ile Leu Trp Gly Asn Gly Thr Gly Ala Gly Pro Ser Thr Tyr Ala Gly
                85                  90                  95
Leu Leu Ser His Trp Ala Ser His Gly Phe Val Val Ala Ala Ala Glu
            100                 105                 110
Thr Ser Asn Ala Gly Thr Gly Arg Glu Met Leu Ala Cys Leu Asp Tyr
        115                 120                 125
Leu Val Arg Glu Asn Asp Thr Pro Tyr Gly Thr Tyr Ser Gly Lys Leu
    130                 135                 140
Asn Thr Gly Arg Val Gly Thr Ser Gly His Ser Gln Gly Gly Gly Gly
145                 150                 155                 160
Ser Ile Met Ala Gly Gln Asp Thr Arg Val Arg Thr Thr Ala Pro Ile
                165                 170                 175
Gln Pro Tyr Thr Leu Gly Leu Gly His Asp Ser Ala Ser Gln Arg Arg
            180                 185                 190
Gln Gln Gly Pro Met Phe Leu Met Ser Gly Gly Gly Asp Thr Ile Ala
        195                 200                 205
Phe Pro Tyr Leu Asn Ala Gln Pro Val Tyr Arg Arg Ala Asn Val Pro
    210                 215                 220
Val Phe Trp Gly Glu Arg Arg Tyr Val Ser His Phe Glu Pro Val Gly
225                 230                 235                 240
Ser Gly Gly Ala Tyr Arg Gly Pro Ser Thr Ala Trp Phe Arg Phe Gln
                245                 250                 255
Leu Met Asp Asp Gln Asp Ala Arg Ala Thr Phe Tyr Gly Ala Gln Cys
            260                 265                 270
Ser Leu Cys Thr Ser Leu Leu Trp Ser Val Glu Arg Arg Gly Leu Asp
        275                 280                 285
Asn Asn Asp Pro Ile Pro Asp
    290                 295


<210> SEQ ID NO 9
<211> LENGTH: 10
<212> TYPE: PRT
<213> ORGANISM: Artificial Sequence
<220> FEATURE:
<223> OTHER INFORMATION: synthetic

<400> SEQUENCE: 9

Ala Cys Tyr Asn Leu Tyr Gly Trp Thr Cys
 1               5                   10


<210> SEQ ID NO 10
<211> LENGTH: 288
<212> TYPE: DNA
<213> ORGANISM: Artificial Sequence
<220> FEATURE:
<223> OTHER INFORMATION: synthetic

<400> SEQUENCE: 10

aacctgcgtc tgtctaagct tggcctgctt atgaaatcag accatcagca cagcaatgac      60
gatgagagct ctaaaccctg ttgcgatcaa tgcgcatgta cgaaatcaaa tcctccacag     120
tgtcggtgtt ccgatatgcg tctgaatagc tgtcatagtg catgcaaaag ctgtatctgc     180
gccctgagtt atccagctca atgtttttgc gtcgacatca cggacttctg ctatgagcca     240
tgtaaaccaa gcgaggacga taaagagaac catcatcacc atcaccat                  288


<210> SEQ ID NO 11
<211> LENGTH: 96
<212> TYPE: PRT
```

-continued

```
<213> ORGANISM: Artificial Sequence
<220> FEATURE:
<223> OTHER INFORMATION: synthetic

<400> SEQUENCE: 11

      Asn Leu Arg Leu Ser Lys Leu Gly Leu Leu Met Lys Ser Asp His Gln
       1               5                  10                  15
      His Ser Asn Asp Asp Glu Ser Ser Lys Pro Cys Cys Asp Gln Cys Ala
                  20                  25                  30
      Cys Thr Lys Ser Asn Pro Pro Gln Cys Arg Cys Ser Asp Met Arg Leu
              35                  40                  45
      Asn Ser Cys His Ser Ala Cys Lys Ser Cys Ile Cys Ala Leu Ser Tyr
          50                  55                  60
      Pro Ala Gln Cys Phe Cys Val Asp Ile Thr Asp Phe Cys Tyr Glu Pro
      65                  70                  75                  80
      Cys Lys Pro Ser Glu Asp Asp Lys Glu Asn His His His His His His
                      85                  90                  95


<210> SEQ ID NO 12
<211> LENGTH: 213
<212> TYPE: DNA
<213> ORGANISM: Artificial Sequence
<220> FEATURE:
<223> OTHER INFORMATION: synthetic

<400> SEQUENCE: 12

      gacgatgaga gctctaaacc ctgttgcgat caatgcgcat gtacgaaatc aaatcctcca      60
      cagtgtcggt gttccgatat gcgtctgaat agctgtcata gtgcatgcaa aagctgtatc     120
      tgcgccctga gttatccagc tcaatgtttt tgcgtcgaca tcacggactt ctgctatgag     180
      ccatgtaaac caagcgagga cgataaagag aac                                  213


<210> SEQ ID NO 13
<211> LENGTH: 71
<212> TYPE: PRT
<213> ORGANISM: Artificial Sequence
<220> FEATURE:
<223> OTHER INFORMATION: synthetic

<400> SEQUENCE: 13

      Asp Asp Glu Ser Ser Lys Pro Cys Cys Asp Gln Cys Ala Cys Thr Lys
       1               5                  10                  15
      Ser Asn Pro Pro Gln Cys Arg Cys Ser Asp Met Arg Leu Asn Ser Cys
                  20                  25                  30
      His Ser Ala Cys Lys Ser Cys Ile Cys Ala Leu Ser Tyr Pro Ala Gln
              35                  40                  45
      Cys Phe Cys Val Asp Ile Thr Asp Phe Cys Tyr Glu Pro Cys Lys Pro
          50                  55                  60
      Ser Glu Asp Asp Lys Glu Asn
      65                  70


<210> SEQ ID NO 14
<211> LENGTH: 34
<212> TYPE: DNA
<213> ORGANISM: Artificial Sequence
<220> FEATURE:
<223> OTHER INFORMATION: primer

<400> SEQUENCE: 14

      cagcacggat ccagacgatg agagctctaa accc                                  34


<210> SEQ ID NO 15
<211> LENGTH: 84
<212> TYPE: DNA
<213> ORGANISM: Artificial Sequence
<220> FEATURE:
<223> OTHER INFORMATION: primer

<400> SEQUENCE: 15

      ctgcagaagc ttaaaaataa aaaaacggat ttccttcagg aaatccgtcc tctgttaact      60
      tttagttctc tttatcgtcc tcgc                                             84
```

-continued

<210> SEQ ID NO 16
<211> LENGTH: 88
<212> TYPE: DNA
<213> ORGANISM: Artificial Sequence
<220> FEATURE:
<223> OTHER INFORMATION: primer

<400> SEQUENCE: 16
ctgcagaagc ttaaaaataa aaaaacggat ttccttcagg aaatccgtcc tctgttaact 60
tttaatggtg atggtgatga tggttctc 88

<210> SEQ ID NO 17
<211> LENGTH: 31
<212> TYPE: DNA
<213> ORGANISM: Artificial Sequence
<220> FEATURE:
<223> OTHER INFORMATION: primer

<400> SEQUENCE: 17
gatatgcgtc tgaattcctg tcatagtgca t 31

<210> SEQ ID NO 18
<211> LENGTH: 31
<212> TYPE: DNA
<213> ORGANISM: Artificial Sequence
<220> FEATURE:
<223> OTHER INFORMATION: primer

<400> SEQUENCE: 18
atgcactatg acaggaattc agacgcatat c 31

<210> SEQ ID NO 19
<211> LENGTH: 74
<212> TYPE: DNA
<213> ORGANISM: Artificial Sequence
<220> FEATURE:
<223> OTHER INFORMATION: synthetic oligonucleotide

<400> SEQUENCE: 19
ctaaaccctg ttgcgatcaa tgcgcatgtt ataatttgta tgggtggact tgtcgctgca 60
gcgatatgcg tctg 74

<210> SEQ ID NO 20
<211> LENGTH: 82
<212> TYPE: DNA
<213> ORGANISM: Artificial Sequence
<220> FEATURE:
<223> OTHER INFORMATION: synthetic oligonucleotide

<400> SEQUENCE: 20
aattcagacg catatcgctg cagcgacaag tccacccata caaattataa catgcgcatt 60
gatcgcaaca gggtttagag ct 82

<210> SEQ ID NO 21
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 21
aattcctgtc atagtgcctg caaaagctgc gcatgttata acctgtacgg gtggacctgt 60
ttttgcg 67

<210> SEQ ID NO 22

-continued

<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 22
tcgacgcaaa aacaggtcca cccgtacagg ttataacatg cgcagctttt gcaggcacta 60
tgacagg 67

<210> SEQ ID NO 23
<211> LENGTH: 80
<212> TYPE: DNA
<213> ORGANISM: Artificial Sequence
<220> FEATURE:
<223> OTHER INFORMATION: synthetic

<400> SEQUENCE: 23
ctaaaccctg ttgcgatcaa tgcgcatgtg ttgttcagga ctggggtcac caccgttgtc 60
gctgcagcga tatgcgtctg 80

<210> SEQ ID NO 24
<211> LENGTH: 88
<212> TYPE: DNA
<213> ORGANISM: Artificial Sequence
<220> FEATURE:
<223> OTHER INFORMATION: synthetic

<400> SEQUENCE: 24
aattcagacg catatcgctg cagcgacaac ggtggtgacc ccagtcctga acaacacatg 60
cgcattgatc gcaacagggt ttagagct 88

<210> SEQ ID NO 25
<211> LENGTH: 53
<212> TYPE: DNA
<213> ORGANISM: Artificial Sequence
<220> FEATURE:
<223> OTHER INFORMATION: synthetic

<400> SEQUENCE: 25
caaaagctgt atctgcgttg ttcaggactg gggtcaccac cgttgttttt gcg 53

<210> SEQ ID NO 26
<211> LENGTH: 61
<212> TYPE: DNA
<213> ORGANISM: Artificial Sequence
<220> FEATURE:
<223> OTHER INFORMATION: synthetic

<400> SEQUENCE: 26
tcgacgcaaa aacaacggtg gtgaccccag tcctgaacaa cgcagataca gcttttgcat 60
g 61

<210> SEQ ID NO 27
<211> LENGTH: 74
<212> TYPE: DNA
<213> ORGANISM: Artificial Sequence
<220> FEATURE:
<223> OTHER INFORMATION: synthetic

<400> SEQUENCE: 27
ctaaaccctg ttgcgatcaa tgcagctgtg gtcgtaaaat cccgatccag tgtcgctgca 60
gcgatatgcg tctg 74

<210> SEQ ID NO 28
<211> LENGTH: 82
<212> TYPE: DNA

-continued

<213> ORGANISM: Artificial Sequence
<220> FEATURE:
<223> OTHER INFORMATION: synthetic

<400> SEQUENCE: 28
aattcagacg catatcgctg cagcgacact ggatcgggat tttacgacca cagctgcatt 60
gatcgcaaca gggtttagag ct 82

<210> SEQ ID NO 29
<211> LENGTH: 74
<212> TYPE: DNA
<213> ORGANISM: Artificial Sequence
<220> FEATURE:
<223> OTHER INFORMATION: synthetic

<400> SEQUENCE: 29
ctaaaccctg ttgcgatcaa tgcggttgtg ctcgttctaa cctggacgaa tgtcgctgca 60
gcgatatgcg tctg 74

<210> SEQ ID NO 30
<211> LENGTH: 82
<212> TYPE: DNA
<213> ORGANISM: Artificial Sequence
<220> FEATURE:
<223> OTHER INFORMATION: synthetic

<400> SEQUENCE: 30
aattcagacg catatcgctg cagcgacatt cgtccaggtt agaacgagca caaccgcatt 60
gatcgcaaca gggtttagag ct 82

<210> SEQ ID NO 31
<211> LENGTH: 74
<212> TYPE: DNA
<213> ORGANISM: Artificial Sequence
<220> FEATURE:
<223> OTHER INFORMATION: synthetic

<400> SEQUENCE: 31
ctaaaccctg ttgcgatcaa tgcggttgtc agcgtgctct gccgatcctg tgtcgctgca 60
gcgatatgcg tctg 74

<210> SEQ ID NO 32
<211> LENGTH: 82
<212> TYPE: DNA
<213> ORGANISM: Artificial Sequence
<220> FEATURE:
<223> OTHER INFORMATION: synthetic

<400> SEQUENCE: 32
aattcagacg catatcgctg cagcgacaca ggatcggcag agcacgctga caaccgcatt 60
gatcgcaaca gggtttagag ct 82

<210> SEQ ID NO 33
<211> LENGTH: 74
<212> TYPE: DNA
<213> ORGANISM: Artificial Sequence
<220> FEATURE:
<223> OTHER INFORMATION: synthetic

<400> SEQUENCE: 33
ctaaaccctg ttgcgatcaa tgccagtgtg gtcgtctgca catgaaaacc tgtcgctgca 60
gcgatatgcg tctg 74

<210> SEQ ID NO 34
<211> LENGTH: 82
<212> TYPE: DNA
<213> ORGANISM: Artificial Sequence -continued
<220> FEATURE:
<223> OTHER INFORMATION: synthetic

<400> SEQUENCE: 34
aattcagacg catatcgctg cagcgacagg ttttcatgtg cagacgacca cactggcatt 60
gatcgcaaca gggtttagag ct 82

<210> SEQ ID NO 35
<211> LENGTH: 67
<212> TYPE: DNA
<213> ORGANISM: Artificial Sequence
<220> FEATURE:
<223> OTHER INFORMATION: synthetic

<400> SEQUENCE: 35
aattcctgtc atagtgcctg caaaagctgt atctgcgccc gtagtttgcc agctcaatgt 60
ttttgcg 67

<210> SEQ ID NO 36
<211> LENGTH: 67
<212> TYPE: DNA
<213> ORGANISM: Artificial Sequence
<220> FEATURE:
<223> OTHER INFORMATION: synthetic

<400> SEQUENCE: 36
tcgacgcaaa aacattgagc tggcaaacta cgggcgcaga tacagctttt gcaggcacta 60
tgacagg 67

<210> SEQ ID NO 37
<211> LENGTH: 74
<212> TYPE: DNA
<213> ORGANISM: Artificial Sequence
<220> FEATURE:
<223> OTHER INFORMATION: synthetic

<400> SEQUENCE: 37
ctaaaccctg ttgcgatcaa tgcaactgta cgtactcaac cctccacag tgtcgctgca 60
gcgatatgcg tctg 74

<210> SEQ ID NO 38
<211> LENGTH: 82
<212> TYPE: DNA
<213> ORGANISM: Artificial Sequence
<220> FEATURE:
<223> OTHER INFORMATION: synthetic

<400> SEQUENCE: 38
aattcagacg catatcgctg cagcgacact gtggaggggt tgagtacgta cagttgcatt 60
gatcgcaaca gggtttagag ct 82

<210> SEQ ID NO 39
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 39
ctgtatctgc aaacgctcaa aatctcgtgg ctgtttttgc gtcgacatca c 51

<210> SEQ ID NO 40
<211> LENGTH: 51
<212> TYPE: DNA
<213> ORGANISM: Artificial Sequence
<220> FEATURE:
<223> OTHER INFORMATION: synthetic oligonucleotide -continued

<400> SEQUENCE: 40
cgcaaaaaca gccacgagat tttgagcgtt tgcagataca gcttttgcat g 51

<210> SEQ ID NO 41
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 41
ctgtatctgc tggtataatc aaatgacaac atgtttttgc gtcgacatca c 51

<210> SEQ ID NO 42
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 42
cgcaaaaaca tgttgtcatt tgattatacc agcagataca gcttttgcat g 51

<210> SEQ ID NO 43
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 43
ctgtatctgc catcaacttg gcccgaattc atgtttttgc gtcgacatca c 51

<210> SEQ ID NO 44
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 44
cgcaaaaaca tgaattcggg ccaagttgat ggcagataca gcttttgcat g 51

<210> SEQ ID NO 45
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 45
ctgtatctgc catccgtggg caccgtattc ttgtttttgc gtcgacatca c 51

<210> SEQ ID NO 46
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 46
cgcaaaaaca agaatacggt gcccacggat ggcagataca gcttttgcat g 51

<210> SEQ ID NO 47

-continued

<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 47
ctgtatctgc aatcttcatt atcttcaaca gtgtttttgc gtcgacatca c 51

<210> SEQ ID NO 48
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 48
cgcaaaaaca ctgttgaaga taatgaagat tgcagataca gcttttgcat g 51

<210> SEQ ID NO 49
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 49
ctgtatctgc acaccgtctc tttatcgccc gtgtttttgc gtcgacatca c 51

<210> SEQ ID NO 50
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 50
cgcaaaaaca cgggcgataa agagacggtg tgcagataca gcttttgcat g 51

<210> SEQ ID NO 51
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 51
ctgtatctgc cttacagatc aatctaaacc gtgtttttgc gtcgacatca c 51

<210> SEQ ID NO 52
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 52
cgcaaaaaca cggtttagat tgatctgtaa ggcagataca gcttttgcat g 51

<210> SEQ ID NO 53
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 53

-continued ctgtatctgc gttacaacat caatgggcat gtgtttttgc gtcgacatca c 51

<210> SEQ ID NO 54
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 54
cgcaaaaaca catgcccatt gatgttgtaa cgcagataca gcttttgcat g 51

<210> SEQ ID NO 55
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 55
ctgtatctgc cgcgcatcac cgtatgattg gtgtttttgc gtcgacatca c 51

<210> SEQ ID NO 56
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 56
cgcaaaaaca ccaatcatac ggtgatgcgc ggcagataca gcttttgcat g 51

<210> SEQ ID NO 57
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 57
ctgtatctgc tcaacacaaa aaattccgca atgtttttgc gtcgacatca c 51

<210> SEQ ID NO 58
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 58
cgcaaaaaca ttgcggaatt ttttgtgttg agcagataca gcttttgcat g 51

<210> SEQ ID NO 59
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 59
ctgtatctgc acacaatttc gctctgcaac atgtttttgc gtcgacatca c 51

<210> SEQ ID NO 60
<211> LENGTH: 51
<212> TYPE: DNA

-continued

<213> ORGANISM: Artificial Sequence
<220> FEATURE:
<223> OTHER INFORMATION: synthetic oligonucleotide

<400> SEQUENCE: 60
cgcaaaaaca tgttgcagag cgaaattgtg tgcagataca gcttttgcat g 51

<210> SEQ ID NO 61
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 61
ctgtatctgc ccggatcatg ttccgcatct ttgtttttgc gtcgacatca c 51

<210> SEQ ID NO 62
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 62
cgcaaaaaca aagatgcgga acatgatccg ggcagataca gcttttgcat g 51

<210> SEQ ID NO 63
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 63
ctgtatctgc tcaggctttc cgctttctac atgtttttgc gtcgacatca c 51

<210> SEQ ID NO 64
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 64
cgcaaaaaca tgtagaaagc ggaaagcctg agcagataca gcttttgcat g 51

<210> SEQ ID NO 65
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 65
tcaatgcgca tgtgaagaga tctggactat gctttgccgg tgttccgata tgcgtc 56

<210> SEQ ID NO 66
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 66
cggaacaccg gcaaagcata gtccagatct cttcacatgc gcattgatcg caacagg 57

-continued

<210> SEQ ID NO 67
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 67
caaaagctgt gcttgtgaag agatctggac tatgctttgc ttttgcgtcg acatcacgg 59

<210> SEQ ID NO 68
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 68
acgcaaaagc aaagcatagt ccagatctct tcacaagcac agcttttgca tgcactatg 59

<210> SEQ ID NO 69
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 69
tcaatgcgca tgttgggccc ttactgtcaa aacatgccgg tgttccgata tgcgtc 56

<210> SEQ ID NO 70
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 70
cggaacaccg gcatgttttg acagtaaggg cccaacatgc gcattgatcg caacagg 57

<210> SEQ ID NO 71
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 71
caaaagctgt gcttgttggg cccttactgt caaaacatgc ttttgcgtcg acatcacgg 59

<210> SEQ ID NO 72
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 72
acgcaaaagc atgttttgac agtaagggcc caacaagcac agcttttgca tgcactatg 59

<210> SEQ ID NO 73
<211> LENGTH: 56
<212> TYPE: DNA
<213> ORGANISM: Artificial Sequence
<220> FEATURE:

-continued

<223> OTHER INFORMATION: synthetic oligonucleotide

<400> SEQUENCE: 73
tcaatgcgca tgtcttacag tactgtggac tacatgccgg tgttccgata tgcgtc 56

<210> SEQ ID NO 74
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 74
cggaacaccg gcatgtagtc cacagtactg taagacatgc gcattgatcg caacagg 57

<210> SEQ ID NO 75
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 75
caaaagctgt gcttgtctta cagtactgtg gactacatgc ttttgcgtcg acatcacgg 59

<210> SEQ ID NO 76
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 76
acgcaaaagc atgtagtcca cagtactgta agacaagcac agcttttgca tgcactatg 59

<210> SEQ ID NO 77
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 77
tcaatgcgca tgtactcttt ggaacagatc tccttgccgg tgttccgata tgcgtc 56

<210> SEQ ID NO 78
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 78
cggaacaccg gcaaggagat ctgttccaaa gagtacatgc gcattgatcg caacagg 57

<210> SEQ ID NO 79
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 79
caaaagctgt gcttgtactc tttggaatcg atctccttgc ttttgcgtcg acatcacgg 59

-continued

<210> SEQ ID NO 80
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 80
acgcaaaagc aaggagatcg attccaaaga gtacaagcac agcttttgca tgcactatg 59

<210> SEQ ID NO 81
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 81
tcaatgcgca tgtacaaaca tcgattctac tccttgccgg tgttccgata tgcgtc 56

<210> SEQ ID NO 82
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 82
cggaacaccg gcaaggagta gaatcgatgt ttgtacatgc gcattgatcg caacagg 57

<210> SEQ ID NO 83
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 83
caaaagctgt gcttgcacaa acatcgattc tactccttgt ttttgcgtcg acatcacgg 59

<210> SEQ ID NO 84
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 84
acgcaaaaac aaggagtaga atcgatgttt gtgcaagcac agcttttgca tgcactatg 59

<210> SEQ ID NO 85
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 85
tcaatgcgca tgtacaaaaa tcgatcgtac tccttgccgg tgttccgata tgcgtc 56

<210> SEQ ID NO 86
<211> LENGTH: 57
<212> TYPE: DNA
<213> ORGANISM: Artificial Sequence
<220> FEATURE:
<223> OTHER INFORMATION: synthetic oligonucleotide -continued

<400> SEQUENCE: 86
cggaacaccg gcaaggagta cgatcgattt ttgtacatgc gcattgatcg caacagg 57

<210> SEQ ID NO 87
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 87
caaaagctgt gcttgcacaa aaatcgatcg tactccttgt ttttgcgtcg acatcacgg 59

<210> SEQ ID NO 88
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 88
acgcaaaaac aaggagtacg atcgattttt gtgcaagcac agcttttgca tgcactatg 59

<210> SEQ ID NO 89
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 89
tcaatgcgca tgtcacctgc agacaactga aacatgccgg tgttccgata tgcgtc 56

<210> SEQ ID NO 90
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 90
cggaacaccg gcatgtttca gttgtctgca ggtgacatgc gcattgatcg caacagg 57

<210> SEQ ID NO 91
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 91
caaaagctgt gcttgccacc tgcagacaac tgaaacatgt ttttgcgtcg acatcacgg 59

<210> SEQ ID NO 92
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 92
acgcaaaaac atgtttcagt tgtctgcagg tggcaagcac agcttttgca tgcactatg 59

<210> SEQ ID NO 93
<211> LENGTH: 56

-continued

<212> TYPE: DNA
<213> ORGANISM: Artificial Sequence
<220> FEATURE:
<223> OTHER INFORMATION: synthetic oligonucleotide

<400> SEQUENCE: 93
tcaatgcgca tgtggctact tcatcccatc gatttgccgg tgttccgata tgcgtc 56

<210> SEQ ID NO 94
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 94
cggaacaccg gcaaatcgat gggatgaagt agccacatgc gcattgatcg caacagg 57

<210> SEQ ID NO 95
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 95
caaaagctgt gcttgcggct acttcatccc atcgatttgt ttttgcgtcg acatcacgg 59

<210> SEQ ID NO 96
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 96
acgcaaaaac aaatcgatgg gatgaagtag ccgcaagcac agcttttgca tgcactatg 59

<210> SEQ ID NO 97
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 97
tcaatgcgca tgtttacgta tccttgctaa caaatgccgg tgttccgata tgcgtc 56

<210> SEQ ID NO 98
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 98
cggaacaccg gcatttgtta gcaaggatac gtaaacatgc gcattgatcg caacagg 57

<210> SEQ ID NO 99
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 99

-continued caaaagctgt gcttgcttac gtatccttgc taacaaatgt ttttgcgtcg acatcacgg 59

<210> SEQ ID NO 100
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 100
acgcaaaaac atttgttagc aaggatacgt aagcaagcac agcttttgca tgcactatg 59

<210> SEQ ID NO 101
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 101
gcgatcaatg cgcctgcaga actcaaccat atcctttatg tcggtgttcc gatatgcgtc 60

<210> SEQ ID NO 102
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 102
ggaacaccga cataaaggat atggttgagt tctgcaggcg cattgatcgc aacagggttt 60

<210> SEQ ID NO 103
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 103
caaaagctgt gcctgcagaa cacaacctta cccactttgt ttttgcgtcg acatcacgg 59

<210> SEQ ID NO 104
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 104
acgcaaaaac aaagtgggta aggttgtgtt ctgcaggcac agcttttgca tgcactatg 59

<210> SEQ ID NO 105
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 105
caaaagctgt gcctgcctgt taacacctac tcttaactgt ttttgcgtcg acatcacgg 59

<210> SEQ ID NO 106
<211> LENGTH: 59
<212> TYPE: DNA
<213> ORGANISM: Artificial Sequence -continued
<220> FEATURE:
<223> OTHER INFORMATION: synthetic oligonucleotide

<400> SEQUENCE: 106
acgcaaaaac agttaagagt aggtgttaac aggcaggcac agcttttgca tgcactatg 59

<210> SEQ ID NO 107
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 107
tcaatgcgca tgcgctcttc caactcattc taactgtcgg tgttccgata tgcgtct 57

<210> SEQ ID NO 108
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 108
cggaacaccg acagttagaa tgagttggaa gagcgcatgc gcattgatcg caacagg 57

<210> SEQ ID NO 109
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 109
caaaagctgt gcctgcgcgc ttcctacaca ctctaactgt ttttgcgtcg acatcacgg 59

<210> SEQ ID NO 110
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 110
acgcaaaaac agttagagtg tgtaggaagc gcgcaggcac agcttttgca tgcactatg 59

<210> SEQ ID NO 111
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 111
caaaagctgt gcctgccctt taggcctttg cccaccttgt ttttgcgtcg acatcacgg 59

<210> SEQ ID NO 112
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 112
acgcaaaaac aaggtgggca aaggcctaaa gggcaggcac agcttttgca tgcactat 58

-continued

<210> SEQ ID NO 113
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 113
aagctgtatc tgctggaaca tcgattctac accttgtttt tgcgtcgaca tcacgg 56

<210> SEQ ID NO 114
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 114
acgcaaaaac aaggtgtaga atcgatgttc cagcagatac agcttttgca tgcact 56

<210> SEQ ID NO 115
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 115
gcgatcaatg catctgtact tggattgaca gtactccttg tcggtgttcc gatatgcgtc 60

<210> SEQ ID NO 116
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 116
ggaacaccga caaggagtac tgtcaatcca agtacagatg cattgatcgc aacagggttt 60

<210> SEQ ID NO 117
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 117
aagctgtatc tgcacatgga tcgatagtac tccttgtttt tgcgtcgaca tcacgg 56

<210> SEQ ID NO 118
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 118
acgcaaaaac aaggtgtaga atcgatccat gtgcagatac agcttttgca tgcact 56

<210> SEQ ID NO 119
<211> LENGTH: 56
<212> TYPE: DNA
<213> ORGANISM: Artificial Sequence
<220> FEATURE:
<223> OTHER INFORMATION: synthetic oligonucleotide -continued

<400> SEQUENCE: 119
aagctgtatc tgtacatgga tcgattggac accttgtttt tgcgtcgaca tcacgg 56

<210> SEQ ID NO 120
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 120
acgcaaaaac aaggtgtcca atcgatccat gtacagatac agcttttgca tgcact 56

<210> SEQ ID NO 121
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 121
caaaagctgc gcatgtgtta ctacagattg gatcgaatgt ttttgcgtcg acatcacgg 59

<210> SEQ ID NO 122
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 122
acgcaaaaac attcgatcca atctgtagta acacatgcgc agcttttgca tgcactatg 59

<210> SEQ ID NO 123
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 123
caaaagctgt gcctgcccaa cactttggac tcatatgtgt ttttgcgtcg acatcacgga 60
c 61

<210> SEQ ID NO 124
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 124
acgcaaaaac acatatgagt ccaaagtgtt gggcaggcac agcttttgca tgcactatga 60
c 61

<210> SEQ ID NO 125
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 125
caaaagctgc gcatgttact actctcaatt ccaccaatgt ttttgcgtcg acatcacgg 59

-continued

<210> SEQ ID NO 126
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 126
acgcaaaaac attggtggaa ttgagagtag taacatgcgc agcttttgca tgcactatg 59

<210> SEQ ID NO 127
<211> LENGTH: 69
<212> TYPE: DNA
<213> ORGANISM: Artificial Sequence
<220> FEATURE:
<223> OTHER INFORMATION: synthetic oligonucleotide

<400> SEQUENCE: 127
caaaagctgt ctttgtccgg aaaacgataa cgtttctcct tgtaattgcg tcgacatcac 60
ggacttctg 69

<210> SEQ ID NO 128
<211> LENGTH: 69
<212> TYPE: DNA
<213> ORGANISM: Artificial Sequence
<220> FEATURE:
<223> OTHER INFORMATION: synthetic oligonucleotide

<400> SEQUENCE: 128
tgtcgacgca attacaagga gaaacgttat cgttttccgg acaaagacag cttttgcatg 60
cactatgac 69

<210> SEQ ID NO 129
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 129
caaaagctgt gcttgtaaac acaacgtacg tcttttatgt ttttgcg 47

<210> SEQ ID NO 130
<211> LENGTH: 55
<212> TYPE: DNA
<213> ORGANISM: Artificial Sequence
<220> FEATURE:
<223> OTHER INFORMATION: synthetic oligonucleotide

<400> SEQUENCE: 130
tcgacgcaaa aacataaaag acgtacgttg tgtttacaag cacagctttt gcatg 55

<210> SEQ ID NO 131
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 131
gatccaggtg gagctgcttt agttgacgat gagagct 37

<210> SEQ ID NO 132
<211> LENGTH: 29
<212> TYPE: DNA
<213> ORGANISM: Artificial Sequence -continued
<220> FEATURE:
<223> OTHER INFORMATION: synthetic oligonucleotide

<400> SEQUENCE: 132
ctcatcgtca actaaagcag ctccacctg 29

<210> SEQ ID NO 133
<211> LENGTH: 70
<212> TYPE: DNA
<213> ORGANISM: Artificial Sequence
<220> FEATURE:
<223> OTHER INFORMATION: synthetic oligonucleotide

<400> SEQUENCE: 133
gatccaggtg aacctgaccc aactcctcca tctgatcctg gagaataccc agcttgggac 60
gatgagagct 70

<210> SEQ ID NO 134
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 134
ctcatcgtcc caagctgggt attctccagg atcagatgga ggagttgggt caggttcacc 60
tg 62

<210> SEQ ID NO 135
<211> LENGTH: 79
<212> TYPE: DNA
<213> ORGANISM: Artificial Sequence
<220> FEATURE:
<223> OTHER INFORMATION: synthetic oligonucleotide

<400> SEQUENCE: 135
gatccggcga acctgcgtct gtctaagctt ggcctgctta tgaaatcaga ccatcagcac 60
agcaatgacg atgagagct 79

<210> SEQ ID NO 136
<211> LENGTH: 71
<212> TYPE: DNA
<213> ORGANISM: Artificial Sequence
<220> FEATURE:
<223> OTHER INFORMATION: synthetic oligonucleotide

<400> SEQUENCE: 136
ctcatcgtca ttgctgtgct gatggtctga tttcataagc aggccaagct tagacagacg 60
caggttcgcc g 71

<210> SEQ ID NO 137
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 137
gatccaaaat cagaccatca gcacagcaat gacgatgaga gct 43

<210> SEQ ID NO 138
<211> LENGTH: 35
<212> TYPE: DNA
<213> ORGANISM: Artificial Sequence
<220> FEATURE:
<223> OTHER INFORMATION: synthetic oligonucleotide -continued

<400> SEQUENCE: 138

```
ctcatcgtca ttgctgtgct gatggtctga ttttg                               35
```

<210> SEQ ID NO 139
<211> LENGTH: 205
<212> TYPE: DNA
<213> ORGANISM: Artificial Sequence
<220> FEATURE:
<223> OTHER INFORMATION: synthetic oligonucleotide

<400> SEQUENCE: 139

```
gatccaggag aaccggaccc aacgccccca agtgatccag gagagtatcc agcatgggat      60
tcaaatcaaa tttacacaaa tgaaattgtg tatcataacg gtcagttatg gcaagcgaaa     120
tggtggacac aaaatcaaga gccaggtgac ccatacggtc cgtgggaacc actcaaatct     180
gacccagatt cagacgatga gagct                                          205
```

<210> SEQ ID NO 140
<211> LENGTH: 197
<212> TYPE: DNA
<213> ORGANISM: Artificial Sequence
<220> FEATURE:
<223> OTHER INFORMATION: synthetic oligonucleotide

<400> SEQUENCE: 140

```
ctcatcgtct gaatctgggt cagatttgag tggttcccac ggaccgtatg ggtcacctgg      60
ctcttgattt tgtgtccacc atttcgcttg ccataactga ccgttatgat acacaatttc     120
atttgtgtaa atttgatttg aatcccatgc tggatactct cctggatcac ttgggggcgt     180
tgggtccggt tctcctg                                                    197
```

<210> SEQ ID NO 141
<211> LENGTH: 6
<212> TYPE: PRT
<213> ORGANISM: Artificial Sequence
<220> FEATURE:
<223> OTHER INFORMATION: linker peptide

<400> SEQUENCE: 141

```
Trp Gly Asp Pro His Tyr
 1               5
```

<210> SEQ ID NO 142
<211> LENGTH: 6
<212> TYPE: PRT
<213> ORGANISM: Artificial Sequence
<220> FEATURE:
<223> OTHER INFORMATION: linker peptide

<400> SEQUENCE: 142

```
Asp Asn Asn Asp Pro Ile
 1               5
```

<210> SEQ ID NO 143
<211> LENGTH: 6
<212> TYPE: PRT
<213> ORGANISM: Artificial Sequence
<220> FEATURE:
<223> OTHER INFORMATION: linker peptide

<400> SEQUENCE: 143

```
Val Val Ala Asp Pro Asn
 1               5
```

<210> SEQ ID NO 144
<211> LENGTH: 37
<212> TYPE: DNA
<213> ORGANISM: Artificial Sequence
<220> FEATURE:

-continued

<223> OTHER INFORMATION: synthetic oligonucleotide

<400> SEQUENCE: 144
tggcgttcag caacatgagc gcgcaggctg atgatta 37

<210> SEQ ID NO 145
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 145
taatcatcag cctgcgcgct catgttgctg aacgcca 37

<210> SEQ ID NO 146
<211> LENGTH: 128
<212> TYPE: DNA
<213> ORGANISM: Artificial Sequence
<220> FEATURE:
<223> OTHER INFORMATION: synthetic oligonucleotide

<400> SEQUENCE: 146
gacatcacgg acttctgcta tgagccatgt aaaccaagcg aggacgataa agagaactaa 60
aagcttaact cgaggttaac agaggacgga tttcctgaag gaaatccgtt tttttatttt 120
taattaag 128

<210> SEQ ID NO 147
<211> LENGTH: 130
<212> TYPE: DNA
<213> ORGANISM: Artificial Sequence
<220> FEATURE:
<223> OTHER INFORMATION: synthetic oligonucleotide

<400> SEQUENCE: 147
agctcttaat taaaaataaa aaaacggatt tccttcagga aatccgtcct ctgttaacct 60
cgagttaagc ttttagttct ctttatcgtc ctcgcttggt ttacatggct catagcagaa 120
gtccgtgatg 130

<210> SEQ ID NO 148
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 148
cagcaacatg agcgcgcagg ctg 23

<210> SEQ ID NO 149
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 149
atcgtctgga tccggatagt gggggtctcc ccaagatgct gattctctta ttttttccc 59

<210> SEQ ID NO 150
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 150

-continued

```
atcgtctgga tccggtatgg gatcattgtt gtcagatgct gattctctta ttttttccc       59


<210> SEQ ID NO 151
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 151

atcgtctgga tccgggttgg gatctgcaac tacagatgct gattctctta ttttttccc       59


<210> SEQ ID NO 152
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 152

gcataaggat gagtcatctg cagcg                                            25


<210> SEQ ID NO 153
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 153

atcgtctgga tccggatagt gggggtctcc ccacggttct cctggatcag atggcgg         57


<210> SEQ ID NO 154
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 154

atcgtctgga tccggtatgg gatcattgtt gtccggttct cctggatcag atggcgg         57


<210> SEQ ID NO 155
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 155

atcgtctgga tccgggttgg gatctgcaac taccggttct cctggatcag atggcgg         57


<210> SEQ ID NO 156
<211> LENGTH: 6
<212> TYPE: PRT
<213> ORGANISM: Artificial Sequence
<220> FEATURE:
<223> OTHER INFORMATION: linker peptide

<400> SEQUENCE: 156

Trp Gly Asp Pro His Tyr
 1               5


<210> SEQ ID NO 157
<211> LENGTH: 6
```

-continued

<212> TYPE: PRT
<213> ORGANISM: Artificial Sequence
<220> FEATURE:
<223> OTHER INFORMATION: linker peptide

<400> SEQUENCE: 157

```
Asp Asn Asn Asp Pro Ile
 1               5
```

<210> SEQ ID NO 158
<211> LENGTH: 6
<212> TYPE: PRT
<213> ORGANISM: Artificial Sequence
<220> FEATURE:
<223> OTHER INFORMATION: linker peptide

<400> SEQUENCE: 158

```
Val Val Ala Asp Pro Asn
 1               5
```

<210> SEQ ID NO 159
<211> LENGTH: 21
<212> TYPE: PRT
<213> ORGANISM: Artificial Sequence
<220> FEATURE:
<223> OTHER INFORMATION: linker peptide

<400> SEQUENCE: 159

```
Ile Pro Pro Ser Asp Pro Thr Pro Pro Ser Asp Pro Gly Glu Pro Trp
 1               5                  10                  15
Gly Asp Pro His Tyr
            20
```

<210> SEQ ID NO 160
<211> LENGTH: 21
<212> TYPE: PRT
<213> ORGANISM: Artificial Sequence
<220> FEATURE:
<223> OTHER INFORMATION: linker peptide

<400> SEQUENCE: 160

```
Ile Pro Pro Ser Asp Pro Thr Pro Pro Ser Asp Pro Gly Glu Pro Asp
 1               5                  10                  15
Asn Asn Asp Pro Ile
            20
```

<210> SEQ ID NO 161
<211> LENGTH: 21
<212> TYPE: PRT
<213> ORGANISM: Artificial Sequence
<220> FEATURE:
<223> OTHER INFORMATION: linker peptide

<400> SEQUENCE: 161

```
Ile Pro Pro Ser Asp Pro Thr Pro Pro Ser Asp Pro Gly Glu Pro Val
 1               5                  10                  15
Val Ala Asp Pro Asn
            20
```

<210> SEQ ID NO 162
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 162

```
gatccaggtg gagacgacga tgacaaagac gatgagagct                            40
```

<210> SEQ ID NO 163
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 163
ctcatcgtct ttgtcatcgt cgtctccacc tg 32

<210> SEQ ID NO 164
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 164
gatccaggtg ctgctcatta cgacgatgag agct 34

<210> SEQ ID NO 165
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 165
ctcatcgtcg taatgagcag cacctg 26

<210> SEQ ID NO 166
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 166
gatccacgtg ctaaaagaga cgatgagagc t 31

<210> SEQ ID NO 167
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 167
ctcatcgtct cttttagcac gtg 23

<210> SEQ ID NO 168
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 168
gatccaggcg ctgcacacta caacgacgat gagagct 37

<210> SEQ ID NO 169
<211> LENGTH: 29
<212> TYPE: DNA
<213> ORGANISM: Artificial Sequence
<220> FEATURE:

-continued

<223> OTHER INFORMATION: synthetic oligonucleotide

<400> SEQUENCE: 169
ctcatcgtcg ttgtagtgtg cagcgcctg 29

<210> SEQ ID NO 170
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 170
gatccattcc ttgaagacga tgagagct 28

<210> SEQ ID NO 171
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 171
ctcatcgtct tcaaggaatg 20

<210> SEQ ID NO 172
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 172
cccataccgg agccagacga tgagagctc 29

<210> SEQ ID NO 173
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 173
catcgtctgg ctccggtatg ggatcattgt tg 32

<210> SEQ ID NO 174
<211> LENGTH: 21
<212> TYPE: PRT
<213> ORGANISM: Artificial Sequence
<220> FEATURE:
<223> OTHER INFORMATION: linker peptide

<400> SEQUENCE: 174

```
Asp Asn Asn Asp Pro Ile Pro Glu Pro Asp Asp Glu Ser Phe Asn Met
 1               5                  10                  15
Pro Ile Pro Glu Pro
            20
```

<210> SEQ ID NO 175
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 175

-continued gatccaggcg ctgcacacta caaatcagac catcagcaca gcaatgacga tgagagct 58

<210> SEQ ID NO 176
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 176
ctcatcgtca ttgctgtgct gatggtctga tttgtagtgt gcagcgcctg 50

<210> SEQ ID NO 177
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 177
gatccaggcg ctgcacacta cgtagaattt caagacgatg agagct 46

<210> SEQ ID NO 178
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 178
ctcatcgtct tgaaattcta cgtagtgtgc agcgcctg 38

<210> SEQ ID NO 179
<211> LENGTH: 18
<212> TYPE: PRT
<213> ORGANISM: Artificial Sequence
<220> FEATURE:
<223> OTHER INFORMATION: cleavage site

<400> SEQUENCE: 179

```
Asp Asn Asn Asp Pro Ile Pro Asp Pro Gly Ala Ala His Tyr Val Glu
 1               5                  10                  15
Phe Gln
```

<210> SEQ ID NO 180
<211> LENGTH: 87
<212> TYPE: PRT
<213> ORGANISM: Artificial Sequence
<220> FEATURE:
<223> OTHER INFORMATION: synthetic fusion peptide

<400> SEQUENCE: 180

```
Lys Ile Arg Glu Ser Ala Ser Asp Asn Asn Asp Pro Ile Pro Asp Pro
 1               5                  10                  15
Asp Asp Glu Ser Ser Lys Pro Cys Cys Asp Gln Cys Ala Cys Thr Lys
            20                  25                  30
Ser Asn Pro Pro Gln Cys Arg Cys Ser Asp Met Arg Leu Asn Ser Cys
        35                  40                  45
His Ser Ala Cys Lys Ser Cys Ala Cys Tyr Asn Leu Tyr Gly Trp Thr
    50                  55                  60
Cys Phe Cys Val Asp Ile Thr Asp Phe Cys Tyr Glu Pro Cys Lys Pro
65                  70                  75                  80
Ser Glu Asp Asp Lys Glu Asn
                85
```

<210> SEQ ID NO 181
<211> LENGTH: 46
<212> TYPE: DNA

-continued

```
<213> ORGANISM: Artificial Sequence
<220> FEATURE:
<223> OTHER INFORMATION: synthetic oligonucleotide primer

<400> SEQUENCE: 181

      aacatgagcg cgcaggctga tgacgcggca attcaacaaa cgttag                46


<210> SEQ ID NO 182
<211> LENGTH: 77
<212> TYPE: DNA
<213> ORGANISM: Artificial Sequence
<220> FEATURE:
<223> OTHER INFORMATION: synthetic oligonucleotide primer

<400> SEQUENCE: 182

      tcgtctggat ccggtatggg atcattgttg tcaccagaac cactagttga tcctttaccg      60
      ctggtcattt tttggtg                                                      77


<210> SEQ ID NO 183
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 183

      tgcacttctc tgctttggtc tgttgaacgc agaggtcttg acaacaatga tcctattccg      60


<210> SEQ ID NO 184
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 184

      gatccggaat aggatcattg ttgtcaagac ctctgcgttc aacagaccaa agcagagaag      60
```